US011054413B2

(12) United States Patent
Martin et al.

(10) Patent No.: US 11,054,413 B2
(45) Date of Patent: Jul. 6, 2021

(54) MATERIALS AND METHODS FOR ASSAYING LIVING CELLS

(71) Applicants: Stuart Martin, Severna Park, MD (US); Christopher M. Jewell, Silver Spring, MD (US); James I. Andorko, Delran, NJ (US); Elisabeth Lily Sooklal, Reisterstown, MD (US); Rebecca Whipple Bettes, Elkridge, MD (US); Kristi Chakrabarti, Silver Spring, MD (US)

(72) Inventors: Stuart Martin, Severna Park, MD (US); Christopher M. Jewell, Silver Spring, MD (US); James I. Andorko, Delran, NJ (US); Elisabeth Lily Sooklal, Reisterstown, MD (US); Rebecca Whipple Bettes, Elkridge, MD (US); Kristi Chakrabarti, Silver Spring, MD (US)

(73) Assignees: UNIVERSITY OF MARYLAND, COLLEGE PARK, College Park, MD (US); UNIVERSITY OF MARYLAND, BALTIMORE, Baltimore, MD (US)

( * ) Notice: Subject to any disclaimer, the term of this patent is extended or adjusted under 35 U.S.C. 154(b) by 389 days.

(21) Appl. No.: 14/877,864

(22) Filed: Oct. 7, 2015

(65) Prior Publication Data
US 2016/0097769 A1 Apr. 7, 2016

Related U.S. Application Data

(63) Continuation-in-part of application No. PCT/US2015/024207, filed on Apr. 3, 2015.

(60) Provisional application No. 62/068,034, filed on Oct. 24, 2014, provisional application No. 61/974,753, filed on Apr. 3, 2014.

(51) Int. Cl.
G01N 33/50 (2006.01)
G01N 21/95 (2006.01)
G01N 33/574 (2006.01)
G02B 21/00 (2006.01)

(52) U.S. Cl.
CPC ......... *G01N 33/5026* (2013.01); *G01N 21/95* (2013.01); *G01N 33/50* (2013.01); *G01N 33/574* (2013.01); *G02B 21/0028* (2013.01); *G01N 2800/7028* (2013.01)

(58) Field of Classification Search
None
See application file for complete search history.

(56) References Cited

U.S. PATENT DOCUMENTS

| 8,193,238 B2 | 6/2012 | Martin |
| 2009/0137473 A1 | 5/2009 | Martin |
| 2013/0225656 A1 | 8/2013 | Iragavarapu-Charyulu |
| 2014/0093953 A1 | 4/2014 | Ingram |
| 2014/0093962 A1 | 4/2014 | Ingram et al. |
| 2014/0094383 A1* | 4/2014 | Lee .................. G01N 33/5432 506/9 |
| 2017/0184568 A1 | 6/2017 | Martin |

FOREIGN PATENT DOCUMENTS

| WO | 2003/035278 A1 | 5/2003 |
| WO | 2007/104011 A2 | 9/2007 |
| WO | 2008/144506 A1 | 11/2008 |
| WO | 2012/162345 A1 | 11/2012 |
| WO | 2015/153948 A2 | 10/2015 |

OTHER PUBLICATIONS

Daniel et al., Biointerphases, vol. 2, No. 3, Sep. 2007, pp. 109-118.*
Liu et al, Chem Commun (Camb), Sep. 14, 2009; vol. 14, No. 34: pp. 5100-5102.*
Nagrath et al., Nature, vol. 450 Dec. 20/27, 2007, pp. 1235-1241 (Year: 2007).*
Picone et al., PloS Biology (2010) vol. 8, Issue 11, pp. 1-17 (Year: 2010).*
Nikon et al., Introduction to Phase Contrast Microscopy, retrieved from the internet May 22, 2020: https://www.microscopyu.com/techniques/phase-contrast/introduction-to-phase-contrast-microscopy (Year: 2020).*
Lee et al., American Chemical Society-Nano (2011), vol. 5, No. 7, pp. 5444-5456 (Year: 2011).*
Extended European Search Report from European Appl. No. 15852876, dated Feb. 20, 2018.
Yamaguchi et al., Photocontrollable Dynamic Micropatterning of Non-adherent Mammalian Cells Using a Photocleavable Poly(ethylene glycol) Lipid, Angewandte Chemie, Supporting Information, (2011).
Matrone et al., Metastatic breast tumors express increased tau, which promotes microtentacle formation and the reattachment of detached breast tumor cells, Oncogene, 29:3217-3227 (2010).
Whipple et al., Detyrosinated microtubule protrusions in suspended mammary epithelial cells promote reattachment, Experimental Cell Research, 313:1326-1336 (2007).
Charpentier et al., Curcumin targets breast cancer stem-like cells with microtentacles that persist in mammospheres and promote reattachment, Cancer Res, 74:1250-1260 (2014).
Charpentier et al., Interplay of Stem Cell Characteristics, EMT, and Microtentacles in Circulating Breast Tumor Cells, Cancers, 5:1545-1565 (2013).

(Continued)

*Primary Examiner* — Scott Long
*Assistant Examiner* — Evelyn Y Pyla
(74) *Attorney, Agent, or Firm* — Nevrivy Patent Law Group P.L.L.C.

(57) ABSTRACT

The present invention provides a device for assaying living cells comprising a substrate, wherein the substrate comprises one or more tethering molecules which adhere to the substrate and are capable of interacting with cell membranes of the cells, wherein the cells maintain a free-floating, non-adherent character when bound to the one or more tethering molecules.

31 Claims, 40 Drawing Sheets

(56) References Cited

OTHER PUBLICATIONS

International Search Report from Appl. No. PCT/US2015/054571, United States Patent and Trademark Office, dated Dec. 31, 2015.
Matrone el al., Microtentacles Tip the Balance of Cytoskeletal Forces in Circulating Tumor Cells, Cancer Res, 70:7737-7741 (2010).
Charpentier, Clinical Studies Co-Investigator UMGCC-0902: A Feasibility Study to Identify Microtentacles and Stem Cell Phenotype of Circulating Cancer Cells in Metastatic Breast Cancer Patients Aug. 2010-Present, Biochemistry and Molecular Biology, 1-125 (2014).
European Official Communication from Appl. No. 15772640.7, European Patent Office, dated Oct. 4, 2017.
Kidambi et al., Controlling Primary Hepatocyte Adhesion and Spreading on Protein-Free Polyelectronlyte Multilayer Films, Journal of American Chemical Society, 126:16286-16287 (2004).
Aceto et al., Circulating tumor cell clusters are oligoclonal precursors of breast cancer metastasis, Cell, 158: 1110-1122 (2014).
Adams et al., Highly Efficient Circulating Tumor Cell Isolation from Whole Blood and Label-Free Enumeration Using Polymer-Based Microfluidics with an Integrated Conductivity Sensor, Journal of the American Chemical Society, 130:8633-8641 (2008).
Balzer et al., Anti-mitotic chemotherapeutics promote adhesive responses in detached and circulating tumor cells, Breast Cancer Res Treat, 121:65-78 (2010).
Bhandary et al., Rock inhibition promotes microtentacles that enhance reattachment of breast cancer cells, Oncotarget, 6:6251-6266 (2015).
Brouquet et al., A model of primary culture of colorectal cancer and liver metastasis to predict chemosensitivity, The Journal of surgical research, 166:247-254 (2011).
Chambers et al., Dissemination and Growth of Cancer Cells in Metastatic Sites, Nat Rev Cancer, 2:563-572 (2002).
Cristofanilli et al., Circulating Tumor Cells, Disease Progression, and Survival in Metastatic Breast Cancer, The New England Journal of Medicine, 351:781-791 (2004).
Cristofanilli et al., Circulating Tumor Cells: A Novel Prognostic Factor for Newly Diagnosed Metastatic Breast Cancer, J Clin Oncol, 23:1420-1430 (2005).
Cristofanilli et al., Circulating tumor cells in breast cancer: Advanced tools for "tailored" therapy?, Proc Natl Acad Sci USA, 103:17073-17074 (2006).
De Bono et al., Circulating Tumor Cells Predict Survival Benefit from Treatment in Metastatic Castration-Resistant Prostate Cancer, Clin Cancer Res, 14:6302-6309 (2008).
De Rose et al., Tumor grafts derived from women with breast cancer authentically reflect tumor pathology, growth, metastasis and disease outcomes, Nat Med, 17:1514-1520 (2011).
De Rose et al., Patient-derived models of human breast cancer: protocols for in vitro and in vivo applications in tumor biology and translational medicine, Current protocols in pharmacology / editorial board, SJ Enna Chapter 14: Unit14 23 (2013).
Flessner et al., Degradable polyelectrolyte multilayers that promote the release of siRNA, Langmuir: the ACS journal of surfaces and colloids, 27:7868-7876 (2011).
Hekimian et al., Epithelial Cell Dissemination and Readhesion: Analysis of Factors Contributing to Metastasis Formation in Breast Cancer, ISRN Oncol, Article ID 601810, 8 pages (2012).
Kato et al., Immobilized culture of nonadherent cells on an oleyl poly(ethylene glycol) ether-modified surface, Biotechniques, 35:1014-1018, 1020-1021 (2003).
Li et al., Acoustic separation of circulating tumor cells, Proceedings of the National Academy of Sciences, 112:4970-4975 (2015).
Kohli et al., Arrays of lipid bilayers and liposomes on patterned polyelectrolyte templates, J Colloid Interface Sci, 301: 461-469 (2006).
Krebs et al., Evaluation and Prognostic Significance of Circulating Tumor Cells in Patients With Non-Small-Cell Lung Cancer, J Clin Oncol, 29:1556-1563 (2011).
Jewell et al., Release of Plasmid DNA from Intravascular Stents Coated with Ultrathin Multilayered Polyelectrolyte Films, Biomacromolecules 7:2483-2491 (2006).
Jewell et al., Multilayered polyelectrolyte films promote the direct and localized delivery of DNA to cells, Journal of controlled release, 106:214-223 (2005).
Jewell et al., Multilayered polyelectrolyte assemblies as platforms for the delivery of DNA and other nucleic acid-based therapeutics, Advanced drug delivery reviews, 60:979-999 (2008).
Joosse et al., Biology, detection, and clinical implications of circulating tumor cells, EMBO Mol Med, 7:1-11 (2015).
Mendelsohn et al., Rational Design of Cytophilic and Cytophobic Polyelectrolyte Multilayer Thin Films, Biomacromolecules, 4:96-106 (2003).
Mitchell et al., Surfactant Functionalization Induces Robust, Differential Adhesion of Tumor Cells and Blood Cells to Charged Nanotube-Coated Biomaterials Under Flow, Biomaterials, 56:179-186 (2015).
O'Brien et al., The effect of pore size on cell adhesion in collagen-GAG scaffolds, Bio materials, 26:433-441 (2005).
Pachmann et al., Monitoring the Response of Circulating Epithelial Tumor Cells to Adjuvant Chemotherapy in Breast Cancer Allows Detection of Patients at Risk of Early Relapse, J Clin Oncol, 26:1208-1215 (2008).
Pantel et al., The biology of circulating tumor cells, Oncogene, 35:1216-1224 (2016).
Park et al., Full Surface Embedding of Gold Clusters on Silicon Nanowires for Efficient Capture and Photothermal Therapy of Circulating Tumor Cells, Nano Letters, 12:1638-1642 (2012).
Plaks et al., Circulating Tumor Cells, Science, 341:1186-1188 (2013).
Pierga et al., CirculatingTumor Cell Detection Predicts EarlyMetastatic RelapseAfter Neoadjuvant Chemotherapy in Large Operable and LocallyAdvanced Breast Cancer in a Phase II Randomized Trial, Clin Cancer Res, 14:7004-7010 (2008).
Reategui, Tunable Nanostructured Coating for the Capture and Selective Release of Viable Circulating Tumor Cells, Adv Mater, 27:1593-1599 (2015).
Rhee et al., Patterned cell culture inside microfluidic devices, Lab on a Chip, 5:102-107 (2005).
Richert et al., Improvement of Stability and Cell Adhesion Properties of Polyelectrolyte Multilayer Films by Chemical Cross-Linking, Biomacromolecules, 5:284-294 (2004).
Sarioglu et al., A microfluidic device for label-free, physical capture of circulating tumor cell-clusters, Nat Meth, 12:685-691 (2015).
Saurer et al., Polyelectrolyte multilayers promote stent-mediated delivery of DNA to vascular tissue, Biomacromolecules, 14:1696-1704 (2013).
Selden et al., Chemically programmed cell adhesion with membrane-anchored oligonucleotides, Journal of the American Chemical Society 134:765-768 (2012).
Slade et al., Comparison of bone marrow, disseminated tumour cells and blood-circulating tumour cells in breast cancer patients after primary treatment, Br J Cancer, 100:160-166 (2009).
Stoler et al., Breast epithelium procurement from stereotactic core biopsy washings: flow cytometry-sorted cell count analysis, Clin Cancer Res, 8:428-432 (2002).
Stott et al. Isolation of circulating tumor cells using a microvortex-generating herringbone-chip, Proceedings of the National Academy of Sciences, 107:18392-18397 (2010).
Sun et al., Assembly of Multilayered Films Using Well-Defined, End-Labeled Poly(acrylic acid): Influence of Molecular Weight on Exponential Growth in a Synthetic Weak Polyelectrolyte System, Langmuir, 23:8452-8459 (2007).
Chippada et al., A Nonintrusive Method of Measuring the Local Mechanical Properties of Soft Hydrogel Using Magnetic Microneedles, Journal of Biomechanical Engineering, 131:021014-1-12 (2009).
Takao et al., Enumeration, characterization, and collection of intact circulating tumor cells by cross contamination-free flow cytometry. Cytometry Part A:journal of the International Society for Advancement of Cytometry, 79:107-117 (2011).

(56) References Cited

OTHER PUBLICATIONS

Vitolo et al., Loss of PTEN induces microtentacles through PI3K-independent activation of cofilin, Oncogene, 32(17): doi:10.1038/onc.2012.234 (2013).
Wang et al., Enrichment of Prostate Cancer Stem-Like Cells from Human Prostate Cancer Cell Lines by Culture in Serum-Free Medium and Chemoradiotherapy, International journal of biological sciences, 9:472-479 (2013).
Whipple et al., Vimentin filaments support extension of tubulin-based microtentacles in detached breast tumor cells, Cancer Research, 68:5678-5688 (2008).
Zhang et al., Forming Lipid Bilayer Membrane Arrays on Micropatterned Polyelectrolyte Film Surfaces ,Chemistry A European Journal, 19:9059-9063 (2013).
Whipple et al., Epithelial-to-mesenchymal transition promotes tubulin detyrosination and microtentacles that enhance endothelial engagement, Cancer Res, 70:8127-8137 (2010).
Whipple et al., Parthenolide and costunolide reduce microtentacles and tumor cell attachment by selectively targeting detyrosinated tubulin independent from NF-κB inhibition, Breast Cancer Research, 15:R83 (2013).
Yamahira et al., Collagen Surfaces Modified with Photo-Cleavable Polyethylene Glycol-Lipid Support Versatile Single-Cell Arrays of Both Non-adherent and Adherent Cells, Macromol Biosci, 14:1670-1676 (2014).
Yamaguchi et al., Photocontrollable Dynamic Micropatterning of Non-adherent Mammalian Cells Using a Photocleavable Poly(ethylene glycol) Lipid, Angew Chem Int Ed Engl, 51:128-131(2012).
Yang et al., New class of ultrathin, highly cell-adhesion-resistant polyelectrolyte multilayers with micropatterning capabilities, Biomacromolecules, 4:987-994 (2003).
Yang et al., Cellular interactions on nano-structured polyelectrolyte multilayers, Colloids and Surfaces A: Physicochemical and Engineering Aspects, 313-314:526-529 (2008).
Yoon et al., Local anesthetics inhibit kinesin motility and microtentacle protrusions in human epithelial and breast tumor cells, Breast Cancer Res Treat, 129:691-701 (2011).
Yoon et al., Circulating tumor cells: approaches to isolation and characterization, Breast Cancer Res Treat, 129:691-701 (2011).
Yu et al., Circulating tumor cells: approaches to isolation and characterization, JCB: Review, 192:373-382 (2011).
Yu et al., Ex vivo culture of circulating breast tumor cells for individualized testing of drug susceptibility, Science, 345:216-220 (2014).
Yu et al., Circulating Breast Tumor Cells Exhibit Dynamic Changes in Epithelial and Mesenchymal Composition, Science, 339:580-584 (2013).
Zanina et a., Differences in Caco-2 Cell Attachment, Migration on Collagen and Fibronectin Coated Polyelectrolyte Surfaces, Biotechnol Bioproc E, 18:144-154 (2013).
Zheng et al., Precise Control of Cell Adhesion by Combination of Surface Chemistry and Soft Lithography, Advanced Healthcare Materials, 2:95-108 (2013).
Office Action from U.S. Appl. No. 15/301,587, dated Mar. 5, 2018.
Bockhorn et al., Active versus passive mechanisms in metastasis: do cancer cells crawl into vessels, or are they pushed?, Lancet Oncology, 8:444-448 (2007).
Office Action from U.S. Appl. No. 15/301,587, dated Aug. 27, 2018.
U.S. Office Action from U.S. Appl. No. 15/301,587, dated Apr. 17, 2019.
U.S. Office Action from U.S. Appl. No. 15/301,587, dated Apr. 30, 2020.
Afanasenkau et al., Positively Charged Supported Lipid Bilayers as a Biomimetic Platform for Neuronal Cell Culture, Langmuir, (2012), 28:13387-13394.
Chung et al., Formation and analysis of topological domains between lipid membranes tethered by DNA hybrids of different lengths, Faraday Discuss, (2013), 161:333-459.
Wang et al., Defining Single Molecular Forces Required to Activate Integrin and Notch Signaling, Science, (2013), 24:991-994.
European communication from EP Appl. No. 15852876.0, dated Jan. 30, 2020.

\* cited by examiner

FIG. 13

| | LnCAP | DU145 | PC3 |
|---|---|---|---|
| Confocal Fluorescence microscopy | | | |
| Differential Interference Contrast (DIC) | | | |
| McTN frequency | 9% | 30% | 57% |
| Avg. McTNs/cell (>3μm) | 1 | 5 | 5 |
| Avg. McTN length | 2.6μm | 3.7μm | 3.7μm |
| Integrated McTN score (freq. x length x #/cell) | 23.4 | 555.0 | 1054.5 |
| Prostate stem cell markers (from literature) | | | |
| CD44+/CD24- | 0.04% | 10% | N.D. |
| CD44+/α2β1+ | 0.08% | 24.25% | 10.85% |
| CD44+/CD133+ | 0% | 10.3% | 3.0% |
| Nestin mRNA (fold over benign) | 0 | 5 | 45 |

Microfluidic device to image free-floating patient tumor cells

Movie frame every 15 seconds, 5 z-stacks (Playback 200x, 40 minute timelapses)

B. ∗ Crosslinking DOTAP tethers

A. ∗ McTNs remain unchanged on PEM +/- DOTAP

FIG. 40

Tethered cell array benefits

A - Groups cells for efficient imaging without clustering

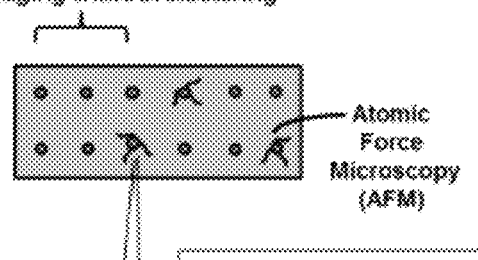
— Atomic Force Microscopy (AFM)

B - Facilitates comparison of McTN behavior and tumor cell mechanical properties (Micropipette, AFM)

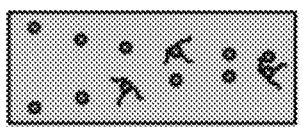
C - Enables measurement of effective cell contact distance +/- drugs

D - Enables cell fate studies
Tethered Mammospheres

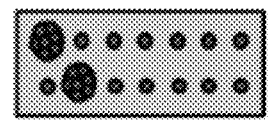

+ Y27632

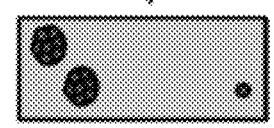 Stem cell *Selection*

OR?

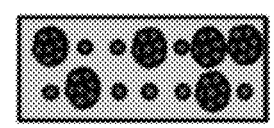 Stem cell *Conversion*

MATERIALS AND METHODS FOR ASSAYING LIVING CELLS

CROSS REFERENCE TO RELATED APPLICATIONS

This application is a continuation-in-part of International Application No: PCT/US15/24207, filed Apr. 3, 2015, which claims the benefit of U.S. Provisional Appl. Nos. 61/974,753, filed Apr. 3, 2014 and 62/068,034, filed Oct. 24, 2014. The content of the aforesaid applications are relied upon and incorporated by reference in their entireties.

STATEMENT OF FEDERALLY SPONSORED RESEARCH AND DEVELOPMENT

This invention was made with government support under Grant No. CA154624 awarded by the National Institutes of Health and Grant Number. W81XWH-11-1-0244 awarded by the U.S. Army Medical Research Material Command. The government has certain rights in the invention.

FIELD OF THE INVENTION

The field of the invention relates to the fields of cancer, particularly methods of diagnosis/prognosis and treatment of metastatic cancer and materials and devices useful for the same.

BACKGROUND OF THE INVENTION

Circulating tumor cells (CTCs) are shed from a primary tumor into the bloodstream. Such cells can nucleate new tumor masses at sites distant to the primary tumor. The presence of CTC's in a cancer patient's blood is associated with a poorer disease prognosis, and methods are available to measure the number CTCs in a cancer patient's bloodstream. However, CTCs are usually present in very small numbers, and some patients in whom CTCs are not detected eventually do develop tumor metastases. Accordingly, new methods are needed for identifying patients at risk for developing tumor metastases.

Microtentacles (McTNs) are microtubule-based protrusions of the membrane of certain types of tumor cells. Microtubules composed of detyrosinated alpha-tubulin (Glu-tubulin) or acetylated tubulin (Ace-tubulin) have vastly increased stability in vivo, persisting for hours rather than the three to five minutes observed for microtubules composed of tyrosinated tubulin (Tyr-tubulin). Microtentacles are supported by stable microtubules, enriched with Glu-tubulin or Ace-tubulin. Upregulation of the intermediate filament vimentin is another mechanism by which tumor cells stabilize microtubules. Experimental metastasis studies revealed that promotion of microtentacles increases lung retention of CTCs (Balzer E M, Whipple R A, Thompson K, Boggs A E, Slovic J, Cho E H et al (2010). c-Src differentially regulates the functions of microtentacles and invadopodia. *Oncogene* 29: 6402-6408); (Matrone M A, Whipple R A, Thompson K, Cho E H, Vitolo M I, Balzer E M et al (2010). Metastatic breast tumors express increased tau, which promotes microtentacle formation and the reattachment of detached breast tumor cells. *Oncogene* 29: 3217-3227). Moreover, previous studies in animal models have shown that CTCs reattach to blood vessel walls with a tubulin-dependent cytoskeletal mechanism that appears to rely on the presence of microtentacles (Korb T, Schluter K, Enns A, Spiegel H U, Senninger N, Nicolson G L et al (2004). Integrity of actin fibers and microtubules influences metastatic tumor cell adhesion. *Experimental cell research* 299: 236-247). Microtentacles also promote tumor cell clustering, and clusters of CTCs have recently been shown to have 50-fold higher metastatic potential (Aceto N, Bardia A, Miyamoto D T, Donaldson M C, Wittner B S, Spencer J A et al (2014). Circulating tumor cell clusters are oligoclonal precursors of breast cancer metastasis. *Cell* 158: 1110-1122). Accordingly, the presence of microtentacles on the surface of a tumor cell indicates a poorer patient prognosis.

Circulating tumor cells (CTCs) can lead to metastatic recurrence but the effects of current cancer drugs on the dynamic responses of these free-floating tumor cells is almost completely overlooked. There is growing evidence that the presence of CTCs in the bloodstream of breast cancer patients predicts poor outcome and an increased risk of metastatic recurrence (Hekimian, K., et al., *ISRN Oncol*, 2012. 2012: 601810; Riethdorf, S. and K. Pantel, *Pathobiology*, 2008. 75: 140-8; Ross, J. S. and E. A. Slodkowska, *Am J Clin Pathol*, 2009. 132: 237-45). Persistent cell cycle arrest renders CTCs highly resistant to traditional chemotherapies targeting cell growth or division (Naumov, G. N., et al., *Cancer Res*, 2002. 62: 2162-8; Naumov, G. N., et al., *Breast Cancer Res Treat*, 2003. 82: 199-206). Current clinical studies and ongoing drug development focus on inhibiting growth or invasion of attached tumor cells and largely overlook drug effects on free-floating CTCs (Kim, L. C., L. Song, and E. B. Haura, *Nat Rev Clin Oncol*, 2009. 6: 587-95; Le, X. F. and R. C. Bast, Jr., *Cancer Biol Ther*, 2011. 12; Patel, R. A., et al., *Oncogene*, 2013). This could be an important blind-spot since surgery and neoadjuvant chemotherapy can dramatically increase levels of CTCs if every primary tumor cell is not successfully removed or destroyed (Momma, T., et al., *Cancer Res*, 1998. 58: 5425-31; Goldfarb, Y. and S. Ben-Eliyahu, *Breast Dis*, 2006. 26: 99-114). This post-treatment CTC increase predicts poor long-term patient outcome (Pachmann, K., et al., *J Clin Oncol*, 2008. 26: 1208-15; Hekimian, K., et al., *ISRN Oncol*, 2012. 2012: 601810) highlighting the need to better understand the determinants of CTC metastasis during the post-treatment window.

Free-floating tumor cells produce microtentacles that promote metastatic reattachment. Studies have identified that mammary epithelial and breast carcinoma cells produce extensions of the plasma membrane when detached from extracellular matrix (ECM) (Whipple, R. A., et al., *Cancer Res*, 2008. 68: 5678-88; Whipple, R. A., A. M. Cheung, and S. S. Martin, *Exp Cell Res*, 2007. 313: 1326-36) (See FIG. 1). These extensions occur with higher frequency in metastatic breast tumor cell lines (Whipple, R. A., et al., *Cancer Res*, 2008. 68: 5678-88). Unlike the actin-based invadopodia and filopodia that are well-characterized in tumor cells attached to extracellular matrix, these extensions are based on microtubule expansion and actively suppressed by contraction of the actin cortex beneath the plasma membrane (Matrone, M. A., et al., *Cancer Res*, 2010. 70: 7737-41). Since such structures had not been reported previously in tumor cells, the term, microtentacles was coined to describe them (Whipple, R. A., et al., *Cancer Res*, 2008. 68: 5678-88).

Microtentacles can encircle adjacent cells promoting reattachment of tumor cells to each other and extracellular matrix (Whipple, R. A., et al., *Cancer Res*, 2008. 68: 5678-88; Whipple, R. A. et al., *Exp Cell Res*, 2007. 313: 1326-36), but are not observed when cells are grown attached to matrix. There is currently an overwhelming focus of the tumor biology field on cells that are attached to flattened or 3-dimensional extracellular matrix proteins (Yamaguchi, H., J. Wyckoff, and J. Condeelis, *Curr Opin Cell Biol*, 2005. 17: 559-64; Fischbach, C., et al., *Nat Methods*, 2007. 4: 855-60), which limits the understanding of cytoskeletal dynamics in free-floating CTCs. Studies using intravital microscopy have shown that the ability of tumor cells to adhere to capillary endothelial cells while circulating in vivo depends on tubulin and not actin (Korb, T., et al., *Exp Cell Res*, 2004. 299: 236-47). While these studies were conducted at a relatively macroscopic level, the mechanism by which CTCs bind blood vessel walls in vivo (Korb, T., et al., *Exp Cell Res*, 2004. 299: 236-47) therefore matches precisely with the mechanisms underlying the McTNs that we observe microscopically in detached tumor cells (Matrone, M. A., et al., *Cancer Res*, 2010. 70: 7737-41; Whipple, R. A., et al., *Cancer Res*, 2008. 68: 5678-88; Whipple, R. A., A. M. Cheung, and S. S. Martin, *Exp Cell Res*, 2007. 313: 1326-36). It has also been published that elevating McTNs by increasing microtubule stabilization or decreasing actin contraction can promote the retention of CTCs in the lung capillaries of living mice (Balzer, E. M., et al., *Oncogene*, 2010. 29: 6402-8; Matrone, M. A., et al., *Oncogene*, 2010. 29: 3217-27) (See FIG. 2).

Cancer drugs aimed at tumor growth and invasion can promote McTNs and stem cell characteristics. Recent developments show that inhibition of actin contractility by targeting the Rho-kinase (ROCK) strongly promotes the ability of epithelial tumor cells from patients to grow indefinitely (Liu, X., et al., *Am J Pathol*, 2012. 180: 599-607; Suprynowicz, F. A., et al., *Proc Natl Acad Sci USA*, 2012. 109: 20035-40). Moreover, treatment with ROCK inhibitor also directly increases tumor stem cell characteristics (Ohata, H., et al., *Cancer Res*, 2012. 72: 5101-10) and McTNs (Bhandary L, Whipple R A, Vitolo M I, Charpentier M S, Boggs A E, Chakrabarti K R, Thompson K N, Martin S S. ROCK inhibition promotes microtentacles that enhance reattachment of breast cancer cells. *Oncotarget*. 2015 Jan. 31. [Epub ahead of print] PMID: 25749040). Nevertheless, clinical trials with ROCK inhibitors are proceeding (Ying, H., et al., *Mol Cancer Ther*, 2006. 5: 2158-64; Yap, T. A., et al., *Clin Cancer Res*, 2012. 18: 3912-23; Vigil, D., et al., *Cancer Res*, 2012. 72: 5338-47), due to the efficacy of these inhibitors at reducing tumor cell growth and invasion in some model systems. Similarly, reinforcement of microtubules with Paclitaxel also increases stem cell characteristics and even tumor metastasis (Gupta, P. B., et al., *Cell*, 2009. 138: 645-59). It is notable that both of these drug effects (actin weakening, microtubule stabilization) simulate the cytoskeletal alterations that accompany wound healing and matrix detachment (Even-Ram, S., et al., *Nat Cell Biol*, 2007. 9: 299-309; Gundersen, G. G. and J. C. Bulinski, *Proc Natl Acad Sci USA*, 1988. 85: 5946-50) (See FIG. 3).

Drugs which reduce actin (Jasplakinolide-Jas) or stabilize tubulin (Paclitaxel-Taxol) strongly promote McTNs (Balzer, E. M., et al., *Breast Cancer Res Treat*, 2010. 121: 65-78) (See FIG. 4), again supporting a model that these drugs could stimulate wound healing or detachment responses in tumor cells. Similar McTN induction occurs when actin contraction is reduced by targeting Src (Balzer, E. M., et al., *Oncogene*, 2010. 29: 6402-8). It is therefore possible that targeting the cytoskeleton in these ways can reduce tumor growth and motility in the short-term, but may promote increased stem cell characteristics (Ohata, H., et al., *Cancer Res*, 2012. 72: 5101-10) and tumor recurrence over the long-term (Hekimian, K., et al., *ISRN Oncol*, 2012. 2012: 601810). Even the most sensitive clinical imaging methods (MRI/PET-CT) can only detect foci of approximately 5 million tumor cells (Li, G., et al., *J Appl Clin Med Phys*, 2008. 9: 2781), emphasizing that both current drug development and patient monitoring are overlooking effects on tumor cells below this clinical detection threshold, like CTCs.

Neoadjuvant drug effects on CTCs could be increasing metastatic risk. While the concentration of Taxol (1.2 µM) that promotes McTNs is higher than that used to inhibit cell division, it is worth noting that a routine clinical dose (175 mg/m$^2$) yields blood levels of >60 µM Taxol that do not decrease below 1.2 µM until 6 hours following infusion (Bulitta, J. B., et al., *Cancer Chemother Pharmacol*, 2009. 63: 1049-63). Since CTCs travel from primary tumors to distant tissues within minutes (Chambers, A. F., A. C. Groom, and I. C. MacDonald, *Nat Rev Cancer*, 2002. 2: 563-72), this provides ample opportunity for Taxol treatment to influence CTC retention at metastatic sites. Neoadjuvant Taxol treatment also increases CTCs more than 1000-fold (Pachmann, K., et al., *J Clin Oncol*, 2008. 26: 1208-15) when used in advance of surgery. Since neoadjuvant taxane treatment is growing more common (Gralow, J., et al., *Clin Breast Cancer*, 2008. 8: 33-7), these results emphasize the importance of determining how an individual patient's tumor cells respond to neoadjuvant chemotherapy. During neoadjuvant therapy, a subset of patients unfortunately can show rapid progression (Caudle, A. S., et al., *J Clin Oncol*, 2010. 28: 1821-8), and there is currently a need to better predict which patients are at risk for progression during neoadjuvant treatment. A recent clinical study involving 1,762 patients did not detect an appreciable advantage of neoadjuvant therapy to overall patient survival, but 59 of these patients rapidly progressed to metastatic disease, and the one of the greatest risk factors was inclusion of a tubulin-stabilizing taxane in the neoadjuvant regimen (Caudle, A. S., et al., *J Clin Oncol*, 2010. 28: 1821-8). Current clinical imaging technology makes it very difficult to distinguish if a tumor is shrinking on an MRI because it is dying or because the tumor is scattering (Li, G., et al., *J Appl Clin Med Phys*, 2008. 9: 2781). These two scenarios have dramatically different implications for the patient. Careful monitoring of CTC levels when chemotherapy was given before surgery (Hekimian, K., et al., *ISRN Oncol*, 2012. 2012: 601810) (See FIG. 5) showed that when CTCs increased in the bloodstream during therapy, only 4% of these patients were relapse-free after 7 years, while 100% of patients whose CTCs decreased remained relapse-free at 7 years. This 25-fold increased risk of relapse (Hekimian, K., et al., *ISRN Oncol*, 2012. 2012: 601810) clearly emphasizes the importance of understanding how current cancer drugs could affect the cytoskeletal mechanics of free-floating CTCs. These results (Hekimian, K., et al., *ISRN Oncol*, 2012. 2012: 601810) and the current limitations of clinical imaging (Li, G., et al., *J Appl Clin Med Phys*, 2008. 9: 2781) highlight the need to better understand the mechanisms that influence CTC metastasis in individual patients to effectively guide therapy.

Live confocal imaging demonstrates that McTNs promote aggregation and endothelial attachment of free-floating tumor cells. The inventor's lab determined that the delicate structure of McTNs required new methods to image dynamic shape changes in live, detached tumor cells (Balzer, E. M., et al., *Oncogene*, 2010. 29: 6402-8; Balzer, E. M., et al., *Breast Cancer Res Treat*, 2010. 121: 65-78; Whipple, R. A., et al., *Cancer Research*, 2008. 68: 5678-88). Using high-speed confocal microscopy, the inventor has shown that McTNs encircle neighboring cells to promote the aggregation of detached tumor cells (Matrone, M. A., et al.,

*Cancer Res*, 2010. 70: 7737-41) (See FIG. 6). Such resolution of individual McTNs would be impossible with traditional fixed-cell immunofluorescence or even electron microscopy, since surface or cytoskeletal stains cannot distinguish between the neighboring cells (See FIG. 6A). The discovery that McTNS promote tumor cell clustering is particularly notable since CTCs clusters have recently been shown to have 50-fold higher metastatic potential (Aceto N, Bardia A, Miyamoto D T, Donaldson M C, Wittner B S, Spencer J A et al (2014). Circulating tumor cell clusters are oligoclonal precursors of breast cancer metastasis. *Cell* 158: 1110-1122).

Using this imaging method in combination with human endothelial cells stably expressing the red fluorescent protein, mCherry, the ability of McTNs to promote the penetration of endothelial cell layers to contact the underlying substratum was described (Matrone, M. A., et al., *Cancer Res*, 2010. 70: 7737-41); (Whipple R A, Matrone M A, Cho E H, Balzer E M, Vitolo M I, Yoon J R et al (2010). Epithelial-to-mesenchymal transition promotes tubulin detyrosination and microtentacles that enhance endothelial engagement. *Cancer Res* 70: 8127-8137). (See FIG. 7). Interestingly, while selectin-mediated adhesion allows tumor cells to roll along blood vessel walls, only integrin-mediated adhesion with the underlying extracellular matrix allows tumor cells to arrest against the force of blood flow and extravasate successfully (Haier, J. and G. L. Nicolson, *Apmis*, 2001. 109: 241-62). These results add more support for a potential role of McTNs in the initial retention of CTCs in distant tissues (Balzer, E. M., et al., *Oncogene*, 2010. 29: 6402-8; Matrone, M. A., et al., *Oncogene*, 2010. 29: 3217-27; Korb, T., et al., *Exp Cell Res*, 2004. 299: 236-47).

Emerging evidence indicates the potential long-term danger of cytoskeletal cancer drugs that increase circulating tumor cells (Pachmann, K., et al., *J Clin Oncol*, 2008. 26: 1208-15; Hekimian, K., et al., *ISRN Oncol*, 2012.2012: 601810) or promote tumor stem cell characteristics (Balzer, E. M., et al., *Breast Cancer Res Treat*, 2010. 121: 65-78; Liu, X., et al., *Am J Pathol*, 2012. 180: 599-607; Suprynowicz, F. A., et al., *Proc Natl Acad Sci USA*, 2012. 109: 20035-40; Ohata, H., et al., *Cancer Res*, 2012. 72: 5101-10). These data emphasize the importance of developing rapid methods to define the mechanics and drug responses of tumor cells from individual patients so that cancer drugs aimed at tumor cell division or invasion do not inadvertently increase long-term metastasis.

Accordingly, there remains a need for methods, materials and devices for detecting microtentacles in primary tumor samples to improve prognosis and provide for more effective cancer treatments.

SUMMARY OF THE INVENTION

It is described herein that cells with metastatic potential, when freshly isolated from a solid tumor, generate long and dynamic microtubule-driven protrusions of the plasma membrane after dissociation and detachment referred to herein as microtentacles.

In one aspect, the present invention is directed to methods and compositions for detecting microtentacles in cellular samples to improve prognosis and provide for more effective cancer therapies by screening drugs for their ability to inhibit or promote microtentacle formation or stability. According to non-limiting example embodiments, in one aspect, the present invention provides a device for assaying living cells, comprising a substrate, wherein the substrate comprises one or more tethering molecules, which adhere to the substrate and are capable of interacting with cell membranes of the cells, wherein the cells maintain a free-floating, non-adherent character when bound to the one or more tethering molecules.

In some embodiments, the invention provides a device which tethers the membrane of living cells, such as tumor cells, to an imaging surface that is exceptionally thin (10 nm-100 nm) and optically clear. Tethered tumor cells continue to move dynamically as if they are free-floating, because the cell membrane is only held at a small point. In some embodiments, the invention enables a new microfluidic slide to capture and image microtentacles on patient tumor cells to determine their responses to cytoskeletal cancer drugs.

In some embodiments, the invention provides a perspective on how patient tumors respond to drug treatments (e.g., in less than 24 hours). In some embodiments, the invention tests FDA-approved drugs. The findings can be rapidly translated to clinical treatment. In some embodiments, the invention can establish which immediate microtentacles response of the tumor cells to drugs predict metastasis in mouse tumorgrafts (which is a known indicator of eventual patient metastasis). In some embodiments, the device provides a platform that can be used for testing patient tumors and to improve the understanding of how to select cancer therapies that reduce metastatic risk.

In some embodiments, the invention provides a microfluidic device to enable the rapid imaging of free-floating tumor cells removed from cancer patients (e.g., breast, prostate, colon, lymphoma, or other cancer types) during surgery or core needle biopsy, which provides an opportunity to advance clinical imaging of live patient tumor cells. In some embodiments, it can be demonstrated that the cytoskeletal dynamics and drug responses of free-floating tumor cells from cancer patients can be used as a rapid and early indicator of metastatic potential that can be used to guide therapy.

In some embodiments, the invention provides a new microfluidic device to tether fresh patient tumor cells to a patterned surface for microtentacle imaging with confocal microscopy. In some embodiments, the cell-tethering array slide will only require ~200 tumor cells or less from patients, an amount easily obtainable from surgical samples or even core needle biopsies. Moreover, this cell-tethering array will hold cells but prevent cell adherence to the surface so that the dynamic behavior of microtentacles continue.

In another embodiment, the invention provides a method of making a device for assaying living cells, comprising:
  i) coating a substrate with one or more layers of one or more materials that substantially inhibit the cells from adhering to the substrate; and
  ii) contacting the coated substrate with one or more tethering molecules, which adhere to the substrate and are capable of interacting with cell membranes of the cells, wherein the cells maintain a free-floating, non-adherent character when bound to the one or more tethering molecules.

In another embodiment, the invention provides methods to identify a patient with an increased likelihood of having or developing metastatic cancer. In some embodiments of the invention, tumor cells from a tumor or tumor biopsy removed from the patient are analyzed to determine whether the tumor cells, when dissociated from the tumor and detached from substrate, display microtentacles on their cell surface. The presence of microtentacles on the surface of the tumor cells identifies a patient with an increased likelihood of having or developing metastatic cancer.

The present invention also provides methods to rapidly determine how a patient's tumor will respond to various cancer drugs, by incubating the above-mentioned tumor cells with various cancer drugs while detached from substrate, to determine whether the drugs decrease the incidence of microtentacles on the surface of the tumor cells. In some embodiments, drugs that increase the number and/or length of microtentacles on the surface of the tumor cells should not be administered to the patient, whereas cells that decrease (or at least do not increase) the number and/or length of microtentacles on the surface of the tumor cells can be administered to the patient. In other embodiments, a therapy which increases microtentacles could be used in combination with a therapy that reduces microtentacles to counteract the detrimental effects of microtentacle promotion.

In another embodiment, the invention provides a method for imaging microtentacles on isolated, living primary tumor cells from a cancer subject, comprising:
i) obtaining one or more living primary tumor cells that has been isolated from a solid tumor from the subject;
ii) adding the one or more cells to a substrate of the device of the invention; and
iii) imaging the one or more living primary tumor cells and detecting the microtentacles, wherein the one or more tumor cells are non-adherently tethered to the substrate during imaging of the tumor cells.

In another embodiment, the invention provides a method of identifying a subject with an increased likelihood of having or developing metastatic cancer comprising:
i) obtaining one or more living primary tumor cells that has been isolated from a solid tumor from the subject;
ii) adding the one or more cells to a substrate of the device of the invention;
iii) imaging the one or more living primary tumor cells, wherein the one or more tumor cells are tethered to the substrate during imaging of the tumor cells; and
iv) scoring the one or more imaged cells for microtentacles to determine whether the subject has an increased likelihood of having or developing metastatic cancer.

In another embodiment, the invention provides a method for determining whether a candidate drug inhibits or promotes microtentacle formation and/or stability on isolated, living primary tumor cells from a cancer subject comprising:
i) obtaining one or more living primary tumor cells that has been isolated from a solid tumor from the subject;
ii) adding the one or more cells to a substrate of the device of the invention;
iii) contacting the one or more living primary tumor cells with the candidate drug;
iv) imaging the one or more living primary tumor cells treated with the candidate drug, wherein the one or more tumor cells are non-adherently tethered to the substrate during imaging of the tumor cells; and
v) scoring the one or more imaged cells for microtentacles to determine whether a candidate drug inhibits or promotes microtentacle formation and/or stability.

In another embodiment, the invention provides a method for determining the stem cell potential of tumor cells from a cancer subject comprising:
i) obtaining one or more living primary tumor cells that has been isolated from a solid tumor from the subject;
ii) adding the one or more cells to a substrate of the device of the invention;
iii) imaging the one or more living primary tumor cells, wherein the one or more tumor cells are non-adherently tethered to the substrate during imaging of the tumor cells; and
iv) scoring the one or more imaged cells for microtentacles to determine the stem cell potential of the tumor cell.

In another aspect, the invention provides a method for imaging microtentacles on isolated, living, non-adherent primary tumor cells from a cancer subject comprising:
i) obtaining one or more living, non-adherent primary tumor cells that has been isolated from a solid tumor from the subject; and
ii) imaging the one or more living, non-adherent primary tumor cells and detecting the microtentacles.

In another aspect, the invention provides a method of identifying a subject with an increased likelihood of having or developing metastatic cancer comprising:
i) obtaining one or more living non-adherent primary tumor cells that has been isolated from a solid tumor from the subject;
ii) imaging the one or more living, non-adherent primary tumor cells; and
iii) scoring the one or more imaged cells for microtentacles to determine whether the subject has an increased likelihood of having or developing metastatic cancer.

In another aspect, the invention provides a method for determining whether a candidate drug inhibits or promotes microtentacle formation and/or stability on isolated, living, non-adherent primary tumor cells from a cancer subject comprising:
i) obtaining one or more living, non-adherent primary tumor cells that has been isolated from a solid tumor from the subject;
ii) contacting the one or more living, non-adherent primary tumor cells with the candidate drug;
iii) imaging the one or more living, non-adherent primary tumor cells treated with the candidate drug; and
iv) scoring the one or more imaged cells for microtentacles to determine whether a candidate drug inhibits or promotes microtentacle formation and/or stability.

In another aspect, the invention provides a method for determining the stem cell potential of tumor cells from a cancer subject comprising:
i) obtaining one or more living, non-adherent primary tumor cells that has been isolated from a solid tumor from the subject;
ii) imaging the one or more living, non-adherent primary tumor cells; and
iii) scoring the one or more imaged cells for microtentacles to determine the stem cell potential of the tumor cell.

It is to be understood that both the foregoing general description and the following detailed description are exemplary, and thus do not restrict the scope of the invention. Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The skilled artisan will understand that the drawings, described below, are for illustration purposes only. The drawings are not intended to limit the scope of the present teachings in any way.

FIG. 13. McTNs in prostate tumor cell lines. LnCAP, DU145 and PC3 prostate tumor cells were imaged for McTNs with CellMask confocal microscopy (upper panels) or DIC brightfield microscopy (lower panels). Weakly metastatic LnCAP cells have a smooth surface and very few McTNs, while the more highly metastatic DU145 and PC3 cells have more McTNs. Automated McTN analysis and published stem cell markers in prostate cancer are shown for each cell line.

FIG. 40. Patterned arrays of tethered tumor cells facilitate imaging cell groups at high magnification without clustering (A), mechanical measurements (B) or systematic testing of cell-cell contact distance (C). In addition, the ability to track the fates of individual cells over time will allow us to determine if stem cells are selected or converted by drug treatments (D).

DETAILED DESCRIPTION

Figure 1:
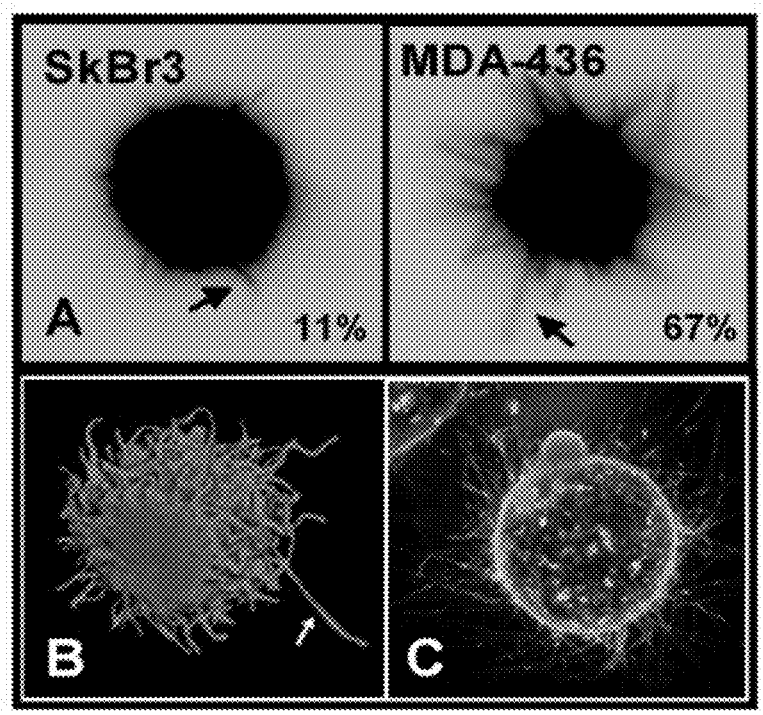
FIG. 1. Microtentacles in metastatic breast tumor cells. A) Human breast tumor cell lines transfected with membrane-localized green fluorescent protein (GFP) display protrusions when detached (black arrows, images inverted for contrast), that we have termed microtentacles (McTNs), due to a novel tubulin-based supporting mechanism. Cell lines with higher metastatic potential (MDA-436) show higher frequencies of McTNs when scored blindly for protrusions longer than the cell radius (Values=avg.±S.D. for 3 expts with at least 100 cells counted blindly). McTNs are only observed when cells are detached from extracellular matrix, regardless of method used (collagenase, trypsin, enzyme-free, scraping). Moreover, the delicate microtubule structure of McTNs causes them to collapse when treated with traditional fixatives (methanol, formaldehyde), which is a major reason why these structures were previously overlooked. Beyond GFP, we have used fluorescent staining methods with dyes based on cell surface glycosylation (B) or lipophilic membrane dyes (C) to resolve McTNs with live-cell confocal microscopy. Comparison with live cells allowed us to pioneer fixation methods that retain McTNs.
Figure 2:
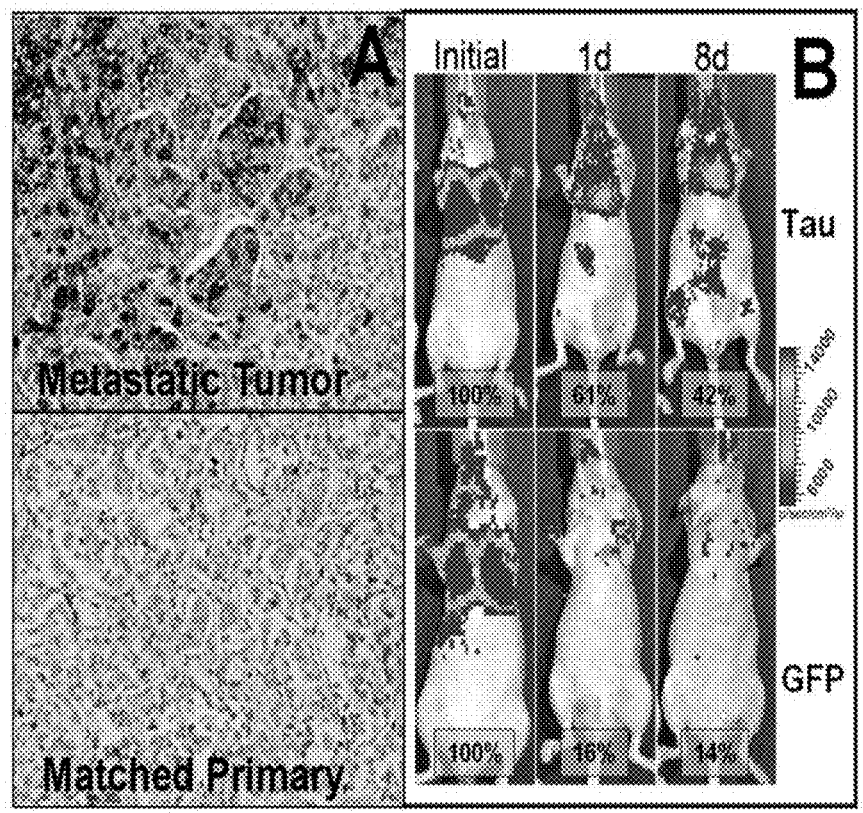
FIG. 2. The microtubule-stabilizing Tau protein is elevated in metastatic tumors and increases lung retention of injected tumor cells. A) Immunohistochemistry for expression of the Tau microtubule-stabilizing protein in 102 matched primary and metastatic tumors showed a specific upregulation of Tau in 53% of metastatic tumors, suggesting that microtubule stabilization provides a selective advantage to metastatic tumor cells. B) MCF7 human breast tumor cells were stably transfected with firefly luciferase and either Tau or the vector control containing GFP. Tail vein injection of $5 \times 10^5$ cells demonstrates equal initial lung retention, but after 1 or 8 days the MCF7 cells expressing Tau are retained more efficiently in the lung (values=avg. luminescence normalized to initial value for each mouse, n=6, P<0.05, t-test). These data demonstrate that genetically-induced microtubule stabilization that promotes McTNs can increase the ability of CTCs to reattach in distant tissues.
Figure 3:
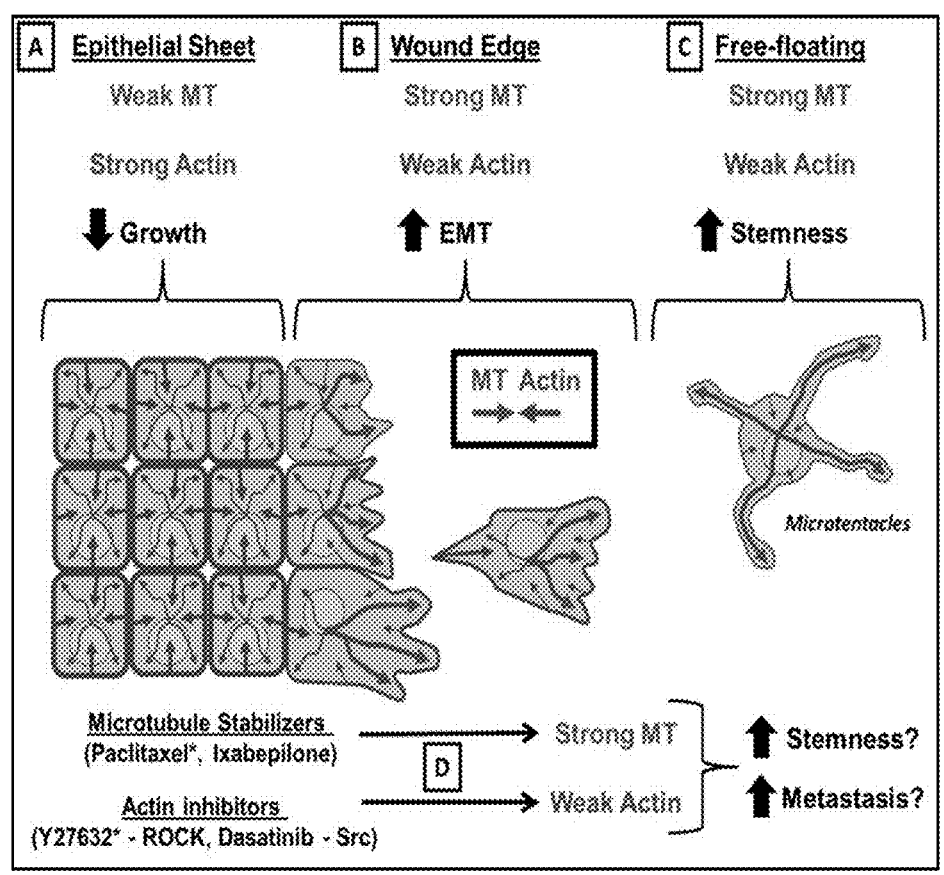
FIG. 3. Cancer drugs can mimic the cytoskeletal effects of wound healing and detachment. A) Epithelial cells within a barrier layer possess relatively weak microtubules expanding from the cell center that are counteracted by strong contraction of the actin filaments that form a cortical layer beneath the cell surface at cell-cell contacts. B) When an epithelial layer is scratched or wounded, cell-cell mediated actin contraction is reduced and microtubules become stabilized toward the wound, helping direct cells to reseal the epithelial barrier by moving into the wound. Epithelial cells at the wound edge also undergo an epithelial-to-mesenchymal transition (EMT) that induces increased stem cell characteristics. C) This wounding effect is even more pronounced when epithelial cells become fully detached (FIG. 3C), and the reinforcement of microtubules and weakening of actin yields unique microtentacles (McTNs) that promote epithelial cell aggregation and reattachment. This cytoskeletal imbalance response may explain why one of the most reliable ways to promote stem cell growth is floating culture. D) In support of this model, publications in the past year have shown that drugs which inhibit actin contraction or stabilize microtubules can directly induce stem cell characteristics (*).

The present invention generally concerns the previously unknown phenomenon that certain primary tumor cells isolated from a patient's solid tumor and placed under non-adherent in vitro culture conditions can generate microtubule protrusions that increase the cells' ability to reattach to each other and/or surfaces. Because tumor cells become detached during spread through the blood or lymphatics, the generation of these protrusions is important for the ability of the tumor cells to spread metastatically to distant tissues and/or organs. Thus, the ability of a tumor cell to form such microtubule protrusions is an indication of its metastatic potential. In vivo, such microtubule protrusions can act to enhance tumor cell adhesion to vessel walls and/or allow tumor cells to avoid being crushed by size-restriction in capillaries. These protrusions increase in number and size per cell in more metastatic tumor cell lines. Protrusions also occur with a significantly higher frequency in populations of breast tumor cells with greater metastatic potential. In particular, death of cancer patients is most often caused by metastatic spread of the primary tumor through the bloodstream. However, large tumor cells are efficiently killed by shearing when they are pushed through small-diameter capillaries by blood pressure. The microtubule protrusions can help metastatic tumor cells avoid death by adhering to vessel walls and/or bracing against them before the size of the capillary becomes limiting. Inhibition of the function of these microtubule protrusions and/or inhibition of their production, for example, allows metastatic tumor cells to have a greater opportunity to be efficiently killed, such as by shearing through capillary beds, for example. In specific embodiments, the invention focuses on the imaging and detection of these structures in living, non-adherent primary tumor cells isolated from a solid tumor from a cancer subject to improve prognosis and provide for more effective cancer treatments. In other embodiments, the invention relates to materials and devices that are useful for assaying living cells, such as tumor cells.

As provided herein, it has now been discovered that it is possible to immediately image microtentacles in tumor cells taken directly from tumors, from tumor cell biopsies or primary tumors surgically removed from cancer patients. Before the present invention, it was thought that tumor cells with microtentacles were present only as circulating tumor cells in the bloodstream of cancer patients having tumor metastases or at risk for metastases. The present discovery allows direct examination of cells from a primary tumor or surgical biopsy for the presence of microtentacles, which has various benefits that provide prognostic information and can guide patient treatment.

There are numerous advantages in some embodiments of the present invention. First, the present discovery provides an immediate functional phenotype to measure (as opposed to a static gene or protein expression profile). Second, the tumor cell imaging studies can be immediately conducted with very few cells. Because no long-term cell culturing is needed, the risk of in vitro selection for tumor cells with altered properties relative to the patient's original tumor cells is avoided. Third, the inventor has discovered that tumor stem cells are enriched in microtentacles at their cell surface. Thus, analysis of a patient's fresh tumor cells can provide an indication of a tumor's "stemness," which is known to be associated with an increased metastatic risk. Fourth, since microtentacle dynamics are very rapid, drug effects can be measured within minutes. Thus, the imaging of microtentacles on the surface of tumor cells taken from tumor biopsies or surgically-removed tumor specimens provides the opportunity to rapidly gauge a tumor's potential response to various cancer drugs prior to treatment, thereby allowing treatment to be tailored to the patient.

In some embodiments, the present invention further provides a new device (for example, a microfluidic cell tethering slide) to rapidly image cytoskeletal dynamics in freefloating patient tumor cells to better understand how individual patient tumors respond to cancer drugs. The device can also be used for research purposes on cultured cells. There are currently serious limitations in the ability to detect metastatic tumors in patients. Even the most sensitive clinical imaging methods (MRI/PET-CT) will not detect a tumor until it reaches a size of more than 10 million tumor cells. This means that doctors are currently unable to accurately follow early metastasis Importantly, since most cancer drug development and clinical trials are aimed at reducing the growth of these large tumors, very little is known about how current cancer therapies are influencing tumor metastasis. In addition, these imaging limitations make it very difficult to determine by imaging methods (such as MRI) if a tumor is shrinking because the tumor is dying or because it is scattering. These two scenarios have dramatically different implications for patients. This principle is particularly critical when patients are given drugs before surgery (neoadjuvant) since these patients already harbor tumors containing millions of cells and any inadvertent dissemination must be minimized.

References will now be made in detail to embodiments of the invention which, together with the drawings and the following examples, serve to explain the principles of the invention. These embodiments describe in sufficient detail to enable those skilled in the art to practice the invention, and it is understood that other embodiments may be utilized, and that structural, biological, and chemical changes may be made without departing from the spirit and scope of the present invention. Unless defined otherwise, all technical and scientific terms used herein have the same meanings as commonly understood by one of ordinary skill in the art.

For the purpose of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used). The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or openended and do not exclude additional, unrecited elements or method steps. Furthermore, where the description of one or more embodiments uses the term "comprising," those skilled in the art would understand that, in some specific instances, the embodiment or embodiments can be alternatively described using the language "consisting essentially of" and/or "consisting of." As used herein, the term "about" means at most plus or minus 10% of the numerical value of the number with which it is being used.

The term "microtentacles" as used herein refers to extensions of the plasma membrane in detached cells that are enriched in tubulin protein, for example Glu-tubulin or Ace-tubulin and largely devoid of polymerized actin. When treated with inhibitors of actin depolymerization, there is enhancement of the protrusions, such as with the protrusions increasing in length, number per cell and frequency in a population, for example. This is in contrast to well-known invadopodia and podosomes associated with adherent tumor cells that are actin-based and inhibited by actin depolymerization.

As used herein, "non-adherent" primary tumor cells are cells that have been isolated from a solid tumor by human intervention and placed under in vitro conditions in which the cells generally do not form significant protein-based contacts to an in vitro surface (such as that of a coated or uncoated cell culture chamber or microfluidic slide) during the time in which the tumor cells are being tested or studied, so as to allow the formation of microtentacles by the tumor cells capable of forming such microtentacles. Such "non-adherent" cells include cells that are tethered to the in vitro surface, e.g., by an oligonucleic acid tether or lipid tether as described herein.

As used herein, cells "isolated from a solid tumor" means cells are isolated from a solid tumor by human intervention and do not encompass detached cancer cells that have escaped their primary organ site, and are present elsewhere in the body of the patient, for example in the bloodstream or lymph nodes. The cells that are isolated from a solid tumor are primary cells, and do not encompass cells from cancer cell lines, which were originally derived from a solid tumor. In some embodiments, the cells are isolated directly from a non-removed tumor, from a tumor cell biopsy, from circulating tumor cells or from a tumor that is surgically removed. In some embodiments, the isolated cells are grown in mice (tumorgrafts, PDX) and then analyzed. In some embodiments, the isolated cells are cultured with conditional reprogramming and then analyzed.

In one embodiment, the invention provides a device for assaying living cells, comprising a substrate, wherein the substrate comprises one or more tethering molecules which adhere to the substrate and are capable of interacting with cell membranes of the cells, wherein the cells maintain a free-floating, non-adherent character when bound to the one or more tethering molecules.

In another embodiment, the invention provides a method of making a device for assaying living cells, comprising:
  i) coating a substrate with one or more layers of one or more materials that substantially inhibit the cells from adhering to the substrate; and
  ii) contacting the coated substrate with one or more tethering molecules which adhere to the substrate and are capable of interacting with cell membranes of the cells, wherein the cells maintain a free-floating, non-adherent character when bound to the one or more tethering molecules.

In some embodiments, the substrate is coated with one or more materials to minimize adhesion of cells or tissue to the substrate. In some embodiments, the materials are polymeric materials. In some embodiments the polymeric material is polyethylene oxide (PEO) and copolymers thereof. In some embodiments, the polymeric materials are selected from PEO-methacrylate-PVC copolymer and polyethylene oxide-polypropylene copolymers.

Figure 17:
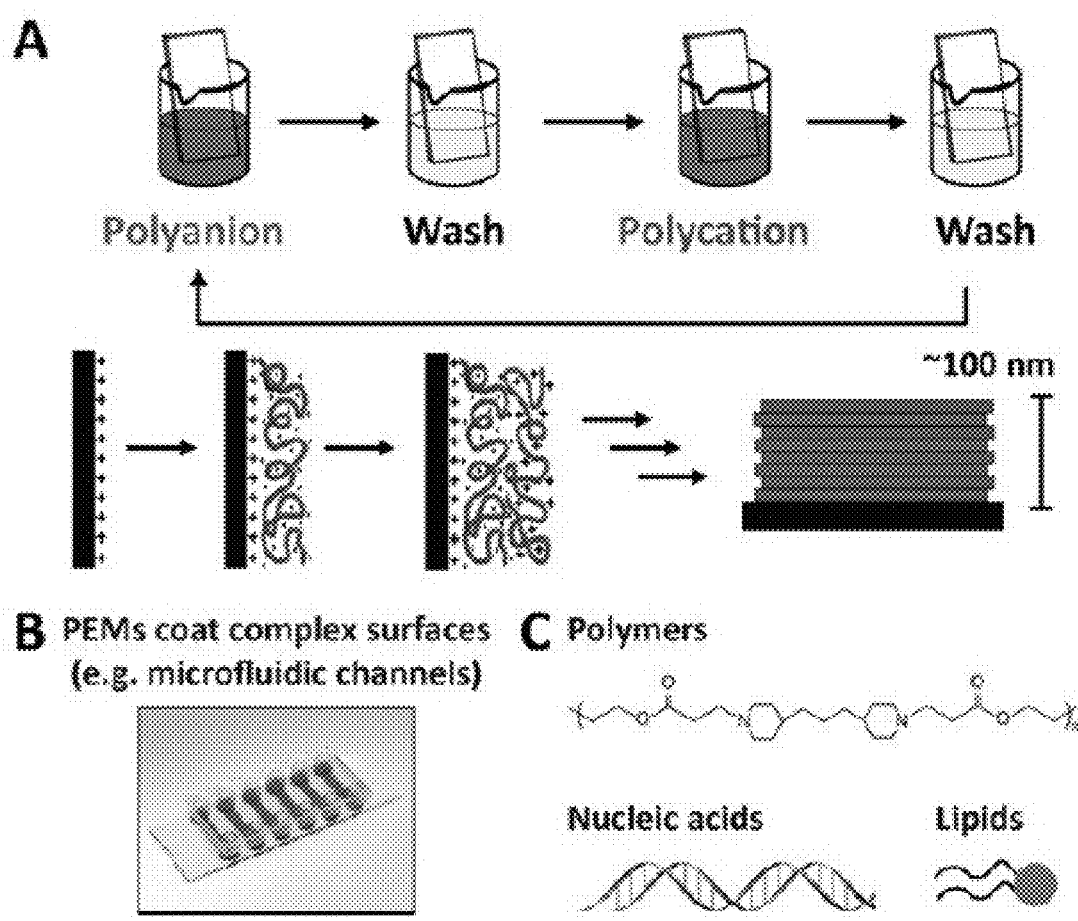
FIG. 17. Polyelectrolyte multilayer (PEM) films as ultra-thin surface coatings. A) Sequential exposure of surfaces to polycation and polyanion solutions generates multilayer films. B) PEMs can be deposited on complex geometries such as microfluidic channels. C) Coatings can be assembled from synthetic or natural components, allowing tuning of CTC adhesion by modifying PEMs with DNA or lipids.

In some embodiments, the polymeric materials are cationic and/or anionic polymers. In some embodiments, the substrate is coated with polyelectrolyte multilayer films (PEMs). Polyelectrolyte multilayer (PEM) films provide a tunable surface for tethering and imaging cells. Adsorption of alternating layers of polycationic and polyanionic solutions to surfaces can be used to generate polyelectrolyte multilayers (PEM) that assemble through electrostatic or hydrogen bonding (FIG. 17A). In some embodiments, these films are ultrathin (10-100 nm), optically clear, and use a simple all-aqueous approach based on sequential exposure of a target surface or substrate to the polyelectrolyte solutions. This feature allows simple deposition of films on complex surface geometries, including microfluidic channels (FIG. 17B). Furthermore, this platform allows assembly from a robust combination of synthetic polymers and biological molecules such as nucleic acids, lipids, proteins (FIG. 17C).

The term "electrolyte" as used herein means any chemical compound that ionizes when dissolved.

The term "polyelectrolyte" as used herein means a polymeric electrolyte, such as polyacrylic acid.

The term "multilayer" as used herein means a structure comprised of two or more layers.

In one embodiment of the present invention, polyelectrolyte films may be deposited on a surface, via the repetitive, sequential adsorption from aqueous solution of oppositely charged polyelectrolytes. In another embodiment, such films may be deposited on a surface via the repetitive, sequential adsorption from dilute aqueous solution of polymers, of which at least one polymer is a polyelectrolyte, comprising complementary hydrogen-bond donor functionality or hydrogen-bond acceptor functionality or both.

Any synthetic or natural polyion can be used to coat the substrate to create polyelectrolyte multilayer films (PEMs) using an aqueous based process. The resulting polyelectrolyte multilayers can coat substrates of any size or shape with defined properties of film thickness, composition, conformation, roughness, and wettability. In some embodiments, the layers can be deposited in a pH-dependent manner. See, e.g., WO 2003/035278 A1.

In some embodiments, PEMs are prepared by adsorption of alternating layers of polycationic and polyanionic aqueous solutions to the substrate that assemble through electrostatic or hydrogen bonding. Accordingly, some aspects of the methods for making the device of the invention comprise coating a substrate, comprising sequentially depositing on a substrate, alternating layers of polymers to provide a coated surface, wherein a first polymer is selected from one or more cationic polyelectrolytes and a second polymer is selected from one or more anionic polyelectrolytes, thereby preventing cell adhesion to said coated surface.

The cationic polymer material is not limiting. In some embodiments, the polycationic material can be any water-soluble polycationic polymer. Representative polycationic materials include natural and unnatural polyamino acids having net positive charge at neutral pH, positively charged polysaccharides, and positively charged synthetic polymers. Examples of suitable polycationic materials include polyamines having amine groups on either the polymer backbone or the polymer sidechains, such as poly-L-lysine and other positively charged polyamino acids of natural or synthetic amino acids or mixtures of amino acids, including poly(D-lysine), poly(ornithine), poly(arginine), and poly (histidine), and nonpeptide polyamines such as poly(aminostyrene), poly(aminoacrylate), poly(N-methyl aminoacrylate), poly(N-ethylaminoacrylate), poly(N,N-dimethyl aminoacrylate), poly(N,N-diethylaminoacrylate), poly(aminomethacrylate), poly(N-methyl aminomethacrylate), poly (N-ethyl aminomethacrylate), poly(N,N-dimethyl aminomethacrylate), poly(N,N-diethyl aminomethacrylate), poly(ethyleneimine), polymers of quaternary amines, such as poly(N,N,N-trimethylaminoacrylate chloride), poly(methyacrylamidopropyltrimethyl ammonium chloride), and natural or synthetic polysaccharides such as chitosan. In some embodiments, the polycationic material is used to form at least one of the multilayers. In some embodiments, the cationic polymer is polyallylamine hydrochloride (PAH). In some embodiments, the cationic polymer is polyacrylamide (PAAm).

The anionic polymer material is not limiting. In some embodiments, the polyanionic material can be any biocompatible water-soluble polyanionic polymer. Suitable materials include alginate, carrageenan, furcellaran, pectin, xanthan, hyaluronic acid, heparin, heparan sulfate, chondroitin sulfate, dermatan sulfate, dextran sulfate, poly(meth)acrylic acid, oxidized cellulose, carboxymethyl cellulose and crosmarmelose, synthetic polymers and copolymers containing pendant carboxyl groups, such as those containing maleic acid or fumaric acid in the backbone. Polyaminoacids of predominantly negative charge are also suitable. Examples of these materials include polyaspartic acid, polyglutamic acid, and copolymers thereof with other natural and unnatural amino acids. In some embodiments, the anionic polymer is polyacrylic acid (PAA). In some embodiments, the anionic polymer is polymethacrylic acid (PMA). In some embodiments, anionic polymer is poly(styrene sulfonate) (SPS).

This layer-by-layer deposition process provides a means to create polycation-polyanion polyelectrolyte multilayers one molecular layer at a time, thereby allowing control over the composition and surface functionality. Typically, alternate layers of positively and negatively charged polymers are sequentially adsorbed onto a substrate from dilute solution to build up interpenetrated multilayer structures.

In some embodiments, the PEMs comprise alternating layers of the cationic polymer polyacrylamide (PAAm) and the anionic polymer polymethacrylic acid (PMA). In some embodiments, the PEMs comprise alternating layers of poly-L-lysine (PLL) and poly-L-glutamic acid (PGA).

In some embodiments, the thickness of the coating is not limiting provided that it is effective to minimize adhesion of cells or tissue to the substrate. In some embodiments, the coating has a thickness that is less than 1 nm. In some embodiments, the thickness can range from about 1 nm to about 500 nm. In some embodiments, the thickness can range from about 1 nm to about 450 nm, from about 3 nm to about 250 nm, from about 5 nm to about 150 nm, from about 10 nm to about 100 nm, and from about 10 nm to about 50 nm. In one embodiment, the PEMs have a thickness of from about 10 nm to about 100 nm.

The number of bilayers of PEMs is also not limiting. In some embodiments, the substrate is coated with 1, 2, 3, 4, 5, 6, 7, 8, 9, 10, 11, 12, 13, 14, 15, 16, 17, 18, 19, 20, 21, 22, 23, 24, or 25 or more bilayers. In some embodiments, the substrate is coated with 1-10, 2-10, 2-6, or 3-5 bilayers.

In some embodiments, the thickness of the coating and number of layers of applied material is such that the coated substrate is substantially optically clear in order to enable visualization of the cells, e.g., using microscopy, such as confocal microscopy. In some embodiments, the optical clarity, defined by percent transmittance of light, is greater than about 70%. In some embodiments, the optical clarity is greater than about 75%, about 80%, about 85%, about 90%, about 91%, about 92%, about 93%, about 94%, about 95%, about 96%, about 97%, about 98%, about 99%, or about 100%.

The substrate of the device comprises one or more tethering molecules which adhere to the substrate and are capable of interacting with cell membranes of cells. In some embodiments, the device comprises PEMs that incorporate tethering molecules in their top surface. In some embodiments, the tethering molecules hold the cells in a substantially fixed position, so that the cells can be visualized by microscopy, such as confocal microscopy.

In some embodiments, the tether molecule is a hydrocarbon. In some embodiments, the tether molecule is a lipid. In some embodiments the tether molecule, such as a lipid, has a charged headgroup to support adherence to the substrate. In some embodiments, the interaction between the tether molecule and the substrate is an electrostatic interaction. In some embodiments, for efficient cell tethering, a lipid with long, hydrophobic fatty acids is required to associate with the cell membrane. In some embodiments, the lipid has at least 9 carbon atoms and is capable of associating with the plasma membrane of cells. In some embodiments, the lipid has at least 9, 10, 11, 12, 13, 14, 15, 16, 17, 18, 19, 20, 21, 22, 23, 24, 25, 26, 27, 28, 29 or 30 carbon atoms. In some embodiments, the lipid has from 9-25, 10-20, 12-19, or 13-18 carbon atoms. In some embodiments, the charged lipid can be added to the top layer of the coated substrate, such as the PEM film within a microfluidic channel slide.

Charged lipids that are suitable for use as tethers include, but are not limited to, glycerophospholipid, phospholipids, phosphatidylcholine, phosphatidic acid, lysophosphatidic acid, phosphatidylethanolamine, phosphatidylglycerol, phosphatidylserine, phosphatidylinositol, phosphatidylinositolphosphates, bis(monacylglycero)phosphate, 1,2-dioleoyl-3-trimethylammonium-propane (DOTAP), 1,2-dioleoyl-sn-glycero-3-phosphocholine (DOPC), 18:O-LysoPG and 15:O(3)-16:1-CA, salts and derivatives thereof. Suitable charged lipids are also commercially available (see Avanti Polar Lipids, Inc.). In some embodiments, the tether molecule is DOTAP.

Figure 21:
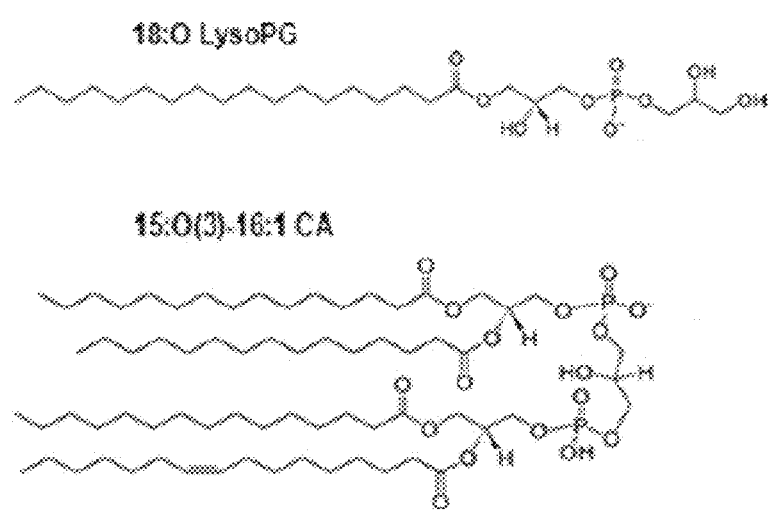
FIG. 21. Commercially-available glycerophospholipids (Avanti Polar Lipids, Inc.) for integration into a polyelectrolyte layer.

In some embodiments, a charged lipid, such as DOTAP is used as a tether on substrates comprising a PMA/PAAm bilayer. In some embodiments, a negatively or positively charged headgroup in the lipid can interact with the surface of the PMA/PAAm bilayer (FIG. 21). For example, a negatively charged phosphate in each glycerophospholipid can be used to interact with the positively charged amide group in the terminal PAAm layer of the PEM film. To optimize the lipid surface density and tune tumor cell adhesion, lipids can be prepared for adsorption using the lipid film rehydration technique. Briefly, different lipid ratios (1:10-10:1 LysoPG:CA) at total concentrations of 1-10 μmol of lipid can be dried under nitrogen, then sonicated (12 W, 30 sec) in 500 μL of HEPES. The PEM-coated surface or channel can then be exposed to the lipid solution for 5 minutes and washed twice.

In some embodiments, the tethering molecule, such as a charged lipid, is crosslinked to the substrate. The crosslinking agent that can be used is not limiting and can include chemical crosslinking agents or photo-crosslinking agents. Chemical crosslinking agents are well known and can include, for example, formaldehyde, ethylene glycol diacrylate, di(ethylene glycol) diacrylate, tetra(ethylene glycol) diacrylate, ethylene glycol dimethacrylate, di(ethylene glycol)dimethacrylate, tri(ethylene glycol)dimethacrylate, N,N'-Methylenebisacrylamide, N,N'-Methylenebisacrylamide, N,N'-(1,2-Dihydroxyethylene)bisacrylamide, N-(1-Hydroxy-2,2-dimethoxyethyl)acrylamide, and divinylbenzene.

Conjugation of a photo-cleavable charged group to the end of the tether molecule can generate a molecule that can be integrated in solution to the coated substrate. In some embodiments, the tether comprises a photoactivatable group that can be crosslinked to the substrate. In some embodiments the tether is crosslinked to reactive amines that are present on the substrate coating, such as PMA/PAAm bilayers.

In some embodiments, the tethering molecules are organized into an array pattern on the substrate. When the cells are bound, it will create an organized array of cells which will facilitate screening methods. In some embodiments, the tethering molecules are organized into an array pattern on the substrate, wherein the pattern array comprises islands of from about 4-15 μm in size with about 25-100 μm center spacing. In some embodiments, the tethering molecules are organized into an array pattern on the substrate, wherein the pattern array comprises islands of about 7 μm in size with about 40 μm center spacing.

In some embodiments, the tethering molecules are organized into an array pattern on the substrate by a process comprising microcontact printing. In some embodiments, an array of single-cell lipid attachment points can be made using a PDMS microcontact printing (μCP) procedure that patterns lipid on the upper PEM layer (e.g., PAAm or PLL) in small 5-10 μm spots (See Kohli et al., *J Colloid Interface Sci.* 301: 461-469 (2006)).

Figure 23:
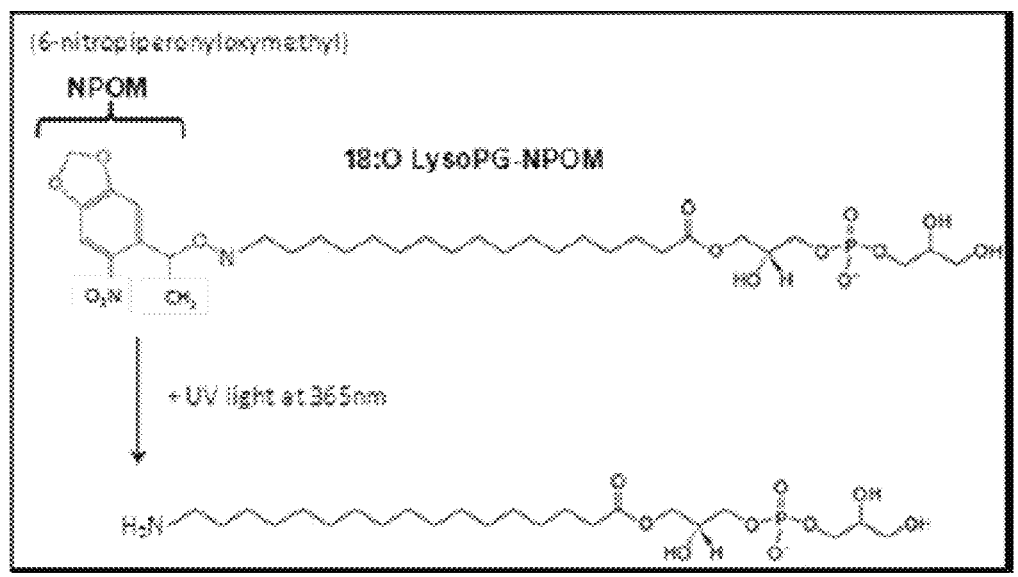
FIG. 23. Photoactivatable lipid anchor for lithography directly in microfluidic channels.
Figure 24:
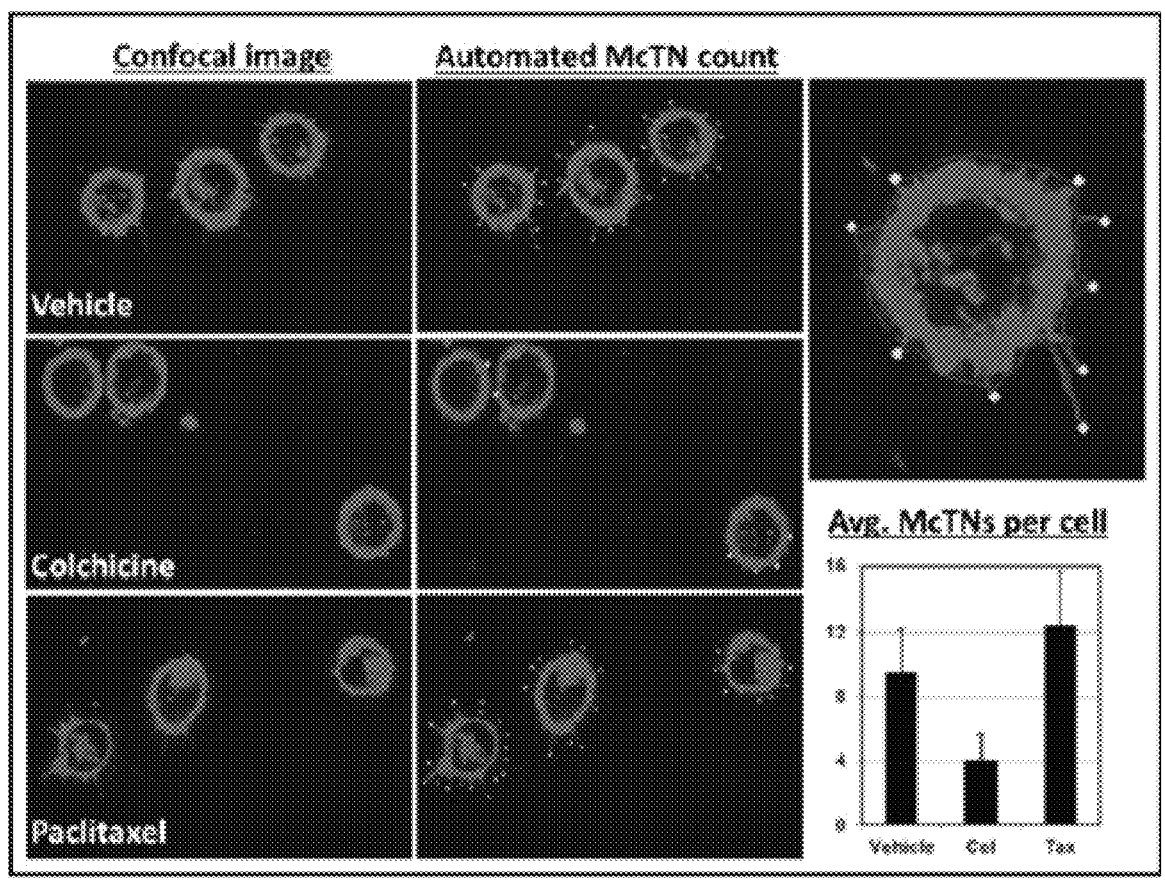
FIG. 24. Automated McTN analysis. MDA-436 cells were treated with vehicle (0.1% DMSO) or colchicine (50 μM) or paclitaxel (1 μM) and imaged for McTNs with confocal microscopy. A gradient vector flow snake algorithm was used to define the cell edges and a local curvature maxima effectively identified McTN ends (yellow diamonds). Quantitation of at least 10 random cells shows that Colchicine (Col) significantly reduces the average number of McTNs per cell, while paclitaxel (Tax) increases McTNs, but this does not reach significance in MDA-436 cells. This automated cell shape analysis will also enable calculations of average McTN length, curvature, etc. that will yield more multi-dimensional data for McTN studies.
Figure 39:
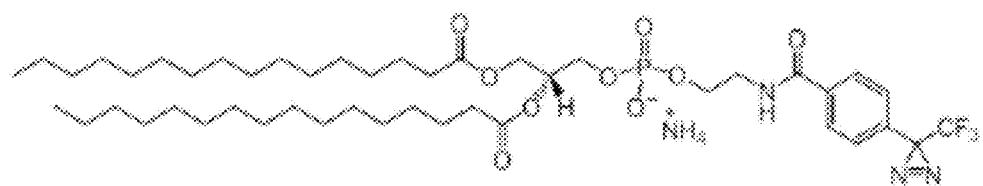
FIG. 39. Photo-crosslinkable custom lipid tether.

In some embodiments, the tethering molecules are organized into an array pattern on the substrate by a process comprising photo-crosslinking of the tether to the substrate at defined sites. In some embodiments, a lipid tether comprises an aryl azide group that can be photo-crosslinked to the substrate (FIG. 39). In some embodiments, the lipid tether comprises a 6-nitropiperonyloxymethyl (NPOM) group, which can be coupled to lipid via an amine linker and then cleaved through illumination with UV light at 365 nm (FIG. 23). The charges present on the NPOM can reduce hydrophobic interactions with the cell membrane.

In some embodiments, cells are added to the device and bound to the tethering molecules. The cells can also be fixed to the substrate prior to or following the analysis. In some embodiments, the cells are fixed with a chemical fixative, such as formaldehyde.

The properties or characteristics of the cells that can be assayed are not limiting. Once the cells have been added to the device, they can be assayed for one or more properties of interest. In some embodiments, the cells are assayed for the presence, size, stability, frequency, formation, and inhibition of microtentacles. In some embodiments, tumor cells are assayed for the presence of microtentacles, using one or more techniques such as confocal microscopy. In some embodiments, tumor cells are assayed for their responsiveness to drug treatment, including promotion or inhibition of microtentacles. In some embodiments, the stem cell potential of tumor cells from a cancer subject is assayed according to their ability to display microtentacles and/or form stem cell spheres. In some embodiments, the responses of tethered cells (e.g., formation of microtentacles/spheres) can be used to select optimal drug treatments. For example it may be desirable in some instances to promote more stem cell characteristics in certain cell types (e.g., wound healing, aging diseases, immunodeficiencies). In some embodiments, various cell types and drugs can be screened and selected that promote more stem cell characteristics such as increased microtentacles/spheres.

The cells that can be assayed are not limiting. In some embodiments, the cells are non-adherent cells. Various types of non-adherent cells are described in the literature and are well known. See, e.g., *J Immunol Methods.* 1983 Jul. 15; 61(2):145-50. In some embodiments, the cells to be assayed are selected from the group consisting of blood cells, bone marrow cells, lymph cells, stem cells, oocytes, muscle cells, epithelial cells and tumor cells.

In some embodiments the cells to be assayed are tumor cells. In some embodiments, the tumor cells are from a cancer selected from the group consisting of breast cancer, prostate cancer, lung cancer, bladder cancer, pancreatic cancer, brain cancer, liver cancer, testicular cancer, thyroid cancer, skin cancer, colon cancer, ovarian cancer, cervical cancer, and uterine cancer. In some embodiments, the tumor cells are primary tumor cells that have been isolated from a solid tumor from a subject. In some embodiments, the tumor cells are isolated directly from a non-removed tumor, from a tumor cell biopsy, from circulating tumor cells or from a tumor that is surgically removed. In some embodiments, the tumor cells comprise one or more microtentacles.

In some embodiments, the device is a microfluidic device. "Microfluidics" generally refers to systems, devices, and methods for processing small volumes of fluids. These types of systems and devices are well known in the art. Because microfluidic systems can process a wide variety of fluids, such as chemical or biological samples, these systems have many application areas, such as biochemical assays (for, e.g., medical diagnoses), biochemical sensors, etc. One type of microfluidic device is a microfluidic chip. Microfluidic chips can include micro-scale features (or "microfeatures"), such as channels, valves, pumps, and/or reservoirs for storing fluids, for routing fluids to and from various locations on the chip, and/or for reacting fluidic reagents. In some embodiments, microfluidic chips can include more complex micro-scale structures such as mixing devices or sensors for performing other processing functions on the fluids.

In some embodiments, the microfluidic device of the invention comprises one or more channels. In some embodiments, the device has 1, 2, 3, 4, 5, 6, 7, 8, 9, 10, 11, 12, 13, 14, 15, 16, 17, 18, 19, 20 or more channels. In some embodiments the substrate comprises a microfluidic slide or microfluidic channel. In some embodiments, the device is a microfluidic cell tethering slide that can be used to image live cells. In some embodiments, the device enables tethering of non-adherent cells to allow high-resolution imaging by confocal microscopy of microtentacles and measurement of time-dependent drug responses through media exchange. In some embodiments, the substrate is made of plastic or glass.

In some embodiments the device is a microfluidic slide having six channels. Shown in FIG. 17B is a microfluidic slide having six channels in accordance with some embodiments of the invention. In some embodiments, the substrate of the device comprises 2-10 alternating layers of PMA/PAAm and comprises DOTAP as the tether. In some embodiments, PEM films composed of PMA/PAAm can be deposited within the microfluidic channels of the device.

In another embodiment, the device is a microscope slide. In some embodiments, the device is a tissue culture plate or flask, such as a multi-well polystyrene tissue culture plate. The number of wells of the tissue culture plate can vary, and is not limiting. Microscope slides and tissue culture plates and flasks which can be adapted and modified for use in the claimed invention are available from commercial sources (e.g., Corning Inc., Sigma Aldrich).

In one embodiment, the invention provides a method for imaging microtentacles on isolated, living, non-adherent primary tumor cells from a cancer subject comprising:
 i) obtaining one or more living, non-adherent primary tumor cells that has been isolated from a solid tumor from the subject; and
 ii) imaging the one or more living, non-adherent primary tumor cells and detecting the microtentacles.

In another embodiment, the invention provides a method for imaging microtentacles on isolated, living primary tumor cells from a cancer subject, comprising:
 i) obtaining one or more living primary tumor cells that has been isolated from a solid tumor from the subject;
 ii) adding the one or more cells to the substrate of the device of the invention; and
 iii) imaging the one or more living primary tumor cells and detecting the microtentacles, wherein the one or more tumor cells are non-adherently tethered to the substrate during imaging of the tumor cells.

In another embodiment, the invention provides a method of identifying a subject with an increased likelihood of having or developing metastatic cancer comprising:
  i) obtaining one or more living, non-adherent primary tumor cells that has been isolated from a solid tumor from the subject;
  ii) imaging the one or more living, non-adherent primary tumor cells; and
  iii) scoring the one or more imaged cells for microtentacles to determine whether the subject has an increased likelihood of having or developing metastatic cancer.

In another embodiment, the invention provides a method of identifying a subject with an increased likelihood of having or developing metastatic cancer comprising:
  i) obtaining one or more living primary tumor cells that has been isolated from a solid tumor from the subject;
  ii) adding the one or more cells to the substrate of the device of the invention;
  iii) imaging the one or more living primary tumor cells, wherein the one or more tumor cells are non-adherently tethered to the substrate during imaging of the tumor cells; and
  iv) scoring the one or more imaged cells for microtentacles to determine whether the subject has an increased likelihood of having or developing metastatic cancer.

In some embodiments, the scoring comprises determining whether the one or more cells comprise two or more protrusions longer than the cell radius, wherein the one or more cells comprising two or more protrusions longer than the cell radius indicates an increased likelihood of having or developing metastatic cancer. See, e.g., Balzer, E. M., et al., *Oncogene*, 2010. 29: 6402-8; Whipple, R. A., et al., *Cancer Res*, 2010. 70: 8127-37; Balzer, E. M., et al., *Breast Cancer Res Treat*, 2010. 121: 65-78.

The present invention further comprises methods for identifying which candidate drugs should be administered to a cancer patient by assaying whether the drug inhibits, promotes and/or stabilizes the microtentacles. In some embodiments, drugs which stabilize or promote microtentacle formation should not be administered to patients whereas drugs which inhibit, destabilize or have no effect on microtentacles can be administered. These assays can comprise random screening of large libraries of candidate substances; alternatively, the assays may be used to focus on particular classes of compounds selected with an eye towards structural attributes that are believed to make them more likely to modulate the function of one or more microtubule protrusions or one or more components thereof.

In some embodiments, the invention provides a method for determining whether a candidate drug inhibits or promotes microtentacle formation and/or stability on isolated, living, non-adherent primary tumor cells from a cancer subject comprising:
  i) obtaining one or more living, non-adherent primary tumor cells that has been isolated from a solid tumor from the subject;
  ii) contacting the one or more living, non-adherent primary tumor cells with the candidate drug;
  iii) imaging the one or more living, non-adherent primary tumor cells treated with the candidate drug; and
  iv) scoring the one or more imaged cells for microtentacles to determine whether a candidate drug inhibits or promotes microtentacle formation and/or stability.

In another embodiment, the invention provides a method for determining whether a candidate drug inhibits or promotes microtentacle formation and/or stability on isolated, living primary tumor cells from a cancer subject comprising:
  i) obtaining one or more living primary tumor cells that has been isolated from a solid tumor from the subject;
  ii) adding the one or more cells to the substrate of the device of the invention;
  iii) contacting the one or more living, non-adherent primary tumor cells with the candidate drug;
  iv) imaging the one or more living, non-adherent primary tumor cells treated with the candidate drug, wherein the one or more tumor cells are non-adherently tethered to the substrate during imaging of the tumor cells; and
  v) scoring the one or more imaged cells for microtentacles to determine whether a candidate drug inhibits or promotes microtentacle formation and/or stability.

In some embodiments, the method further comprises administering an effective amount of the candidate drug to the subject to treat the cancer. In some embodiments, the candidate drug is administered if it inhibits microtentacle formation and/or stability or has no effect on microtentacles. In some embodiments, the subject is not administered an effective amount of the candidate drug if that drug promotes microtentacle formation and/or stability.

As used herein the term "candidate drug" refers to any molecule that may potentially inhibit or promote microtentacle formation and/or stability. The candidate drug is not limiting and can include a protein or fragment thereof, a small molecule, or even a nucleic acid molecule. In some embodiments, the candidate drug can include approved drugs currently used in cancer therapy, non-approved drugs, investigational compounds, and compounds from libraries which can be screened for activity.

In some embodiments, the candidate drug is selected from the group consisting of Abiraterone Acetate, Abitrexate (Methotrexate), Abraxane (Paclitaxel Albumin-stabilized Nanoparticle Formulation), ABVD, ABVE, ABVE-PC, AC, AC-T, Adcetris (Brentuximab Vedotin), ADE, Ado-Trastuzumab Emtansine, Adriamycin (Doxorubicin Hydrochloride), Adrucil (Fluorouracil), Afatinib Dimaleate, Afinitor (Everolimus), Aldara (Imiquimod), Aldesleukin, Alemtuzumab, Alimta (Pemetrexed Disodium), Aloxi (Palonosetron Hydrochloride), Ambochlorin (Chlorambucil), Amboclorin (Chlorambucil), Aminolevulinic Acid, Anastrozole, Aprepitant, Aredia (Pamidronate Disodium), Arimidex (Anastrozole), Aromasin (Exemestane), Arranon (Nelarabine), Arsenic Trioxide, Arzerra (Ofatumumab), Asparaginase Erwinia chrysanthemi, Avastin (Bevacizumab), Axitinib, Azacitidine, BEACOPP, Becenum (Carmustine), Beleodaq (Belinostat), Belinostat, Bendamustine Hydrochloride, BEP, Bevacizumab, Bexarotene, Bexxar (Tositumomab and I 131 Iodine Tositumomab), Bicalutamide, BiCNU (Carmustine), Bleomycin, Blinatumomab, Blincyto (Blinatumomab), Bortezomib, Bosulif (Bosutinib), Bosutinib, Brentuximab Vedotin, Busulfan, Busulfex (Busulfan), Cabazitaxel, Cabozantinib-S-Malate, CAF, Campath (Alemtuzumab), Camptosar (Irinotecan Hydrochloride), Capecitabine, CAPDX, Carboplatin, CARBOPLATIN-TAXOL, Carfilzomib, Carmubris (Carmustine), Carmustine, Carmustine Implant, Casodex (Bicalutamide), CeeNU (Lomustine) Ceritinib, Cerubidine (Daunorubicin Hydrochloride), Cervarix (Recombinant HPV Bivalent Vaccine), Cetuximab, Chlorambucil, CHLORAMBUCIL-PREDNISONE, CHOP, Cisplatin, Clafen (Cyclophosphamide), Clofarabine, Clofarex (Clofarabine), Clolar (Clofarabine), CMF, Cometriq (Cabozantinib-S-Malate), COPP, COPP-ABV, Cosmegen (Dactinomycin), Crizotinib, CVP, Cyclophosphamide, Cyfos (Ifosfamide), Cyramza (Ramucirumab), Cytarabine, Cytarabine, Liposomal, Cytosar-U (Cytarabine), Cytoxan (Cyclophosphamide), Dabrafenib, Dacarbazine, Dacogen (Decitabine), Dactinomycin, Dasatinib, Daunorubicin Hydrochloride, Decitabine, Degarelix, Denileukin Diftitox, Denosumab, DepoCyt (Liposomal Cytarabine), DepoFoam (Liposomal Cytarabine), Dexrazoxane Hydrochloride, Docetaxel, Doxil (Doxorubicin Hydrochloride Liposome), Doxorubicin Hydrochloride, Doxorubicin Hydrochloride Liposome, Dox-SL (Doxorubicin Hydrochloride Liposome), DTIC-Dome (Dacarbazine), Efudex (Fluorouracil), Elitek (Rasburicase), Ellence (Epirubicin Hydrochloride), Eloxatin (Oxaliplatin), Eltrombopag Olamine, Emend (Aprepitant), Enzalutamide, Epirubicin Hydrochloride, EPOCH, Erbitux (Cetuximab), Eribulin Mesylate, Erivedge (Vismodegib), Erlotinib Hydrochloride, Erwinaze (Asparaginase Erwinia chrysanthemi), Etopophos (Etoposide Phosphate), Etoposide, Etoposide Phosphate, Evacet (Doxorubicin Hydrochloride Liposome), Everolimus, Evista (Raloxifene Hydrochloride), Exemestane, Fareston (Toremifene), Faslodex (Fulvestrant), FEC, Femara (Letrozole), Filgrastim, Fludara (Fludarabine Phosphate), Fludarabine Phosphate, Fluoroplex (Fluorouracil), Fluorouracil, Folex (Methotrexate), Folex PFS (Methotrexate), FOLFIRI, FOLFIRI-BEVACIZUMAB, FOLFIRI-CETUXIMAB, FOLFIRINOX, FOLFOX, Folotyn (Pralatrexate), FU-LV, Fulvestrant, Gardasil (Recombinant HPV Quadrivalent Vaccine), Gardasil 9 (Recombinant HPV Nonavalent Vaccine), Gazyva (Obinutuzumab), Gefitinib, Gemcitabine Hydrochloride, GEMCITABINE-CISPLATIN, GEMCITABINE-OXALIPLATIN, Gemtuzumab Ozogamicin, Gemzar (Gemcitabine Hydrochloride), Gilotrif (Afatinib Dimaleate), Gleevec (Imatinib Mesylate), Gliadel (Carmustine Implant), Gliadel wafer (Carmustine Implant), Glucarpidase, Goserelin Acetate, Halaven (Eribulin Mesylate), Herceptin (Trastuzumab), HPV Bivalent Vaccine, Recombinant, HPV Nonavalent Vaccine, Recombinant, HPV Quadrivalent Vaccine, Recombinant, Hycamtin (Topotecan Hydrochloride), Hyper-CVAD, Ibrance (Palbociclib), Ibritumomab Tiuxetan, Ibrutinib, ICE, Iclusig (Ponatinib Hydrochloride), Idamycin (Idarubicin Hydrochloride), Idarubicin Hydrochloride, Idelalisib, Ifex (Ifosfamide), Ifosfamide, Ifosfamidum (Ifosfamide), Imatinib Mesylate, Imbruvica (Ibrutinib), Imiquimod, Inlyta (Axitinib), Intron A (Recombinant Interferon Alfa-2b), Iodine 131 Tositumomab and Tositumomab, Ipilimumab, Iressa (Gefitinib), Irinotecan Hydrochloride, Istodax (Romidepsin), Ixabepilone, Ixempra (Ixabepilone), Jakafi (Ruxolitinib Phosphate), Jevtana (Cabazitaxel), Kadcyla (Ado-Trastuzumab Emtansine), Keoxifene (Raloxifene Hydrochloride), Kepivance (Palifermin), Keytruda (Pembrolizumab), Kyprolis (Carfilzomib), Lanreotide Acetate, Lapatinib Ditosylate, Lenalidomide, Lenvatinib Mesylate, Lenvima (Lenvatinib Mesylate), Letrozole, Leucovorin Calcium, Leukeran (Chlorambucil), Leuprolide Acetate, Levulan (Aminolevulinic Acid), Linfolizin (Chlorambucil), LipoDox (Doxorubicin Hydrochloride Liposome), Liposomal Cytarabine, Lomustine, Lupron (Leuprolide Acetate), Lupron Depot (Leuprolide Acetate), Lupron Depot-Ped (Leuprolide Acetate), Lupron Depot-3 Month (Leuprolide Acetate), Lupron Depot-4 Month (Leuprolide Acetate), Lynparza (Olaparib), Marqibo (Vincristine Sulfate Liposome), Matulane (Procarbazine Hydrochloride), Mechlorethamine Hydrochloride, Megace (Megestrol Acetate), Megestrol Acetate, Mekinist (Trametinib), Mercaptopurine, Mesna, Mesnex (Mesna), Methazolastone (Temozolomide), Methotrexate, Methotrexate LPF (Methotrexate), Mexate (Methotrexate), Mexate-AQ (Methotrexate), Mitomycin C, Mitoxantrone Hydrochloride, Mitozytrex (Mitomycin C), MOPP, Mozobil (Plerixafor), Mustargen (Mechlorethamine Hydrochloride), Mutamycin (Mitomycin C), Myleran (Busulfan), Mylosar (Azacitidine), Mylotarg (Gemtuzumab Ozogamicin), Nanoparticle Paclitaxel (Paclitaxel Albumin-stabilized Nanoparticle Formulation), Navelbine (Vinorelbine Tartrate), Nelarabine, Neosar (Cyclophosphamide), Neupogen (Filgrastim), Nexavar (Sorafenib Tosylate), Nilotinib, Nivolumab, Nolvadex (Tamoxifen Citrate), Nplate (Romiplostim), Obinutuzumab, OEPA, Ofatumumab, OFF, Olaparib, Omacetaxine Mepesuccinate, Oncaspar (Pegaspargase), Ontak (Denileukin Diftitox), Opdivo (Nivolumab), OPPA, Oxaliplatin, Paclitaxel, Paclitaxel Albumin-stabilized Nanoparticle Formulation, PAD, Palbociclib, Palifermin, Palonosetron Hydrochloride, Pamidronate Disodium, Panitumumab, Paraplat (Carboplatin), Paraplatin (Carboplatin), Pazopanib Hydrochloride, Pegaspargase, Peginterferon Alfa-2b, PEG-Intron (Peginterferon Alfa-2b), Pembrolizumab, Pemetrexed Disodium, Perjeta (Pertuzumab), Pertuzumab, Platinol (Cisplatin), Platinol-AQ (Cisplatin), Plerixafor, Pomalidomide, Pomalyst (Pomalidomide), Ponatinib Hydrochloride, Pralatrexate, Prednisone, Procarbazine Hydrochloride, Proleukin (Aldesleukin), Prolia (Denosumab), Promacta (Eltrombopag Olamine), Provenge (Sipuleucel-T), Purinethol (Mercaptopurine), Purixan (Mercaptopurine), Radium 223 Dichloride, Raloxifene Hydrochloride, Ramucirumab, Rasburicase, R-CHOP, R-CVP, Recombinant Human Papillomavirus (HPV) Bivalent Vaccine, Recombinant Human Papillomavirus (HPV) Nonavalent Vaccine, Recombinant Human Papillomavirus (HPV) Quadrivalent Vaccine, Recombinant Interferon Alfa-2b, Regorafenib, R-EPOCH, Revlimid (Lenalidomide), Rheumatrex (Methotrexate), Rituxan (Rituximab), Rituximab, Romidepsin, Romiplostim, Rubidomycin (Daunorubicin Hydrochloride), Ruxolitinib Phosphate, Sclerosol Intrapleural Aerosol (Talc), Siltuximab, Sipuleucel-T, Somatuline Depot (Lanreotide Acetate), Sorafenib Tosylate, Sprycel (Dasatinib), STANFORD V, Sterile Talc Powder (Talc), Steritalc (Talc), Stivarga (Regorafenib), Sunitinib Malate, Sutent (Sunitinib Malate), Sylatron (Peginterferon Alfa-2b), Sylvant (Siltuximab), Synovir (Thalidomide), Synribo (Omacetaxine Mepesuccinate), TAC, Tafinlar (Dabrafenib), Talc, Tamoxifen Citrate, Tarabine PFS (Cytarabine), Tarceva (Erlotinib Hydrochloride), Targretin (Bexarotene), Tasigna (Nilotinib), Taxol (Paclitaxel), Taxotere (Docetaxel), Temodar (Temozolomide), Temozolomide, Temsirolimus, Thalidomide, Thalomid (Thalidomide), Thiotepa, Toposar (Etoposide), Topotecan Hydrochloride, Toremifene, Torisel (Temsirolimus), Tositumomab and I 131 Iodine Tositumomab, Totect (Dexrazoxane Hydrochloride), TPF, Trametinib, Trastuzumab, Treanda (Bendamustine Hydrochloride), Trisenox (Arsenic Trioxide), Tykerb (Lapatinib Ditosylate), Vandetanib, VAMP, Vectibix (Panitumumab), VeIP, Velban (Vinblastine Sulfate), Velcade (Bortezomib), Velsar (Vinblastine Sulfate), Vemurafenib, VePesid (Etoposide), Viadur (Leuprolide Acetate), Vidaza (Azacitidine), Vinblastine Sulfate, Vincasar PFS (Vincristine Sulfate), Vincristine Sulfate, Vincristine Sulfate Liposome, Vinorelbine Tartrate, VIP, Vismodegib, Voraxaze (Glucarpidase), Vorinostat, Votrient (Pazopanib Hydrochloride), Wellcovorin (Leucovorin Calcium), Xalkori (Crizotinib), Xeloda (Capecitabine), XELIRI, Xgeva (Denosumab), Xofigo (Radium 223 Dichloride), Xtandi (Enzalutamide), Yervoy (Ipilimumab), Zaltrap (Ziv-Aflibercept), Zelboraf (Vemurafenib), Zevalin (Ibritumomab Tiuxetan), Zinecard (Dexrazoxane Hydrochloride), Ziv-Aflibercept, Zoladex (Goserelin Acetate), Zoledronic Acid, Zolinza (Vorinostat), Zometa (Zoledronic Acid), Zydelig (Idelalisib), Zykadia (Ceritinib), and Zytiga (Abiraterone Acetate). In some embodiments, the drug is selected from the group consisting of Paclitaxel, Curcumin, Docetaxel, Ixabepilone, Vinblastine, Colchicine, Y-27632 Fasudil, SU6656 Dasatinib, HDAC inhibitors, ROCK inhibitors, Parthenolide, Costunolide and ML-7 Jazplakinolide. U.S. Pat. No. 8,193,238 also describes a number of compounds which have potential for inhibition of microtentacles which can be used in the present methods, the disclosure of which is incorporated by reference herein in its entirety.

In some embodiments, the method further comprises imaging one or more living, non-adherent primary tumor cells that have not been treated with the candidate drug and scoring the untreated cells for microtentacles, and comparing the score for untreated cells with the score obtained from step iv) for treated cells. In some embodiments, the treated and untreated cells are the same cells and the untreated cells are imaged and scored prior to step ii). In some embodiments, the scoring comprises determining whether the one or more cells comprise two or more protrusions longer than the cell radius. See, e.g., Whipple et al., *Experimental Cell Research* 313(7):1326-36 (2007). In some embodiments, the candidate drug promotes microtentacle formation and/or stability when the one or more cells exhibit a greater number of protrusions longer than the cell radius compared to untreated cells. In some embodiments, the candidate drug inhibits microtentacle formation and/or stability when the one or more cells exhibit a reduced number of protrusions longer than the cell radius compared to untreated cells.

In another embodiment, the invention provides a method for determining the stem cell potential of tumor cells from a cancer subject comprising:
 i) obtaining one or more living, non-adherent primary tumor cells that has been isolated from a solid tumor from the subject;
 ii) imaging the one or more living, non-adherent primary tumor cells; and
 iii) scoring the one or more imaged cells for microtentacles to determine the stem cell potential of the tumor cell.

In another embodiment, the invention provides a method for determining the stem cell potential of tumor cells from a cancer subject comprising:
 i) obtaining one or more living primary tumor cells that has been isolated from a solid tumor from the subject;
 ii) adding the one or more cells to the substrate of the device of the invention;
 iii) optionally treating the cells with a candidate drug;
 iv) imaging the one or more living primary tumor cells, wherein the one or more tumor cells are non-adherently tethered to the substrate during imaging of the tumor cells; and
 v) performing one or more of the following steps to determine the stem cell potential of the tumor cell:
  a. scoring the tethered cells for microtentacles;
  b. scoring tethered cells for their ability to form stem cell spheres; and
  c. tracking the fates of individual tethered cells to determine their ability to form stem cell spheres.

In some embodiments, the scoring comprises determining whether the one or more cells comprise two or more protrusions longer than the cell radius, wherein the one or more cells comprising two or more protrusions longer than the cell radius have a greater stem cell potential than cells having fewer than two protrusions longer than the cell radius.

The number of cells that can be isolated and assayed is not limiting. In some embodiments, fewer than 1000 cells are isolated and analyzed. In some embodiments, fewer than 200 cells are isolated and analyzed. In some embodiments, fewer than 50 cells are isolated and analyzed. In some embodiments, about 12 cells are isolated and analyzed. In some embodiments, at least one cell is isolated and analyzed. The cells can be isolated from surrounding cells and tissue to yield single-cell suspensions using standard techniques.

Surgical and needle biopsy samples provide a unique resource for early measurements of tumorigenic and metastatic potential in live tumor cells that is amenable to testing individual patient prognosis and drug responses without requiring long-term growth in cell culture. Culturing of patient-derived tumor cells can impose selective pressures that yield tumor cell populations which do not reflect the molecular characteristics of the patients' original tumors (DeRose, Y. S., et al., *Nat Med*, 2011. 17: 1514-20). In some embodiments, the invention allows a comprehensive mechanical analysis of free-floating (non-adherent), patient-derived tumor cells within hours or even minutes of their removal from the patient during surgery. In some embodiments, the methods of the invention can be applied on groups of fewer than 200 cells, which would allow their use from even core needle biopsy samples at the time of initial diagnosis. In some embodiments, the cells are freshly isolated from a solid tumor from the subject and the cells are dissociated and imaged for the microtentacles. In some embodiments, the cells are imaged within one week of isolation. In some embodiments, the cells are imaged within 48 hours of isolation, within 24 hours of isolation, within 12 hours of isolation, within 6 hours of isolation, within 2 hours of isolation and within 1 hour of isolation. In some embodiments, the cells have not undergone more than three doublings, more than two doublings, or more than a single doubling since isolation from the solid tumor.

The imaging the one or more living, non-adherent primary tumor cells is not limiting, provided, however, that the imaging allows for the detection of the microtentacles. In some embodiments, the cells are imaged using microscopy. In some embodiments, the cells are imaged by confocal microscopy. In some embodiments, the cells are imaged by flow cytometry image stream analysis (see, e.g., Imagestream by Amnis (Seattle, Wash.)). In some embodiments, one or more membrane markers are labeled to facilitate visualization of the plasma membrane and the microtentacles. In some embodiments, the plasma membrane is labeled with a fluorescent dye to visualize the microtentacles. In some embodiments, a lipophilic membrane dye (e.g., CellMask, 1:10,000, Invitrogen) can be added to the cells to facilitate membrane and microtentacle visualization of live cells. See, e.g., Charpentier et al., *Cancer Research* 15; 74(4):1250-60 (2014). In some embodiments, one or more other methods for surface labeling are employed, e.g., WGA (Balzer, E. M., et al., *Breast Cancer Res Treat*, 2010. 121: 65-78), GFP-membrane (Whipple et al., *Cancer Research* 68(14):5678-88 (2008); Whipple et al., *Cancer Res* 70:8127-37 (2010)) or microtubule visualization of microtentacles (Balzer et al., *Breast Cancer Res Treat* 121: 65-78 (2010)). Tumor cells that can be analyzed by the methods of the invention can be from any type of tumor in which microtentacle formation is involved in metastasis, for example, breast cancer, prostate cancer, lung cancer, bladder cancer, pancreatic cancer, brain cancer, liver cancer, testicular cancer, thyroid cancer, skin cancer, colon cancer, ovarian cancer, cervical cancer, and uterine cancer.

In some embodiments, the tumor cells are tethered to a substrate during imaging of the cell and microtentacles. The nature of the tethering of the cells to a substrate is not limiting provided that the cells maintain their free-floating, non-adherent character, and are able to form microtentacles. In some embodiments, the substrate is coated with one or more layers of one or more materials that substantially inhibit the cells from adhering to the substrate. In some embodiments, the substrate is coated with one or more polyelectrolytes. In some embodiments, the substrate is coated with polyelectrolyte multilayer films (PEMs) to coat the imaging surface to both prevent the formation of protein-based attachments and reduce cell displacement. In some embodiments, the PEMs are exceptionally thin (10-100 nm) and can incorporate tethering molecules in their top surface, such as DNA oligos or lipids that can interact with cell membranes and hold free-floating cells without allowing cell spreading. In some embodiments, microcontact printing (μCP) can be implemented to allow patterning of these attachment points. Tethered cells maintain the McTN dynamics and drug responses of free-floating cells, but can be held in an arrayed pattern for staining and high-resolution imaging. In some embodiments, the PEMs are prepared by adsorption of alternating layers of polycationic and polyanionic solutions to the substrate that assemble through electrostatic or hydrogen bonding (see FIG. 17A). In some embodiments, the films are ultrathin (10-100 nm), optically clear, and use a simple all-aqueous approach based on sequential exposure of a target surface or substrate to the polyelectrolyte solutions. In some embodiments, the PEMs are created on microfluidic slides or microfluidic channels (see FIG. 17B). In some embodiments, the PEMs are formed from a combination of polymethacrylic acid (PMA) and polyacrylamide (PAAm). In some embodiments, the PEMs comprise about 2-10 layers. PEMs are described in, e.g., Jewell et al., *Advanced drug delivery reviews* 60: 979-999 (2008); Jewell et al., *Biomacromolecules* 7: 2483-2491 (2006); Jewell et al., *Journal of Controlled Release* 106: 214-223 (2005)).

In some embodiments, the coated substrate is further coated with a tethering substance, which will adhere to the substrate and is capable of tethering the cell to the substrate and holding it in a substantially fixed position for imaging analysis. The tether is not limiting and can include any substance, such as proteins, lipids, nucleic acids, carbohydrates, aptamers, etc. In some embodiments, the tether is a lipid. In some embodiments, the tether is a charged lipid. In some embodiments, the tether is a glycerophospholipid. In some embodiments, the tether is selected from the group consisting of dotap (1,2-di-(9Z-octadecenoyl)-3-trimethylammonium-propane (chloride salt)), 18:O-LysoPG and 15:O(3)-16:1-CA.

In some embodiments, the cells are imaged while tethered to a microfluidic slide. In some embodiments, the microfluidic slide comprises a polyelectrolyte multilayer comprising a combination of polymethacrylic acid (PMA) and polyacrylamide (PAAm), and dotap as the tether. In some embodiments, the microfluidic slide can accommodate a sample volume of as little as 30 uL.

The present invention is further illustrated by the following Examples. These Examples are provided to aid in the understanding of the invention and are not to be construed as a limitation thereof.

EXAMPLES

Example 1

Figure 8:
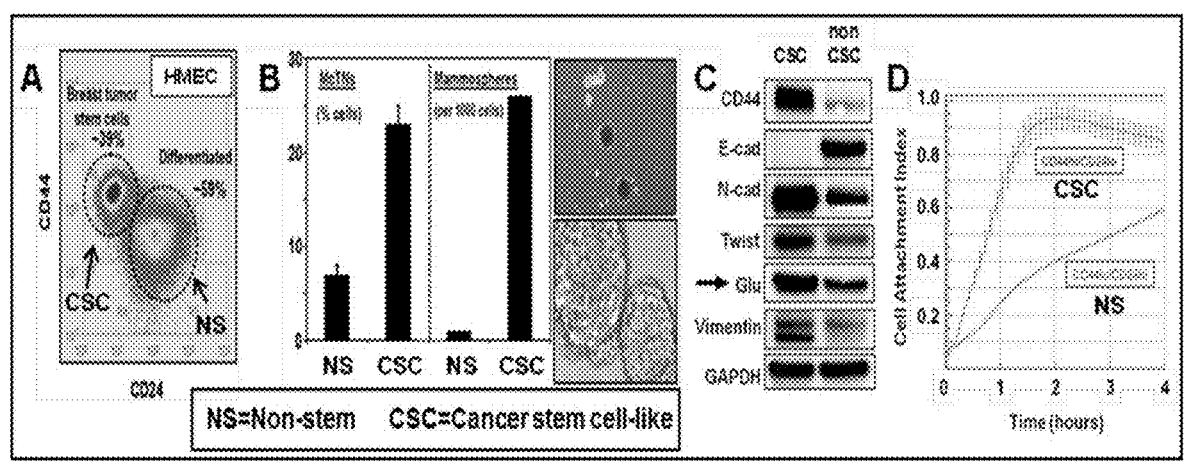
FIG. 8. Breast tumor stem cells have elevated microtentacles that promote reattachment. A) Flow cytometry sorting of immortalized human mammary epithelial (HMEC) cells for those that express high levels of CD44 and low levels of CD24 (CD44+/CD24−) isolates a stem cell population from breast tumor cell lines. B) McTNs and mammospheres are strongly upregulated in the CSC subpopulation. C) Likewise, EMT protein markers increase in the CSC population, including stabilized tubulin (Glu, arrow) and vimentin. D) Reflecting the elevated McTNs, the CSC population reattaches faster, when gauged by electrical impedance.

Rapid Characterization of Microtentacles on Patient Tumors with Live-Cell Confocal Microscopy McTNs on the surface of free-floating tumor cells serve as an indicator of their reattachment efficiency during experimental metastasis in vivo (Balzer, E. M., et al., *Oncogene*, 2010. 29: 6402-8; Matrone, M. A., et al., *Oncogene*, 2010. 29: 3217-27). In addition, our data now demonstrate that McTNs are a marker of increased stem cell characteristics (FIG. 8). Live-cell confocal microscopy can be used to examine McTN extension and dynamics in freshly-isolated tumor cells from cancer patients (such as those having breast cancer, prostate cancer, colon cancer, and other cancers as described herein) and relate McTN incidence and drug response to the tumorigenic and metastatic properties of parallel patient-derived tumorgrafts. Mechanical properties of the fresh tumor cells, tumorgraft-derived cells and fresh-frozen tissue can be compared to determine the durability of mechanical properties with different tumor banking techniques.

Example 2

Imaging of Microtentacles in Patient-Derived Tumor Cells with Live-Cell Confocal Microscopy For frozen or fresh tumor fragments, stromal matrix is digested with collagenase/hyaluronidase (12 h, 37° C.), and epithelial cell organoids are isolated from residual fat cells and lymphocytes by centrifugation (530×g, 5 min) (DeRose, Y. S., et al., *Curr Protoc Pharmacol*, 2013. Chapter 14: Unit14 23). Organoid pellets are washed with growth media (Hyclone DMEM/F12+HEPES, FBS, BSA, insulin, hydrocortisone) and subjected to cycles of centrifugation until the purity of epithelial organoids is confirmed (DeRose, Y. S., et al., *Curr Protoc Pharmacol*, 2013. Chapter 14: Unit 14 23). Organoids are dissociated with Trypsin/EDTA to yield a single-cell suspension of epithelial tumor cells. Half of this suspension is labeled with anti-CD45 (Alexa 648, Genetix) to exclude lymphocytes and anti-EpCAM (Alexa488, Miltenyi) to identify tumor cells. CellMask lipophilic membrane dye (1:10,000, Invitrogen) is added and live cells imaged on an Olympus FV-1000 confocal microscope (FIG. 9) with an incubated stage enclosure (Ibidi). Random fields totaling over 200 cells are blindly scored to determine the percentage of CD45−/EpCAM+ cells displaying two or more McTNs, according to our published methods (Balzer, E. M., et al., *Oncogene*, 2010. 29: 6402-8; Whipple, R. A., et al., *Cancer Res*, 2010. 70: 8127-37; Balzer, E. M., et al., *Breast Cancer Res Treat*, 2010. 121: 65-78; Vitolo, M. I., et al., *Oncogene*, 2012).

Figure 9:
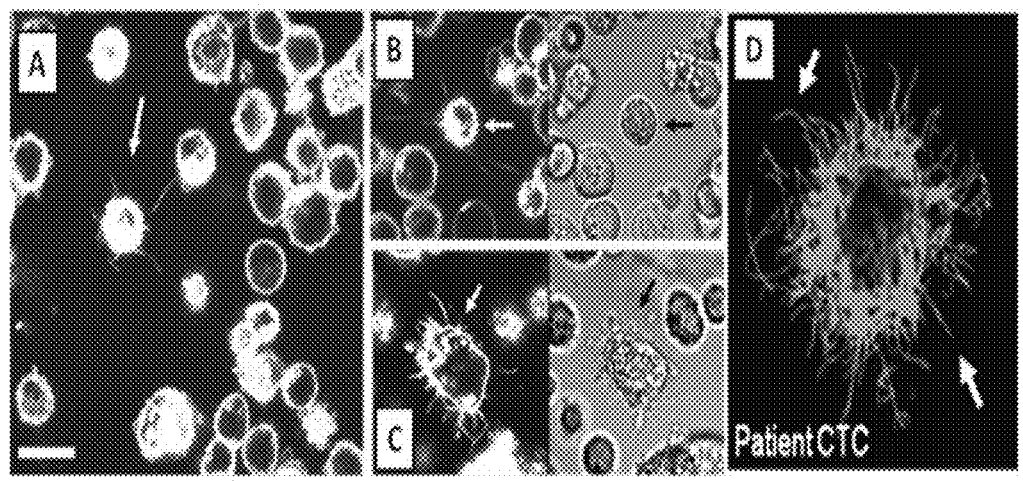
FIG. 9. Live patient tumor cells show evidence of McTNs. Epithelial organoids derived from patient breast tumors were dissociated and viewed live with confocal microscopy after membrane labeling with CellMask. Low (A) and high (B,C) magnification confocal images show evidence of McTNs (white arrows). Similarly, when EpCAM-isolated CTCs from patients are immunofluorescently stained for tubulin, microtentacle extension is also evident (D). McTNs on live patient cells.
Figure 10:
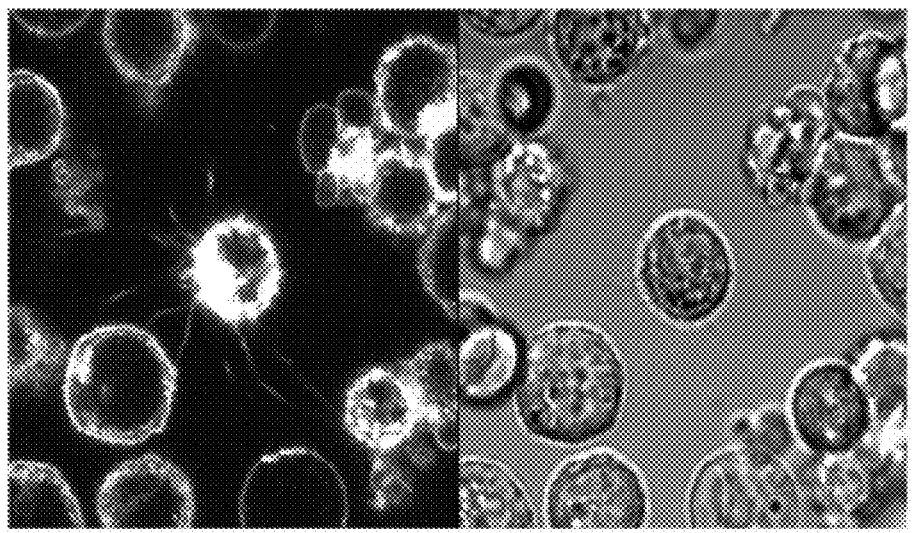
FIG. 10. Surgical samples from breast cancer patients (membrane dynamics—600×)
Figure 11:
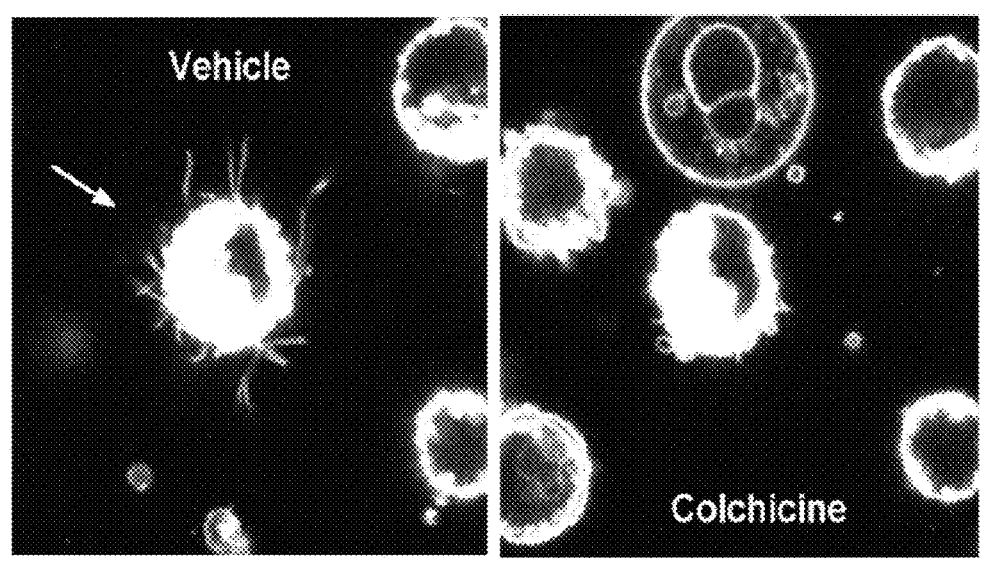
FIG. 11. Drug responses can be measured quickly in patient-derived tumor cells (30 minute Colchicine response)

McTNs are observed in live cells from patients as well as fixed cells that are purified by binding to anti-EpCAM antibodies (FIG. 9). Moreover, McTNs are enriched in the tumor cell subpopulation with increased cancer stem cell characteristics (FIG. 8). The CellMask method is currently the most effective for imaging live cells (Vitolo, M. I., et al., *Oncogene*, 2012), but numerous other methods for surface labeling WGA (Balzer, E. M., et al., *Breast Cancer Res Treat*, 2010. 121: 65-78), GFP-membrane (Whipple, R. A., et al., *Cancer Res*, 2010. 70: 8127-37)) or microtubule visualization of McTNs (Balzer, E. M., et al., *Breast Cancer Res Treat*, 2010. 121: 65-78) can be used as CellMask alternatives.

Example 3

Comparison of In Vitro McTN Counts with In Vivo Tumor Growth and Metastasis

In vitro McTN counts are a possible indicator of in vivo metastatic potential. This was first tested in cultured breast tumor cell lines (Whipple et al., *Cancer Research* 2008). In subsequent publications, two different genetic models were used to demonstrate that direct induction of McTNs through microtubule stabilization (Matrone et al, *Oncogene.* 2010 Jun. 3; 29(22):3217-27. doi: 10.1038/onc.2010.68. Epub 2010 Mar. 15) or actin disruption (Balzer et al., *Oncogene.* 2010 Dec. 2; 29(48):6402-8. doi: 10.1038/onc.2010.360. Epub 2010 Oct. 18) led to increased retention of circulating breast tumor cells in the lungs of living mice with bioluminescence imaging. More recently, it has also been shown that McTNs are increased in breast cancer stem cells (Charpentier et al., *Cancer Research,* 2014) revealing a possible connection between McTNs and the growth potential of breast tumors.

Advances in the analysis of patient-derived tumor cells (DeRose et al., *Nature Medicine,* 17(11): 1514-20. 2011) have now shown that direct transplant of fresh tumor fragments from breast cancer patients into the mammary gland of NOD/SCID immunodeficient mice allows the growth of patient-derived xenografts (PDX) that maintain important connections with the original cancer patient. First, the principal molecular markers (ER/PR/HER2) are retained in the PDX compared to the original patient. Second, while only approximately 40% of PDX grow in mice, this growth is prognostic for whether the patient is likely to have tumor recurrence. Third, the pattern of metastatic spread in the mice matches the original patient. For these principal reasons, PDX are currently considered an improved model of patient tumor cells than more traditional cultured cell lines.

As set forth herein, it is now demonstrated that McTNs are detectable in fresh patient tumor cells, within hours of when the patient cells are removed during surgery. To generate more patient-derived cells for analysis, patient cells have been propagated as PDX to retain the important connections to the original patient data (growth, metastasis, etc.).

Table 1 shows the lowest McTN frequencies are found in HCI-003 (ER+/PR+) and the non-metastatic PDX line (HCI-004). These patient profiles have better overall prognosis. The highest McTN counts are also found in those PDX that grow more rapidly (HCI-001, HCI-002), indicating a possible connection with increased stem cell characteristics in cells producing McTNs (Charpentier et al., *Cancer Research,* 2014). The increased McTN metrics that are enabled by the present invention through image analysis hold the potential to reveal more predictors of clinical outcome (McTN length, # per cell, curvature, motion, etc.).

More importantly, the present invention enables the rapid testing of patient tumor cells for responses to cancer drugs without requiring long-term growth. The cytoskeletal drug responses measured so far range from 5 minutes to 60 minutes treatment. The present invention therefore provides a method to determine how an individual patient's tumor cells respond to different cancer treatments, enabling a rapid and functional personalized medicine profile. The demonstration of McTNs in PDX cells allows application of these drug testing methods to freshly isolated patient cells, thereby allowing rapid tailoring of a patient's treatment regimen in accordance with the patient's microtentacle drug response profile.

Example 4

Examination of McTN and Stem Cell Responses of Patient-Derived Cells to FDA-Approved Drugs Patient-derived cells are treated with either vehicle (0.1% DMSO) or each of the drugs in Table 2 at the indicated concentration for 30 minutes and then analyzed for McTN incidence.

TABLE 2

List of cytoskeletal modulators. (FDA-approved*)

| Drugs | Conc. | Target | Effect | Predicted stemness & McTN effect |
| --- | --- | --- | --- | --- |
| Paclitaxel* | 1 µM | Micro-tubules | Stabilize | Increase |
| Docetaxel* | 0.2 µM | | | |
| Ixabepilone* | 0.2 µM | | | |
| Vinblastine* | 0.1 µM | Micro-tubules | Depolymerize | Decrease |
| Colchicine* | 50 µM | | | |
| Y-27632 | 30 µM | Acto-myosin | Weaken | Increase |
| Fasudil* | 50 µM | (ROCK) | | |
| SU6656 | 10 µM | Acto-myosin | Weaken | Increase |
| Dasatinib* | 3 µM | (Src) | | |
| ML-7 | 30 µM | Acto-myosin | Strengthen | Decrease |
| Jazplakinolide | 0.5 µM | | | |
| Parthenolide | 10 µM | Glu- | Reduce | Decrease |
| Costunolide | 10 µM | microtubules | | |

Example 5

Applying the Molecular Understanding of Breast Tumor McTNs to Prostate Cancer Cells The following Example leverages the understanding of the biochemical and biophysical mechanisms underlying McTNs (Balzer et al., *Oncogene.* 2010; 29(48):6402-8;

TABLE 1

List of current human patient-derived xenografts (pdx)

| Cell ID# | ER | PR | HER2 | Metastasis | Initial Growth (time to 0.1 cm$^3$) | Patient race | McTNs (% cells) |
| --- | --- | --- | --- | --- | --- | --- | --- |
| HCI-001 | − | − | − | Lung, LN | 4 weeks | Caucasian | 31 ± 3 |
| HCI-002 | − | − | − | LN | 5 weeks | Caucasian | 21 ± 3 |
| HCI-003 | + | + | − | Lung, LN | 11 weeks | Caucasian | 5 ± 1 |
| HCI-004 | − | − | − | None detected | 21 weeks | Caucasian | 10 ± 2 |
| HCI-005 | + | + | + | Lung, bone | 13 weeks | Caucasian | 17 ± 2 |
| HCI-011 | + | + | − | LN, pleura | 27 weeks | African-American | |

Whipple et al., *Cancer Research*. 2008; 68(14):5678-88; Whipple et al., *Experimental cell research*. 2007; 313(7): 1326-36. PubMed PMID: 17359970; Whipple et al., *Cancer Res*. 2010; 70(20):8127-37) and the advanced imaging methods we have developed (Whipple et al., *Cancer Res*. 2010; 70(20):8127-37; Balzer et al., *Breast Cancer Res Treat*. 2010; 121(1):65-78; Matrone et al., *Cancer Res*. 2010; 70(20):7737-41) to examine McTN generation in prostate cancer cells. A proposed wound healing model would predict that the cytoskeletal alterations that support McTNs would occur in many epithelial cancer cell types. Like breast cancer, prostate cancer predominantly arises from epithelial carcinomas (Birchmeier et al., *Acta Anat*. 1996; 156(3):217-26; Birchmeier W, Behrens J. Cadherin expression in carcinomas: role in the formation of cell junctions and the prevention of invasiveness. *Biochimica et biophysica acta*. 1994; 1198(1):11-26). Applying our McTN imaging methods to three commonly-used prostate cancer cell lines (LnCAP, DU145, PC3) (Kleeberger et al., *Cancer Res*. 2007; 67(19):9199-206; Windus et al., *Experimental cell research*. 2012; 318(19):2507-19) demonstrates that these cells form McTNs differentially (FIG. 13). The weakly metastatic LnCAP cell lines, which was derived from lymph node metastases demonstrates an exceptionally smooth surface, either with confocal or DIC microscopy. The more metastatic DU145 (brain met) or PC3 (bone met) cell lines have higher McTN incidences. Automated McTN analysis shows that McTN length is generally shorter in the prostate tumor cell lines compared to the HCI-001 breast tumorgraft line (compare FIGS. 12 and 13). While there is far less consensus in the prostate cancer field for effective markers of stem cell characteristics, numerous published measures show that LnCAP cells have lower stem cell markers than the DU145 and PC3 cells (Wang et al., *International journal of biological sciences*. 2013; 9(5):472-9; Bansal et al., *The Prostate*. 2014; 74(2):187-200; Hurt et al., *Br J Cancer*. 2008; 98(4): 756-65). As shown in FIG. 13, an integrated McTN score (frequency×length×#/cell) shows much higher values for DU145 (555.0) and PC3 (1054.5) compared to LnCAP (23.4).

In addition to breast cancer cells and prostate cancer cells, McTNs are also observed in other types of cancer cells, such as colon cancer cells and B-cell lymphoma cells (for example, in HCT-116 colon cancer cell lines and Jurkat B-cell lymphoma cell lines). McTNs are likely to be found on many different types of tumor cells with metastatic potential; accordingly, the present methods can be applied to any cancer in which tumor cells display microtentacles.

Example 6

Design of Nanoscale Surface Coatings to Capture, Study and Destroy Circulating Tumor Cells Microtentacles are plasma membrane extensions that occur only when tumor cells are unable to form protein-based attachments (such as when they are in the bloodstream during metastasis). McTNs enable circulating tumor cells to reattach in distant tissues during metastasis and are associated with more aggressive cancer phenotypes and stem cell characteristics.

However, such non-adherent cells can be challenging to image with advanced microscopy, since they continuously drift through the field of view. Attempting to exchange the surrounding media can displace nonadherent cells, greatly increasing the challenge of adding dyes or drugs to non-adherent cells. The current example uses polyelectrolyte multilayer films to coat the imaging surface to both prevent the formation of protein-based attachments and reduce cell displacement. This technology enables tethering of nonadherent tumor cells to allow high-resolution imaging of microtentacles and measurement of time-dependent drug responses through media exchange.

Provided is a microfluidic device to rapidly image cytoskeletal dynamics in free-floating patient tumor cells. There are currently serious limitations in the ability to detect metastatic breast tumors in patients. Even the most sensitive clinical imaging methods (MRI/PET-CT) will not detect a breast tumor until it reaches a size of more than 10 million tumor cells. This means that doctors are currently unable to accurately follow early metastasis Importantly, since most cancer drug development and clinical trials are aimed at reducing the growth of these large tumors, very little is known about how current cancer therapies are influencing tumor metastasis. In addition, these imaging limitations make it very difficult to determine by imaging methods (such as MRI) if a tumor is shrinking because the tumor is dying or because it is scattering. These two scenarios have dramatically different implications for patients. This principle is particularly critical when patients are given drugs before surgery (neoadjuvant) since these patients already harbor tumors containing millions of cells and any inadvertent dissemination must be minimized A new study that monitored circulating tumor cells (CTCs) during neoadjuvant chemotherapy showed that when CTCs increased during therapy (scattering model), there was a 25-fold higher risk of relapse in these patients within seven years. These findings emphasize that we need to improve the ability to measure early responses of patients' tumors to cancer drug treatment and understand potential impacts on metastasis.

In some aspects, the device uses either of two parallel PEM-based approaches (DNA or lipid) to tether tumor cells to an imaging surface while maintaining free-floating tumor cell behavior. The most effective strategy can be prioritized for the analysis of live tumor cells from 40 breast cancer patients. Parallel samples from these patients are transplanted orthotopically into immunodeficient mice. This tumorgraft approach has been demonstrated to recapitulate the metastatic behavior of the patient's original tumor far more faithfully than any tissue culture model. McTN characteristics (frequency, length, number per cell) and drug responses in individual patients can be compared to the molecular characteristics (ER/PR/HER2) of the original patient's tumor, as well as eventual growth and metastasis in the tumorgraft model.

The following experiments are conducted:
1. Develop non-adhesive PEM film with an integrated DNA oligo to tether free-floating tumor cells. Polyelectrolyte multilayers can form exceptionally thin films (10-100 nm) that prevent cell attachment while remaining optically clear (Sun B, Jewell C M, Fredin N J, Lynn D M (2007). Assembly of multilayered films using well-defined, end-labeled poly(acrylic acid): influence of molecular weight on exponential growth in a synthetic weak polyelectrolyte system. *Langmuir: the ACS journal of surfaces and colloids* 23: 8452-8459). Since PEM films can be formed simply through sequential exposure of solutions to the substrate (Jewell C M, Lynn D M (2008). Multilayered polyelectrolyte assemblies as platforms for the delivery of DNA and other nucleic acid-based therapeutics. *Advanced drug delivery reviews* 60: 979-999), we will coat microfluidic slides with a PEM that prevents tumor cell attachment to enable the study of free-floating cell behavior. To allow rapid fluorescent staining and drug treatments while maintaining this free-floating state, we will use an integrated DNA oligo to tether the tumor cell membrane to a PEM film (Selden N S, Todhunter M E, Jee N Y, Liu J S, Broaders K E, Gartner Z J (2012). Chemically programmed cell adhesion with membrane-anchored oligonucleotides. *Journal of the American Chemical Society* 134: 765-768).

a) Test PEM film composition to inhibit attachment in a wide variety of breast tumor cell lines (10 lines).

b) Validate PEM-mediated attachment inhibition with patient-derived cells (fresh surgical and tumorgraft).

c) Integrate a DNA oligo for membrane tethering into the upper layer of the PEM surface.

2. Engineer a direct lipid anchor as an alternative label-free approach to tether tumor cells. This aim will generate precise 5-10 µm lipid points of attachment to tether cells without requiring the addition of transient membrane surface labels to tumor cells (i.e., DNA). Bypassing DNA-labeling will allow direct application of clinical samples to the tethering array with dramatically reduced cell numbers compared to the requirements for DNA labeling (~$10^7$ cells/ml) (Selden N S, Todhunter M E, Jee N Y, Liu J S, Broaders K E, Gartner Z J (2012). Chemically programmed cell adhesion with membrane-anchored oligonucleotides. *Journal of the American Chemical Society* 134: 765-768). This one-step lipid array will also reduce the number of cells needed from patient samples because the entire volume of the microfluidic channel is 30 µL, allowing viewing of all patient cells in a single channel. Initial tests with breast tumor cell lines show that reproducible McTN counts can be obtained from as few as 200 cells per channel, increasing the feasibility that this analysis could even be conducted on core needle biopsy samples, which routinely yield between 2,000 and 10,000 tumor cells (Stoler D L, Stewart C C, Stomper P C (2002). Breast epithelium procurement from stereotactic core biopsy washings: flow cytometry-sorted cell count analysis. *Clin Cancer Res* 8: 428-432).

a) Design lipid tethers for cells without use of DNA oligos or other additives (label-free).

b) Use microcontact printing (µCP) to generate lipid islands of 5-10 µm in diameter for single-cell tethering.

c) Develop photoactivatable lipid anchor for lithography directly in microfluidic channels.

3. Analyze patient tumor cell microtentacles and drug responses and relate to tumorgraft outcome.

The most effective PEM microfluidic device (DNA or Lipid) will be prioritized to analyze microtentacles on freshly-derived tumor cells from 40 patients and their responses to 6 common and emerging cytoskeletal cancer drugs that either increase microtubule stabilization and McTNs (Paclitaxel, Ixabepilone) or decrease microtubule stabilization and McTNs (Colchicine, Parthenolide, Vinblastine, Curcumin).

a) Determine efficiency of 2 PEM devices (DNA or lipid) for tethering patient-derived tumorgraft cells.

b) Expand analysis with prioritized device to 40 patients for McTN analysis and drug response studies.

c) Compare tumorgraft outcome (growth rate, metastasis and organ of colonization) to live-cell data from fresh-patient samples and tumorgrafts (McTN metrics and drug responses).

Research Strategy

1. Develop Non-Adhesive PEM Film with Integrated DNA Oligo to Tether Free-Floating Tumor Cells.

Figure 18:
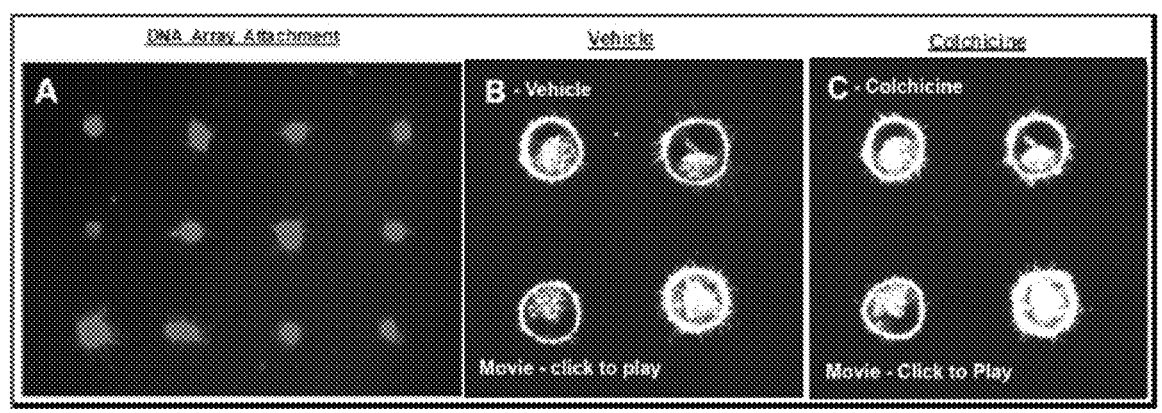
FIG. 18. DNA-lipid tethering of breast tumor cells maintains free-floating cell behavior. A) The DNA labeling technique can be used to pattern CTCs on planar surfaces), creating a platform to monitor McTN dynamics in arrayed cells (B) and the impact of drug exposure (C) in real-time.

It is possible to tether breast tumor cells to surfaces using a DNA-lipid anchor (FIG. 18).

Such tethered cells can be attached in specific patterns and maintain the dynamic behavior of free-floating tumor cells, including McTN formation. In addition, solutions can be passed over the cells to allow cell surface staining and the application of drugs without significantly disrupting cell tethering or displacing cells.

Building on our expertise and the PEM literature (Yang S Y, Mendelsohn J D, Rubner M F (2003). New class of ultrathin, highly cell-adhesion-resistant polyelectrolyte multilayers with micropatterning capabilities. *Biomacromolecules* 4: 987-994; Kohli N, Vaidya S, Ofoli R Y, Worden R M, Lee I (2006). Arrays of lipid bilayers and liposomes on patterned polyelectrolyte templates. *J Colloid Interface Sci* 301: 461-469), we have designed and tested 6 PEM bilayer compositions to control breast tumor cell adhesion in both a high-McTN cell line (MDA-436) and one with fewer McTNs (MCF-7). PEMs formed from a combination of polymethacrylic acid (PMA) and polyacrylamide (PAAm) provided a weakly cytophillic surface that supported weak attachment of tumor cells (<5%) even after 4 hours of incubation (FIG. 19A). In comparison, in both cells line more than 80% of cells attached to an uncoated surface. Ellipsometry showed that the thickness of the PMA/PAAm layer was proportional to the number of layers deposited, ranging from 10 nm (1 bilayer) to 90 nm (8 bilayers). The optical clarity of the coatings remained close to 100%, irrespective of the number of layers. Simple application of the PMA/PAAm film to commercially-available microfluidic chips (FIG. 19B, Ibidi, u-slideVI0.4) prevented adhesion of MDA-436 and MCF-7 cells. The coatings also provided outstanding optical clarity for confocal microscopy imaging of McTNs, even allowing detailed observation of live cell-cell attachment with McTNs (FIG. 19C). Moreover, this was achievable with a very small sample volume (30 uL). In this experiment, we will combine PMA/PAAm PEMs with DNA-based tethering technology to develop a coating that can be applied to microfluidic channels to tether cells while maintaining free-floating cell behavior.

a) Test PEM Film Composition to Inhibit Attachment in a Wide Variety of Breast Tumor Cell Lines.

Strategy and Analysis: We have characterized 15 different breast cancer cell lines for McTNs (Balzer E M, Whipple R A, Thompson K, Boggs A E, Slovic J, Cho E H et al (2010). c-Src differentially regulates the functions of microtentacles and invadopodia. *Oncogene* 29: 6402-6408; Matrone M A, Whipple R A, Thompson K, Cho E H, Vitolo M I, Balzer E M et al (2010). Metastatic breast tumors express increased tau, which promotes microtentacle formation and the reattachment of detached breast tumor cells. *Oncogene* 29: 3217-3227; Whipple R A, Balzer E M, Cho E H, Matrone M A, Yoon J R, Martin S S (2008). Vimentin filaments support extension of tubulin-based microtentacles in detached breast tumor cells. Cancer Research 68: 5678-5688; Whipple R A, Matrone M A, Cho E H, Balzer E M, Vitolo M I, Yoon J R et al (2010). Epithelial-to-mesenchymal transition promotes tubulin detyrosination and microtentacles that enhance endothelial engagement. Cancer Res 70: 8127-8137; Charpentier M S, Whipple R A, Vitolo M I, Boggs A E, Slovic J, Thompson K N et al (2013). Curcumin targets breast cancer stem-like cells with microtentacles that persist in mammospheres and promote attachment. Cancer Res) and we will test the efficiency of a PMA/PAAm film to reduce cell attachment across this panel. Sequential exposure and washing will be used to apply 1, 4 or 8 bilayers PMA/PAAm film to the Ibidi slides, and suspensions of breast tumor cell lines (1000 cells in 30 uL complete growth media) will then be applied to the channels. Cell attachment will be gauged by microscopy at 30 minute intervals from 0-240 minutes. We will also investigate the material properties (e.g., stability, surface roughness) of the PEMs before and after cell incubation using atomic force microscopy and ellipsometry as we have published previously (Yang S Y, Mendelsohn J D, Rubner M F (2003). New class of ultrathin, highly cell-adhesion-resistant polyelectrolyte multilayers with micropatterning capabilities. *Biomacromolecules* 4: 987-994; Kohli N, Vaidya S, Ofoli R Y, Worden R M, Lee I (2006). Arrays of lipid bilayers and liposomes on patterned polyelectrolyte templates. *J Colloid Interface Sci* 301: 461-469).

Figure 19:
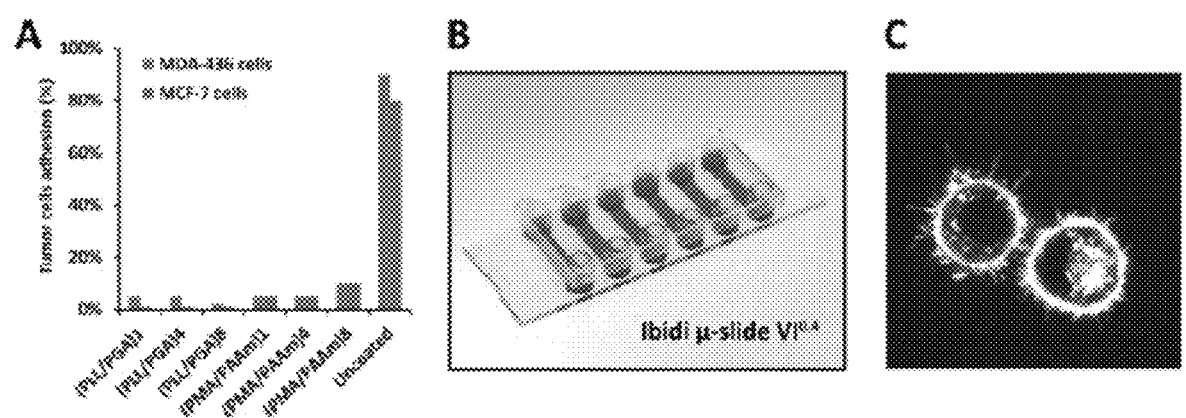
FIG. 19. PEM allows tuning of tumor cell adhesion and support maintenance of McTNs. A) Breast tumor cell lines incubated on PEM-coated surface adhere at differential levels depending on film composition and the number of bilayers deposited (i.e., film thickness). B) Films can be readily deposited on a commercially available microfluidic chamber used for direct visualization of (C) McTNs in live tumor cells.

PAAm is well-studied in terms of its ability to reduce cell attachment without causing cell toxicity and PMA is a key component of polyhydroxyethylmethacrylate (polyHEMA) that has been used widely to prevent cell attachment (Brouquet A, Taleb P, Lot A S, Beauchet A, Julie C, Prevost G et al (2011). A model of primary culture of colorectal cancer and liver metastasis to predict chemosensitivity. *The Journal of surgical research* 166: 247-254). For these reasons, we expect that this coating will be effective and non-toxic. To control for cytotoxicity, we will culture the 15 cell lines within the microfluidic slides for 3 days and gauge cell death by trypan blue exclusion. If the planned PMA/PAAm films allow attachment of more than 3 out of the 15 breast tumor cell lines within 240 minutes, or causes toxicity in more than 3 out of 15 cell lines over 3 days, we will test alternative surface compositions or increased numbers of layers. As shown in FIG. 19, we have already identified that PEMs composed of Poly-L-lysine (PLL) and Poly-L-Glutamic acid (PGA) have a very similar ability to prevent MDA-436 and MCF-7 attachment. We prioritized PMA/PAAm because PAAm has an amide side group that has many options for surface modification and cross-linking applications (Lakins J N, Chin A R, Weaver V M (2012). Exploring the link between human embryonic stem cell organization and fate using tension-calibrated extracellular matrix functionalized polyacrylamide gels. *Methods in molecular biology* 916: 317-350). PLL/PGA film can serve as an alternative.

b) Validate PEM-Mediated Attachment Inhibition with Patient-Derived Cells (Fresh Surgical and Tumorgraft).

Figure 20:
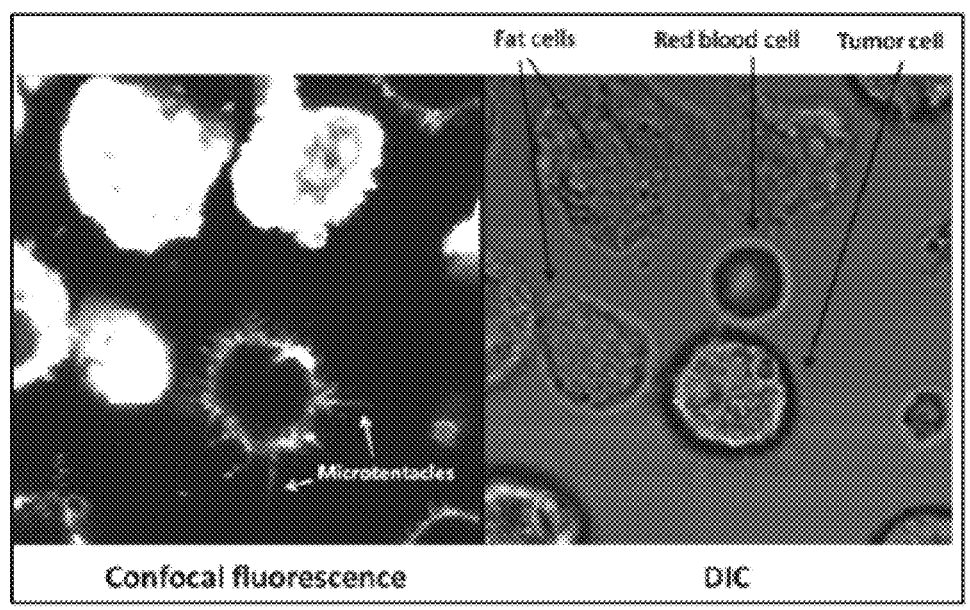
FIG. 20. Testing adhesion of patient-derived cell mixtures in microfluidic slides. Microtentacles are observable in patient tumor cells (arrows, left), but samples include non-tumor cell types (right).

Strategy and Analysis: Ibidi microfluidic slides coated with 2 PMA/PAAm films will be used to test the adhesion of more complex mixtures of patient-derived cells. Epithelial cell suspensions are purified by enzymatic digestion (collagenase/hyaluronidase) and differential centrifugation (DeRose Y S, Gligorich K M, Wang G, Georgelas A, Bowman P, Courdy S J et al (2013). Patient-derived models of human breast cancer: protocols for in vitro and in vivo applications in tumor biology and translational medicine. *Current protocols in pharmacology/editorial board, S J Enna Chapter* 14: Unit14 23) from either fresh patient tumor fragments or tumorgrafts that have been expanded through orthotopic transplant into the mammary glands of NOD/SCID mice (DeRose Y S, Wang G, Lin Y C, Bernard P S, Buys S S, Ebbert M T et al (2011). Tumor grafts derived from women with breast cancer authentically reflect tumor pathology, growth, metastasis and disease outcomes. *Nat Med* 17: 1514-1520). It is possible to generate 105-106 epithelial cells from these preparations (DeRose Y S, Gligorich K M, Wang G, Georgelas A, Bowman P, Courdy S J et al (2013). Patient-derived models of human breast cancer: protocols for in vitro and in vivo applications in tumor biology and translational medicine. *Current protocols in pharmacology*/editorial board, S J Enna Chapter 14: Unit14 23), but there is inevitably some contamination with other cell types, primarily fat cells and red blood cells (FIG. 20). To advance the PEM microfluidic approach to clinical application, we will need to ensure that these additional cell types do not obscure the observation of tumor cells by adhering to the surface. Independent preparations from 5 patients and the resulting tumorgrafts will therefore be tested for adhesion to PEM-coated channels over four hours.

To rigorously identify tumor cells, we will use a standard identification for circulating breast tumor cells to distinguish epithelial tumor cells (EpCAM+/CD45−) and lymphocytes (EpCAM−/CD45+) (Takao M, Takeda K (2011). Enumeration, characterization, and collection of intact circulating tumor cells by cross contamination-free flow cytometry. *Cytometry Part A: the journal of the International Society for Analytical Cytology* 79: 107-117). An independent double-positive stain for cytokeratins (CK8/CK18) (Stoler D L, Stewart C C, Stomper P C (2002). Breast epithelium procurement from stereotactic core biopsy washings: flow cytometry-sorted cell count analysis. *Clin Cancer Res* 8: 428-432) can also be used to identify breast tumor cells. Red blood cells are easily identifiable by their small size and concave morphology and fat cells stain very brightly with the lipophilic compound (CellMask) used to visualize microtentacles (FIG. 20, left panel), making it relatively simple to exclude these cell types during imaging.

c) Integrate a DNA Oligo for Membrane Tethering into the Upper PEM Surface.

Strategy and Analysis: Using published methods (Saurer E M, Jewell C M, Roenneburg D A, Bechler S L, Torrealba J R, Hacker T A et al (2013). Polyelectrolyte multilayers promote stent-mediated delivery of DNA to vascular tissue. *Biomacromolecules* 14: 1696-1704; Jewell C M, Zhang J, Fredin N J, Lynn D M (2005). Multilayered polyelectrolyte films promote the direct and localized delivery of DNA to cells. *Journal of controlled release*: official journal of the Controlled Release Society 106: 214-223; Flessner R M, Jewell C M, Anderson D G, Lynn D M (2011). Degradable polyelectrolyte multilayers that promote the release of siRNA. *Langmuir: the ACS journal of surfaces and colloids* 27: 7868-7876), a short DNA oligo (20 nts) will be electrostatically adsorbed to PEMs by incubation (30 µL, 0.2 mg/mL) over a PMA/PAAm film with a cationic capping layer of PAAm or the strong polycation, PLL. A lipid-coupled complementary DNA strand will be added to suspended MDA-436 and MCF-7 cells34 (Adheren, Inc.). Suspensions of 5,000 cells in 30 µL of PBS will then be applied to the channels and hybridized for 30 minutes with the complementary DNA displayed on the PEM-coated channel. The ability of cells to remain on the PEM-DNA surface will be tested by repeatedly washing the channel with 50 uL of media. The number of cells released will be measured by a Countess automated hemocytometer after each wash.

There may be potential complications if the electrostatic interaction of the charged DNA with the PEM layer is not sufficient to secure cells during the media exchanges. In this case, we will incorporate a strong polyelectrolyte (e.g., PDAC) as the "capping" layer or explore covalent linkage for the DNA to the PAAm, as published by others (Chippada U, Yurke B, Georges P C, Langrana N A (2009). A nonintrusive method of measuring the local mechanical properties of soft hydrogels using magnetic microneedles. Journal of biomechanical engineering 131: 021014).

2. Engineer a Direct Lipid Anchor as an Alternative Label-Free Approach to Tether Tumor Cells.

DNA-based cell tethering is certainly effective for McTN imaging in cultured cell lines. However, since this strategy requires very high concentrations of cells ($10^7$ cells/ml) for the initial DNA membrane labeling procedure (Selden N S, Todhunter M E, Jee N Y, Liu J S, Broaders K E, Gartner Z J (2012). Chemically programmed cell adhesion with membrane-anchored oligonucleotides. *Journal of the American Chemical Society* 134: 765-768), it would be advantageous to develop a more direct strategy for the analysis of clinical samples, where limited numbers of cells are available. In this aim, we will develop methods for the direct conjugation of membrane-tethering lipid to the top layer of the PEM film within the microfluidic channel slide. This also avoids the difficulties that arise during the DNA-tethering method when the DNA-lipid label is rapidly internalized into the target cells by membrane recycling, effectively reducing the tethering capability. Moreover, this lipid conjugation approach will remove any need to pre-label the cells applied to the attachment surface, since the interaction between the lipid-coated surface and the cell membrane will be direct.

a) Design Lipid Tethers to Support McTNs on Cells without Use of DNA Oligos or Other Additives (Label-Free).

Strategy and Analysis: For efficient cell tethering, a lipid with long, hydrophobic fatty acids is required to associate with the membrane. The ideal molecule would also have a charged headgroup to support PEM adsorption. Using these constraints, we have prioritized the following two commercially-available glycerophospholipids (Avanti Polar Lipids, Inc.) for integration into our PMA/PAAm bilayer (FIG. 21). The negatively charged phosphate in each glycerophospholipid can be used to interact with the positively charged amide group in the terminal PAAm layer of the PEM film. To optimize the lipid surface density and tune tumor cell adhesion, lipids will be prepared for adsorption using the lipid film rehydration technique. Briefly, different lipid ratios (1:10-10:1 LysoPG:CA) at total concentrations of 1-10 μmol of lipid will be dried under nitrogen, then sonicated (12 W, 30 sec) in 500 μL of HEPES. The PEM-coated surface or channel will then be exposed to the lipid solution for 5 minutes and washed twice.

Since the tethering of the cells to the surface will be direct, it will be important to control the seeding cell density to avoid overcrowding the imaging area. Our initial tests show that the dimensions of our microfluidic channel (14 mm×3.8 mm×0.2 mm height) allows for an even distribution of approximately 5,000 to 20,000 cells. Higher densities lead to rapid cell-cell clustering without a tethering method to keep cells from drifting into each other. The major potential complication we foresee with the lipid method is that our primary fluorescent labeling method is based on a lipophilic cell membrane dye, which may also bind to lipids conjugated to the channel surface and generate high fluorescence background. There are several strategies that we can use to overcome this challenge. First, confocal microscopy excludes the out-of-focus light, so increased labeling at the attachment surface will not prevent us from imaging the center plane of the cells with low background. We currently use this strategy, since a low concentration of the membrane dye (CellMaskOrange, 1:20,000) is left on the cells during imaging, and confocal imaging allows exclusion of background and high-resolution imaging of the membrane. If the background signal remains too high, there are several other membrane dyes that could be used (DiI, DiO), but might present similar difficulties. In the case that all lipophilic dyes are ineffective for this reason, we can also stain live cells with a fluorescent wheat-germ agglutinin (Alexa594-WGA) which binds glycosylated residues on the cell membrane rather than through lipid affinity and labels McTNs efficiently (FIG. 1B, arrow).

b) Use μCP to Generate Lipid Islands of 5-10 μm in Diameter for Single-Cell Tethering.

Figure 22:
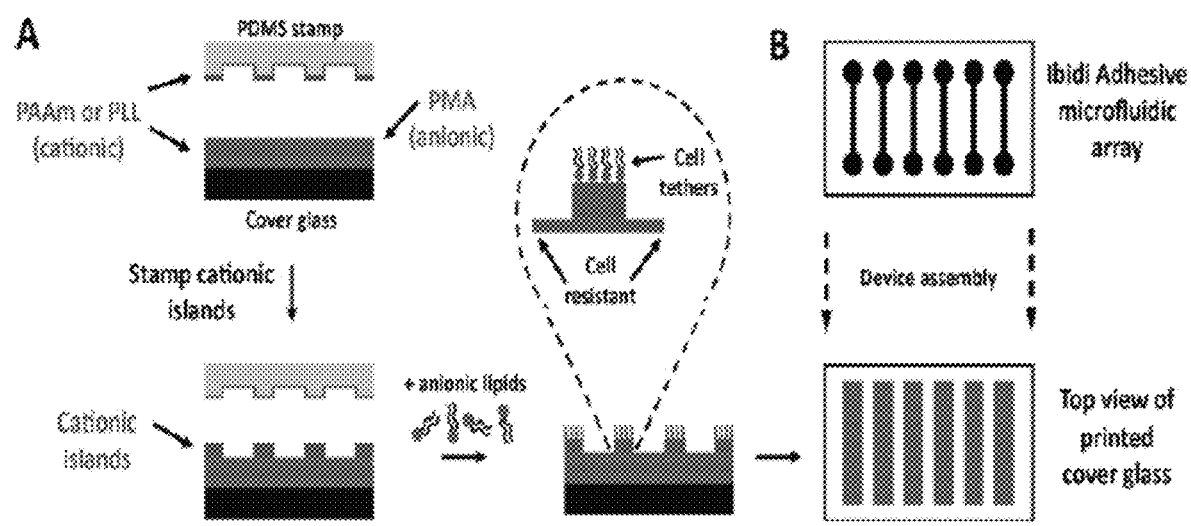
FIG. 22. μCP allows patterning of single-cell lipid tethers on a cytophobic PEM background. A) μCP of a cationic layer produces cationic islands for integration of lipid tethers on a background of a CTC resistant PEM. B) The patterned cover glass is then aligned and assembled with an adhesive microfluidic array.

To generate an array of single-cell lipid attachment points, we will use a PDMS microcontact printing (μCP) procedure that patterns lipid on the upper PEM layer (PAAm or PLL) in small 5-10 μm spots (Kohli N, Vaidya S, Ofoli R Y, Worden R M, Lee I (2006). Arrays of lipid bilayers and liposomes on patterned polyelectrolyte templates. *J Colloid Interface Sci* 301: 461-469). The geometry that we used for FIG. 18 (7 μm spots with 40 μm spacing between centers) is a good starting point, since it works well for the DNA tethering approach. Since the μCP method will require a flat surface, we will first deposit PAAm/PAM PEMs on ultra-clean glass coverslips (Nexterion—Applied Microarrays, Inc.) along the Ibidi slide channel geometry in the UMCP nanofabrication facility (Fablab). A PDMS master containing the stamping geometry will be "inked" with a cationic layer (i.e., PAAm or PLL) and brought in contact with the PEM using a robotic deposition system or EVG aligners (FIG. 22A). Surfaces will then be exposed to the lipid compositions and densities described in Aim 2a, washed, followed by assembly of the final device by binding the coverslip to a matching adhesive array of six microfluidic channels (FIG. 22B), which is available from Ibidi (sticky-Slide VI0.4, FIG. 19B).

The μCP technique is more complicated than simple solution based adsorption of DNA labels (Aim 1), but the technique is well-established and we do not anticipate significant challenges considering the outstanding instrumentation and expertise available. Suss and EVG proximity/contact aligners, Headway photoresist spinners (for preparation of masters), and SEMs will be the most useful resources. To simplify cell tethering in intact channels, we will design a photoactivatable lipid tether.

c) Develop Photoactivatable Lipid Anchor for Lithography Directly in Microfluidic Channels.

Strategy and Analysis: Conjugation of a photo-cleavable charged group to the end of the lipid would generate a molecule that could be integrated in solution to the PEM layer in intact microfluidic channels. We will use a 6-nitropiperonyloxymethyl (NPOM) group, which can be coupled to lipid via an amine linker and then cleaved through illumination with UV light at 365 nm (FIG. 23). The charges present on the NPOM should reduce hydrophobic interactions with the cell membrane. We will prepare a photolithography mask in the Fablab and use the Suss mask aligner—able to pattern features >1 μm—to directly illuminate PEM coated Ibidi microchannels with 7 μm islands and 40 μm center spacing (as in the DNA tethering arrays, FIG. 18).

Stocks of 18:OLysoPG-NPOM will be custom synthesized by Avanti Polar Lipids, Inc. If successful, this approach will eliminate the need for stamping.

The precise lipid for NPOM conjugation will be guided by the studies in 2a. However, it is possible that the single remaining amine will provide enough charge to significantly reduce the membrane tethering of 18:OLysoPG. In this case, we will have to identify another photoactive group with reduced residual charge upon cleavage and work with Fablab experts on a new lithography method.

3. Analyze Patient Tumor Cell Microtentacles and Drug Responses and Relate to Tumorgraft Outcome McTNs on the surface of free-floating tumor cells serve as an indicator of their reattachment efficiency during experimental metastasis in vivo (Balzer E M, Whipple R A, Thompson K, Boggs A E, Slovic J, Cho E H et al (2010). c-Src differentially regulates the functions of microtentacles and invadopodia. *Oncogene* 29: 6402-6408; Matrone M A, Whipple R A, Thompson K, Cho E H, Vitolo M I, Balzer E M et al (2010). Metastatic breast tumors express increased tau, which promotes microtentacle formation and the reattachment of detached breast tumor cells. *Oncogene* 29: 3217-3227). In addition, we have recently published an article in Cancer Research demonstrating that McTNs are a marker of increased tumor stem cell characteristics (Charpentier M S, Whipple R A, Vitolo M I, Boggs A E, Slovic J, Thompson K N et al (2013). Curcumin targets breast cancer stem-like cells with microtentacles that persist in mammospheres and promote attachment. *Cancer Res*). In this experiment, we will use the prioritized PEM devices and live-cell confocal microscopy to examine McTN extension and dynamics in freshly-isolated tumor cells from breast cancer patients. These findings on McTN incidence and drug response will be related to the tumorigenic and metastatic properties of parallel patient-derived tumorgrafts. Tumor cells acquired from residual de-identified patient tissue by the Translational Core lab will be directly transplanted into the cleared mammary fat pad of immunodeficient NOD/SCID mice. This system was developed by Dr. Alana Welm at the University of Utah Huntsman Cancer Institute and avoids altering the properties of patient-derived tumor cells through selection with in vitro culture conditions. In a recent Nature Medicine article (DeRose Y S, Wang G, Lin Y C, Bernard P S, Buys S S, Ebbert M T et al. (2011). Tumor grafts derived from women with breast cancer authentically reflect tumor pathology, growth, metastasis and disease outcomes. *Nat Med* 17: 1514-1520), Dr. Welm's group showed that the direct transplantation method allows tumorgrafts to retain the ER/PR/HER2 status and emulate the metastatic dissemination pattern of the original patient's tumor. It was particularly notable that when the patients' tumors successfully grew in mice, those patients were at a much higher risk of early recurrence and shortened survival (DeRose Y S, Wang G, Lin Y C, Bernard P S, Buys S S, Ebbert M T et al (2011). Tumor grafts derived from women with breast cancer authentically reflect tumor pathology, growth, metastasis and disease outcomes. *Nat Med* 17: 1514-1520). We already have a number of tumorgraft lines in-hand (Table 3), that were generated from residual de-identified tissue from breast cancer patients at the UMGCC by the Translational Core lab, or provided by the Huntsman Cancer Institute. However, while tumorgrafts faithfully retain the clinical characteristics of the original patient, tumorgraft results often require many months to develop (DeRose Y S, Wang G, Lin Y C, Bernard P S, Buys S S, Ebbert M T et al (2011). Tumor grafts derived from women with breast cancer authentically reflect tumor pathology, growth, metastasis and disease outcomes. *Nat Med* 17: 1514-1520; DeRose Y S, Gligorich K M, Wang G, Georgelas A, Bowman P, Courdy S J et al (2013). Patient-derived models of human breast cancer: protocols for in vitro and in vivo applications in tumor biology and translational medicine. *Current protocols in pharmacology*/editorial board, S J Enna Chapter 14: Unit14 23).

TABLE 3

Initial Tumorgraft cell lines

| ID# | ER | PR | HER2 | Metastasis Sites | Dormancy (time to 0.1 cm$^3$) | Race |
|---|---|---|---|---|---|---|
| HCI-001 | − | − | − | Lung, LN | 4 weeks | Caucasian |
| HCI-002 | − | − | − | LN | 5 weeks | Caucasian |
| HCI-003 | + | + | − | Lung, LN | 11 weeks | Caucasian |
| HCI-004 | − | − | − | None detected | 21 weeks | Caucasian |
| HCI-005 | + | + | + | Lung, bone | 13 weeks | Caucasian |
| HCI-008 | − | − | + | Lung, bone | 20 weeks | Caucasian |
| HCI-010 | − | − | − | Lung, LN | 25 weeks | Caucasian |
| HCI-011 | + | + | − | LN, pleura | 27 weeks | African-America |
| UMB-BR-001 | − | − | − | Pending | 3 weeks | African-America |
| UMB-BR-002 | − | − | − | Pending | 5 weeks | African-America | a) Compare Efficiency of 2 PEM Devices for Tethering Patient-Derived Tumorgraft Cells.

Strategy and Analysis: The efficiency of DNA-mediated and lipid-mediated tumor cell tethering will be compared to determine which device will be advanced to a larger clinical study. We will use these existing tumorgrafts (Table 3) to recover breast tumor cells from tissue and determine which approach yields the most efficient retention of 5,000 purified epithelial cells with the least residual contamination with fat cells, lymphocytes and red blood cells. Cell retention will be followed by automated hemocytometer (Countess). Following the outcome of this analysis, we will select either the DNA or lipid-based tethering approach.

Since only about 40% of human breast cancer tumorgrafts grow after orthotopic transplantation (DeRose Y S, Wang G, Lin Y C, Bernard P S, Buys S S, Ebbert M T et al (2011). Tumor grafts derived from women with breast cancer authentically reflect tumor pathology, growth, metastasis and disease outcomes. *Nat Med* 17: 1514-1520), we will start our analysis with existing tumorgrafts obtained from our Translational Core lab and the Huntsman Cancer Institute (Table 3). While we are confident that one or both of the tethering strategies will work for tumorgraft and fresh patient samples, it remains possible that neither tether will be effective. In this case, we will still be able to analyze the McTN incidence and drug response of the samples (as we did in FIGS. 1, 6, 7 and 11), the cells will just be more randomly distributed and we will have to use fewer cells per channel to prevent cell-cell clustering during random cell drifting.

b) Expand Analysis with Prioritized Device to 40 Patients for McTN Analysis and Drug Response Studies.

Figure 12:
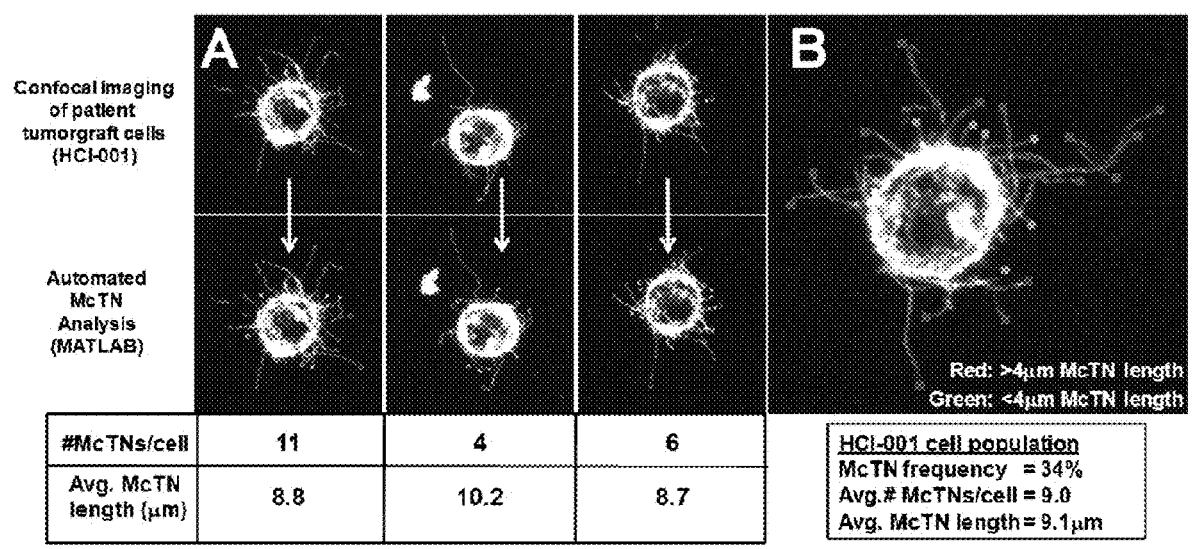
FIG. 12. Automated Measurements of Microtubule (McTN) Characteristics.
Figure 14:
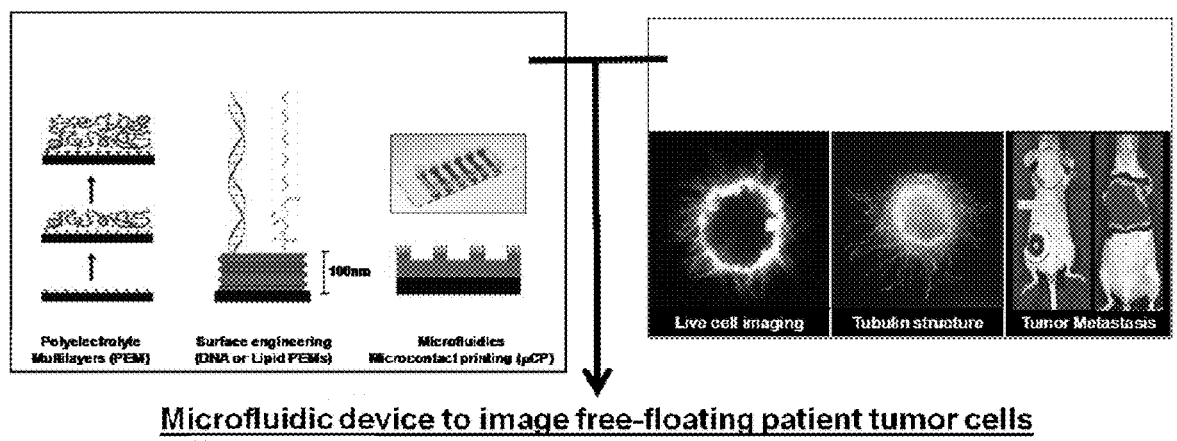
FIG. 14. Schematic showing tethering of cells to a microfluidic slide to image free floating patient cancer cells. The tether can hold the cell in place for confocal imaging and efficient capture of images.
Figure 14:
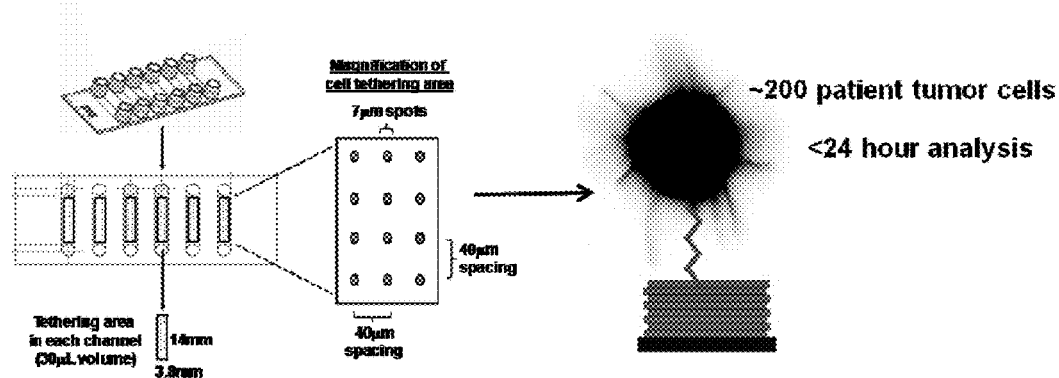
Figure 15:
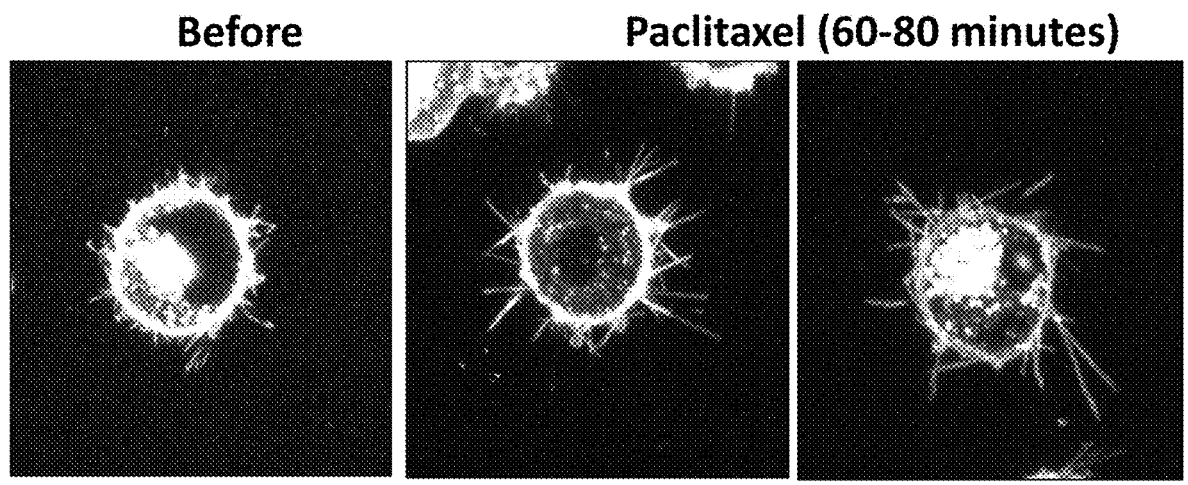
FIG. 15. Confocal images of tethered cells treated with paclitaxel and colchicine.
Figure 15:
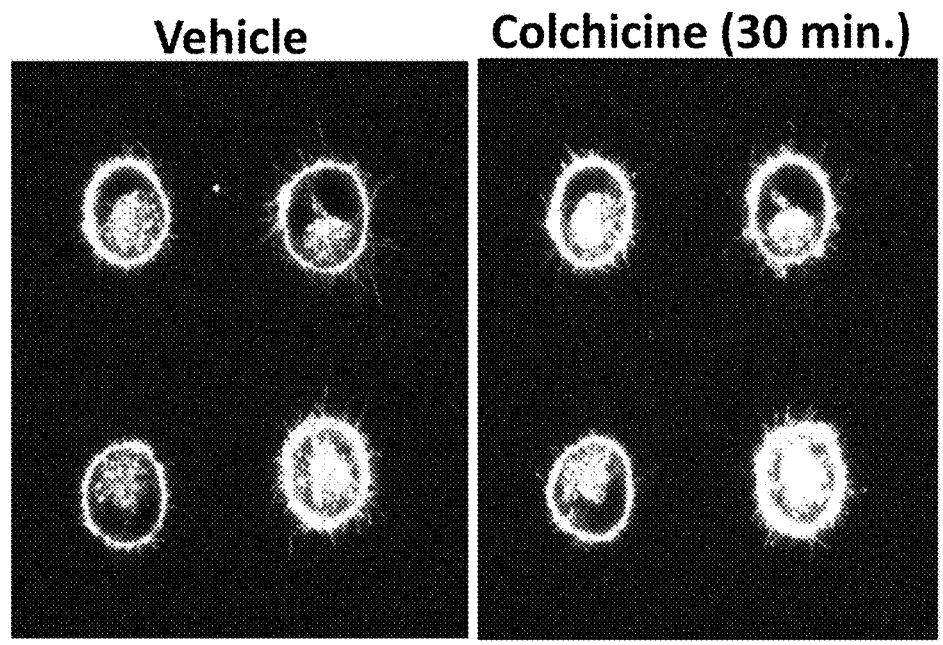
Figure 16:
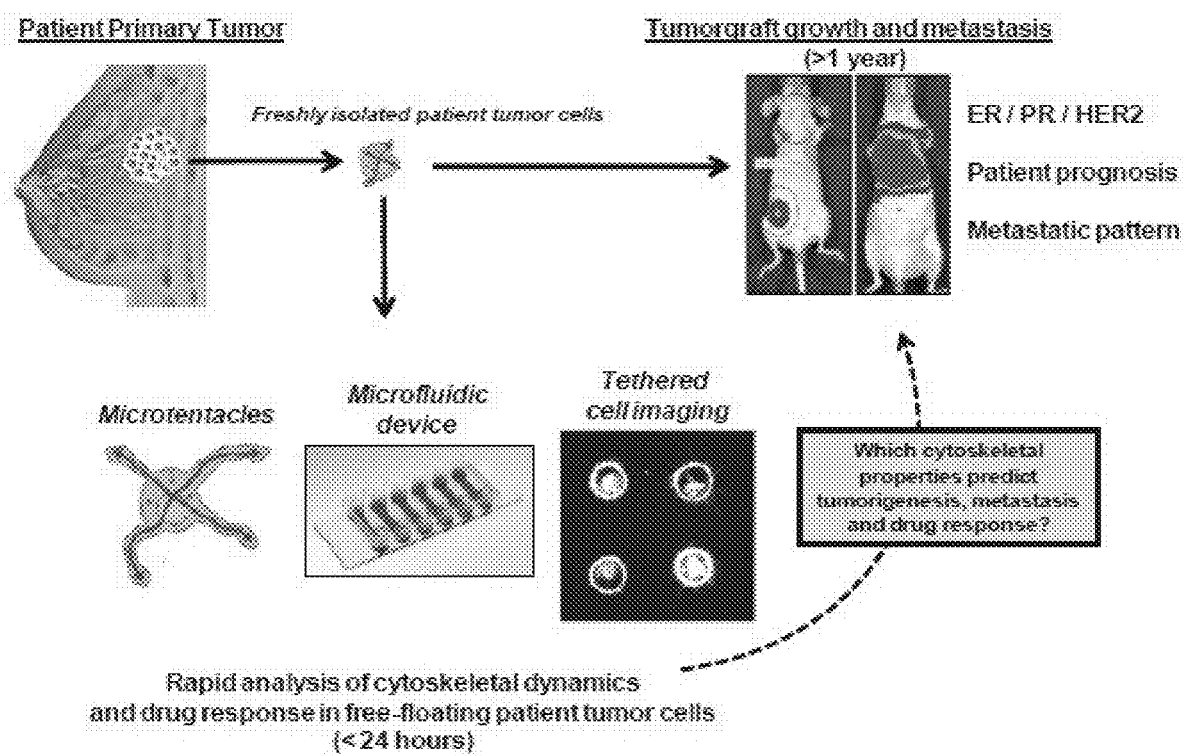
FIG. 16. Schematic showing isolation of cancer cells and subsequent analysis of microtentacles using a microfluidic device and tumor graft growth and metastasis.

Strategy and Analysis: The device will be used to analyze fresh patient samples as well as the resulting tumorgrafts from 40 patients during the three years of the project. McTN images collected from each cell sample will be analyzed with a custom MatLab algorithm developed for this assay that can automatically identify McTNs but also score metrics that were previously not possible to measure, such as the average number of McTNs per cell (FIG. 12). We are currently incorporating the ability to measure average McTN length and curvature. Once we have established the baseline levels of McTNs for each cell sample, we will test the responses to 6 different microtubule-directed drug compounds that are either already FDA-approved or in trials (Table 4). Drugs will be added by media exchange across the six microfluidic channels at the concentrations listed in Table 4 for 60 minutes, which each affect McTNs in 1 hr. (Whipple R A, Balzer E M, Cho E H, Matrone M A, Yoon J R, Martin S S (2008). Vimentin filaments support extension of tubulin-based microtentacles in detached breast tumor cells. *Cancer Research* 68: 5678-5688; Whipple R A, Matrone M A, Cho E H, Balzer E M, Vitolo M I, Yoon J R et al (2010). Epithelial-to-mesenchymal transition promotes tubulin detyrosination and microtentacles that enhance endothelial engagement. *Cancer Res* 70: 8127-8137; Charpentier M S, Whipple R A, Vitolo M I, Boggs A E, Slovic J, Thompson K N et al (2013). Curcumin targets breast cancer stem-like cells with microtentacles that persist in mammospheres and promote attachment. *Cancer Res.*; Whipple R A, Vitolo M I, Boggs A E, Charpentier M S, Thompson K, Martin S S (2013). Parthenolide and costunolide reduce microtentacles and tumor cell attachment by selectively targeting detyrosinated tubulin independent from NF-kappaB inhibition. *Breast Cancer Res* 15: R83), except Ixabepilone, which has not been tested yet on McTNs.

TABLE 4

List of cytoskeletal modulators. (FDA-approved*)

| Drugs | Conc. | Target | Effect | Predicted stemness & McTN effect |
|---|---|---|---|---|
| Paclitaxel* | 1 µM | Microtubules | Stabilize | Increase |
| Ixabepilone* | 0.2 µM | | | |
| Vinblastine* | 0.1 µM | Microtubules | Depolymerize | Decrease |
| Colchicine* | 50 µM | | | |
| Parthenolide | 10 µM | | | |
| Curcumin | 50 µM | | | | c) Analyze Patient Tumor Cell Microtentacles and Drug Responses and Relate to Tumorgraft Outcome.

Strategy and Analysis: The McTN metrics measured for the fresh cells and tumorgrafts (McTN frequency, Avg. McTNs per cell, Avg. McTN length) will be compared to the eventual outcome of the tumorgrafts (growth rate, metastatic efficiency, metastatic site), through a generalized McNemar's test of matrix results, as we have published previously (Matrone M A, Whipple R A, Thompson K, Cho E H, Vitolo M I, Balzer E M et al (2010). Metastatic breast tumors express increased tau, which promotes microtentacle formation and the reattachment of detached breast tumor cells. *Oncogene* 29: 3217-3227). McTN metrics will also be compared to patient outcome and survival data, but the timeframe of this comparison will exceed the project period and likely take >10 years.

Example 7

Novel Microfluidic Cell Tethering Device Enables Microtentacle Analysis of Free-Floating Breast Tumor Cells Cancer metastasis occurs when epithelial tumor cells travel through non-adherent microenvironments, like the bloodstream or lymphatics, to a distant organ (Pantel K and Brakenhoff R H, *Nat Rev Cancer* 2004; 4(6):448-456; Joosse S A, *EMBO Mol Med* 2015; 7(1):1-11). The presence of tumor cells in the non-adherent microenvironment of the bloodstream, known as circulating tumor cells (CTCs), has been detected in numerous epithelial cancers including breast, prostate, colon, and lung (Joosse S A, *EMBO Mol Med* 2015; 7(1):1-11). CTCs are an early indicator of clinical spread of disease and their levels correlate with decreased survival of patients with cancer (Cristofanilli M, *N Engl J Med* 2004; 351(8):781-791; Cristofanilli M, *J Clin Oncol* 2005; 23(7):1420-1430; Krebs M G, *J Clin Oncol* 2011; 29(12):1556-1563). In addition, monitoring CTCs in patients over time and in response to therapy can provide significant information on tumor response and can even be more sensitive than current imaging methods (de Bono J S, *Clin Cancer Res* 2008; 14(19):6302-6309; Slade M J, *Br J Cancer* 2009; 100(1):160-166; Pierga J Y, *Clin Cancer Res* 2008; 14(21):7004-7010). Based on the increasing clinical relevance of CTCs, understanding their molecular profile is emerging as a new opportunity to gain insight on disease progression and patient prognosis beyond enumeration alone. Though progress has been made on technologies to enhance the identification and enumeration of CTCs, (Pantel K and Speicher M R, *Oncogene* 2015; Yu M, *J Cell Biol* 2011; 192(3):373-382; Stott S L, *Proc Natl Acad Sci USA* 2010; 107(43):18392-18397), major limitations remain in performing downstream functional studies due to challenges with accurate detection and the low number of CTCs that can be retrieved from patient blood (frequency of approximately 1 in 100 million cells in the bloodstream) (Pantel K and Speicher M R, *Oncogene* 2015). Some of the techniques currently being employed to analyze CTCs include fluorescence in situ hybridization, sequencing, immunostaining, xenograft transplantation, and RNA or protein-based expression analysis (Pantel K and Speicher M R, *Oncogene* 2015; Yu M, *J Cell Biol* 2011; 192(3):373-382; Yu M, *Science* 2014; 345(6193):216-220; Yu M, *Science* 2013; 339(6119): 580-584). However, these methods do not allow for real-time analysis of CTCs in an environment that preserves their free-floating nature.

Microscopy analysis of CTCs has focused almost exclusively on cells adhered to surfaces (glass, plastic, ECM) owing to ease of imaging and characterization of cells in these static positions. However, new studies reveal that the functions and molecular characteristics of CTCs are different in adhered and free-floating states. Thus a critical knowledge gap exists in the understanding of epithelial tumor cells in non-adherent microenvironments, such as those found in the blood vessels or capillaries. Non-adherent breast carcinoma cells, for example, produce unique tubulin-based microtentacles (McTNs) that promote tumor cell aggregation (Whipple R A, *Exp Cell Res* 2007; 313(7):1326-1336; Yoon J R, *Breast Cancer Res Treat* 2011; 129(3):691-701), reattachment to endothelial layers (Whipple R A, *Cancer Res* 2010; 70(20):8127-8137; Matrone M A, *Cancer Res* 2010; 70(20):7737-7741), and retention of circulating tumor cells in the lungs of mice (Balzer E M, *Oncogene* 2010; 29(48):6402-6408; Matrone M A, *Oncogene* 2010; 29(22):3217-3227). New enabling technologies to image tumor cells, McTNs, and other features in the absence of extracellular matrix (ECM) attachment could vastly improve the understanding of dynamic cell behaviors that occur in the non-adherent microenvironments encountered by CTCs during metastasis. These tools could also support opportunities for selective targeting of drugs to McTNs or other structures presented preferentially by CTCs during metastatic spread, as well as help address rising concerns that chemotherapies meant to reduce tumor growth may actually increase metastatic risk (Balzer E M, *Breast Cancer Res Treat* 2010; 121(1):65-78). Here, we exploited the discovery that McTNs form only when protein-based adhesions are absent to create an innovative platform for real-time imaging of the dynamic features of live, non-adherent tumor cells.

Biomaterials offer many attractive features—stability, biocompatibility, versatile chemistries—for controlling cell adhesion. Common approaches include chemically functionalizing surfaces (Kato K, *Biotechniques* 2003; 35(5): 1014-1018, 1020-1011; Lee H, *Science* 2007; 318(5849): 426-430; O'Brien F J, *Biomaterials* 2005; 26(4):433-441; Okano T, *Biomaterials* 1995; 16(4):297-303), incorporating cell adhesion peptides (Seeto W J, *Acta Biomaterialia* 2013; 9(9):8279-8289; Hersel U, *Biomaterials* 2003; 24(24):4385-

4415; Fierer J O, *Proc Natl Acad Sci USA* 2014; 111(13): E1176-1181), and micropatterning using polymer-based soft lithography (Zheng W, *Advanced Healthcare Materials* 2013; 2(1):95-108) or electrospinning techniques (Min B-M, *Biomaterials* 2004; 25(7-8):1289-1297). Of particular note, several recent studies have exploited biomaterials to identify CTCs (Park G-S, *Nano Letters* 2012; 12(3):1638-1642; Halo T L, *Proceedings of the National Academy of Sciences* 2014; 111(48): 17104-17109; Mitchell M J, *Biomaterials* 2015; 56:179-186) or used microfluidic devices to isolate and immobilize CTCs by acoustic separation, topography, controlled flow rates, and antibodies traps (Adams A A, *Journal of the American Chemical Society* 2008; 130(27):8633-8641; Stott S L, *Proceedings of the National Academy of Sciences* 2010; 107(43):18392-18397; Rhee S W, *Lab on a Chip* 2005; 5(1):102-107; Sarioglu A F, *Nat Meth* 2015; 12(7):685-691; Li P, *Proceedings of the National Academy of Sciences* 2015; 112(16):4970-4975). Polyelectrolyte multilayers (PEMs) are biomaterials that contain self-assembled structures formed through electrostatic or hydrogen bonding interactions between polymers during layer-by-layer (LbL) deposition. PEMs have the ability to coat topographically-complex surfaces (e.g., planar, colloidal, microfluidic) and offer programmable surface features and functionalities depending on polymers used to assemble the films. PEMs have recently been employed to study CTCs by promoting adhesion to PEMs incorporating cytophilic polymers or cell-adhesive protein domains (Zanina N, *Biotechnol Bioproc E* 2013; 18(1):144-154; Best J P, *Soft Matter* 2013; 9(18):4580-4584; Reategui E, *Adv Mater* 2015; 27(9):1593-1599; Lee H, *ACS Nano* 2011; 5(7):5444-5456). These techniques have demonstrated great potential in capturing and immobilizing CTCs. However, new strategies are needed to study the dynamics of McTNs and other unique metastatic features that form only when CTCs are in non-adherent or circulating environments.

To enable this new class of studies, we identified three design features that would allow prolonged, real-time imaging and drug screening of McTNs on tumor cells in a free-floating state: 1) optically-clear coatings to support imaging, 2) ability for controlled flow (e.g., drugs, staining buffers) over tethered cells and 3) simple, low-energy manufacturing process. Past studies have demonstrated the utility of PEMs for tuning cell adhesion by varying polymer composition or through addition of lipids, RGD sequences, or other binding moieties (Mendelsohn J D, *Biomacromolecules* 2003; 4(1):96-106; Yamahira S, *Macromol Biosci* 2014; 14(12):1670-1676; Yamaguchi S, *Angew Chem Int Ed Engl* 2012; 51(1):128-131; Richert L, *Biomacromolecules* 2004; 5(2):284-294; Kohli N, *J Colloid Interface Sci* 2006; 301(2):461-469; Chen J, *Soft Matter* 2009; 5(1):228-233; Zhang Y, *Chemistry* 2013; 19(27):9059-9063; Yang S Y and Seo J-Y, *Colloids and Surfaces A: Physicochemical and Engineering Aspects* 2008; 313-314:526-529; Yang S Y, *Biomacromolecules* 2003; 4(4):987-994). Thus, we leveraged the properties of PEMs to design a platform for weak "tethering" of tumor cells on microfluidic devices. We show that assembling these coatings on microfluidic device with cytophobic films and lipid tethers support maintenance of free-floating properties of tumor cells. When tethered, McTNs on live cells can be visualized in real time and the dynamics of these structures can be assessed through microfluidic flow of drugs that enhance or depolymerize McTNs. This technology could generate new insights of McTN behavior, and support new approaches to exploit McTNs as biomarkers for the metastatic efficiency of tumor cells in diagnosis, prognosis, and targeted drug design.

Results

Figure 25:
FIG. 25. PEMs form a cytophobic layer on microfluidic device, allowing for McTN visualization while maintaining optical clarity. (A) Schematic depicting coating of Ibidi micro-slide with PEMs to promote free floating cells for McTN visualization. (B) PEM coatings increase in size (left axis, black) with increasing number of bilayers while maintaining optical clarity (right axis, gray) Data correspond to the mean of samples prepared in triplicate with error bars representing SEM. (C) Representative maximum intensity z-projection of MDA-MB-436 cells on PEM coated slides showing McTNs (arrows). Scale bar represents 10 μM. Percent attachment of (D) MDA-MB-436 and (E) MCF-7 cells on uncoated and slides coated with 1, 4, or 8 PEM bilayers after washing at 6 and 24 hours. Cell attachment was determined by quantifying the remaining cells with CellProfiler image analysis and expressed as a percent of the initial cell number. Data represents mean of triplicate independent experiments with error representing SEM.
Figure 25:
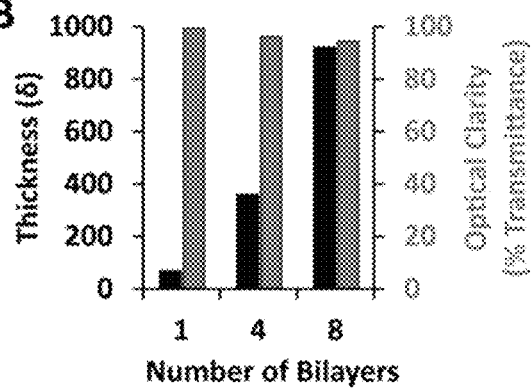
Figure 25:
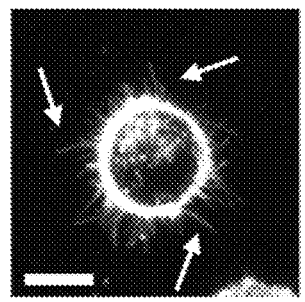
Figure 25:
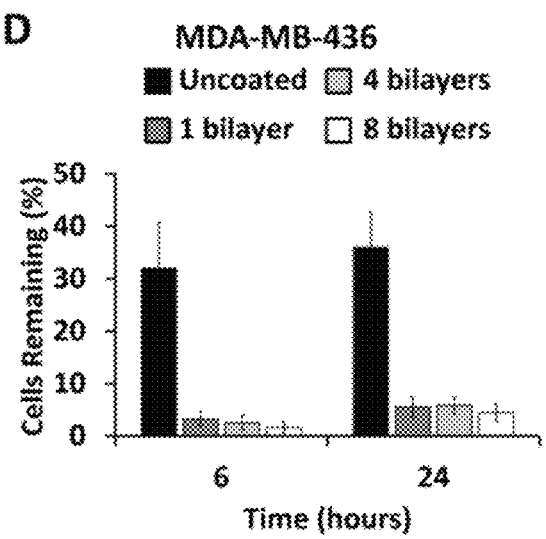
Figure 25:
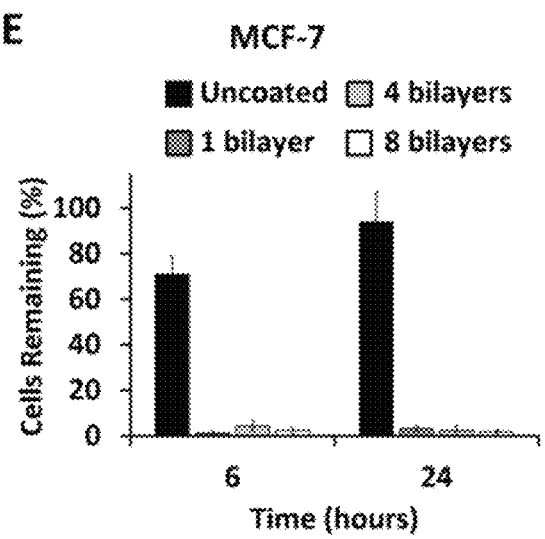

Many of the responses of cancer cells detached from ECM (i.e., in a circulating or free-floating stage) are highly important in survival, apoptosis, metastasis, and even in the expression of stem cell characteristics (For stem cell characteristics—PMID: 25622895; Anoikis/EMT/chemo-resistance/metastasis—PMID: 23516327). However, tumor cells in this state are greatly understudied due to the technical and clinical challenges of continuously imaging cells not adhered to surfaces. Maintaining free-floating cell behavior of breast cancer cells is particularly critical in promoting McTN formation (Whipple R A, *Exp Cell Res* 2007; 313(7): 1326-1336). Since cell adhesion properties are controlled by mechanical and chemical interactions with other cells or surfaces, we leveraged the unique ability of PEMs to create cytophobic surfaces which can maintain the free-floating nature of cells. Using this platform we tested the hypothesis that programming the features and compositions of these coatings would allow spatial localization of tumor cells while maintaining their free-floating characteristics (FIG. 25A).

Figure 31:
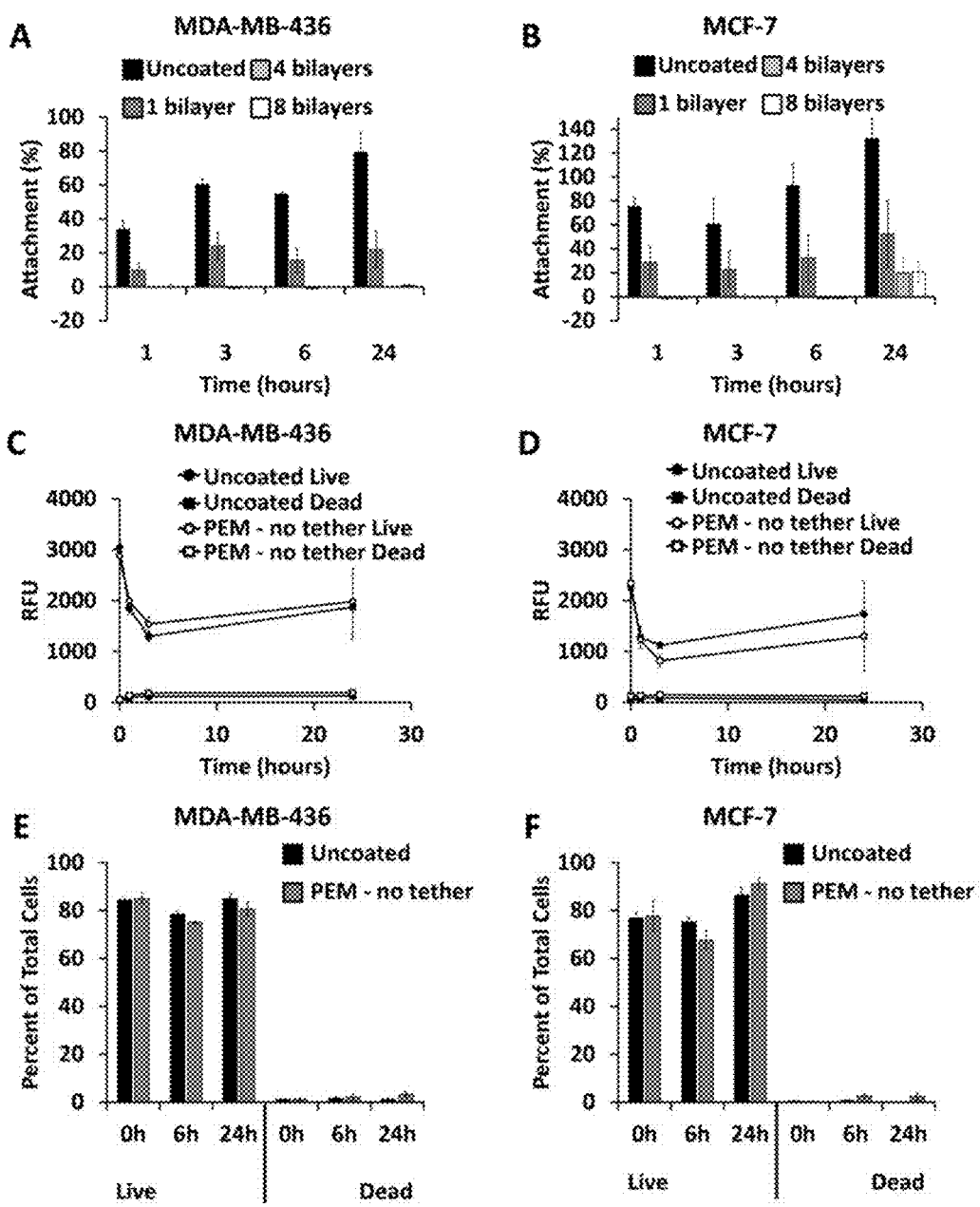
FIG. 31. PEM prevents cell attachment and does not affect cell viability. CellTiter analysis of the number of (A) MDA-MB-436 and (B) MCF-7 cells remaining on 96-well plate coated with 0 (uncoat), 1, 4, and 8 PMA/PAAm bilayers after one wash at 1, 3, 6, and 24 hours normalized to initial cell number. Data represents mean cell attachment from three independent experiments (mean+/−SEM). Viability of (C) MDA-MB-436 and (D) MCF-7 cells on a 96-well plate coated with 0 (uncoat), 1, 4, and 8 bilayers at 0, 1, 3, 6, and 24 hours. Data represents mean viability from three independent experiments (mean+/−SEM). Viability of (E) MDA-MB-436 and (F) MCF-7 cells plated on micro-slides with 0 (uncoated) or 4 PMA/PAAm bilayers calculated at 0, 6, and 24 hours. Fluorescence of live and dead cells were quantified for each (green and red) and divided by total cell number to quantify percent of live and dead cells, respectively using CellProfiler. Data represents mean viability from three independent experiments (mean+/−SEM).
Figure 32:
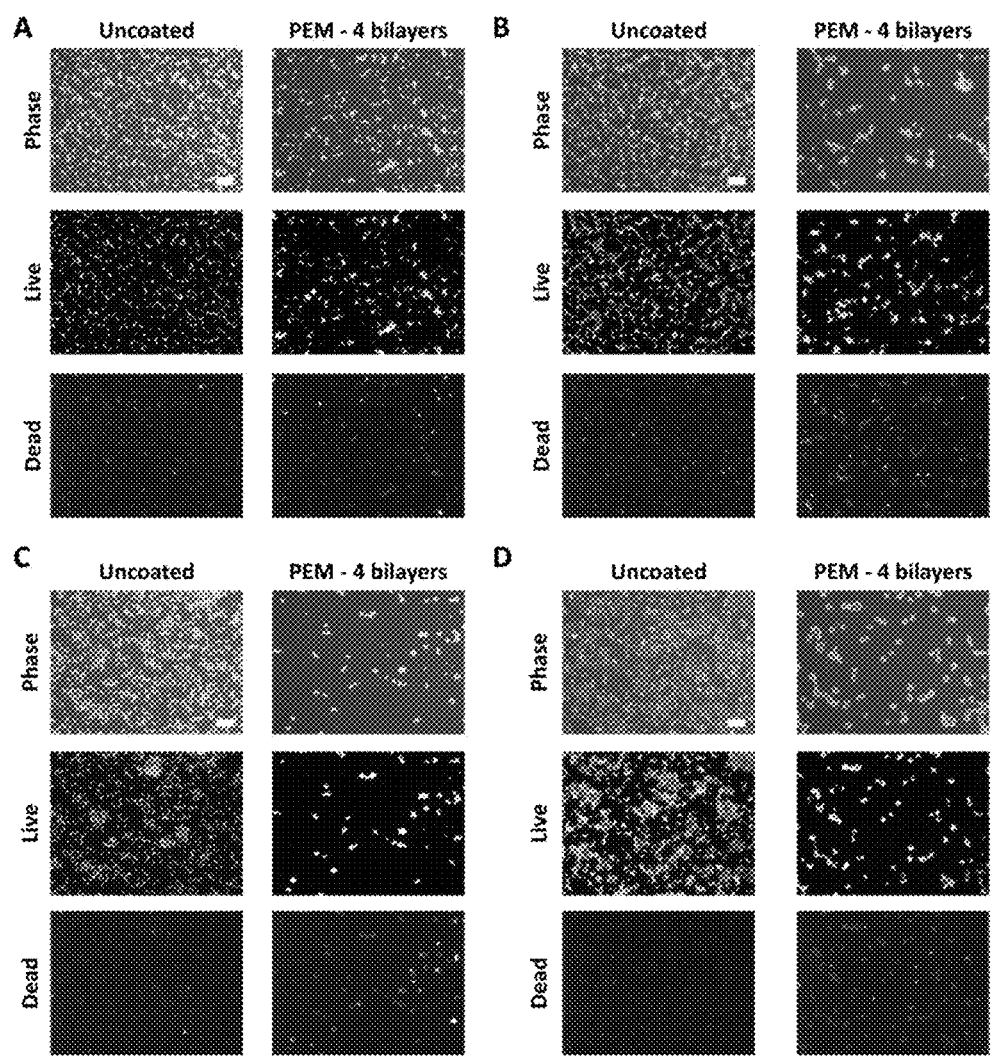
FIG. 32. PEM does not affect viability of MDA-MB-436 and MCF-7 cells. Representative images of the viability of MDA-MB-436 plated on micro-slides with 0 (uncoated) or 4 PMA/PAAm bilayers at (A) 6 hours and (B) 24 hours. Phase contrast images show total cell number, live (green fluoresce), and dead (red fluorescence). Representative images of the viability of MCF-7 plated on micro-slides with 0 (uncoated) or 4 PMA/PAAm bilayers at (A) 6 hours and (B) 24 hours. Phase contrast images show total cell number, live and dead (green and red fluorescence) at 4× magnification. Scare bar represents 200 µM.
Figure 33:
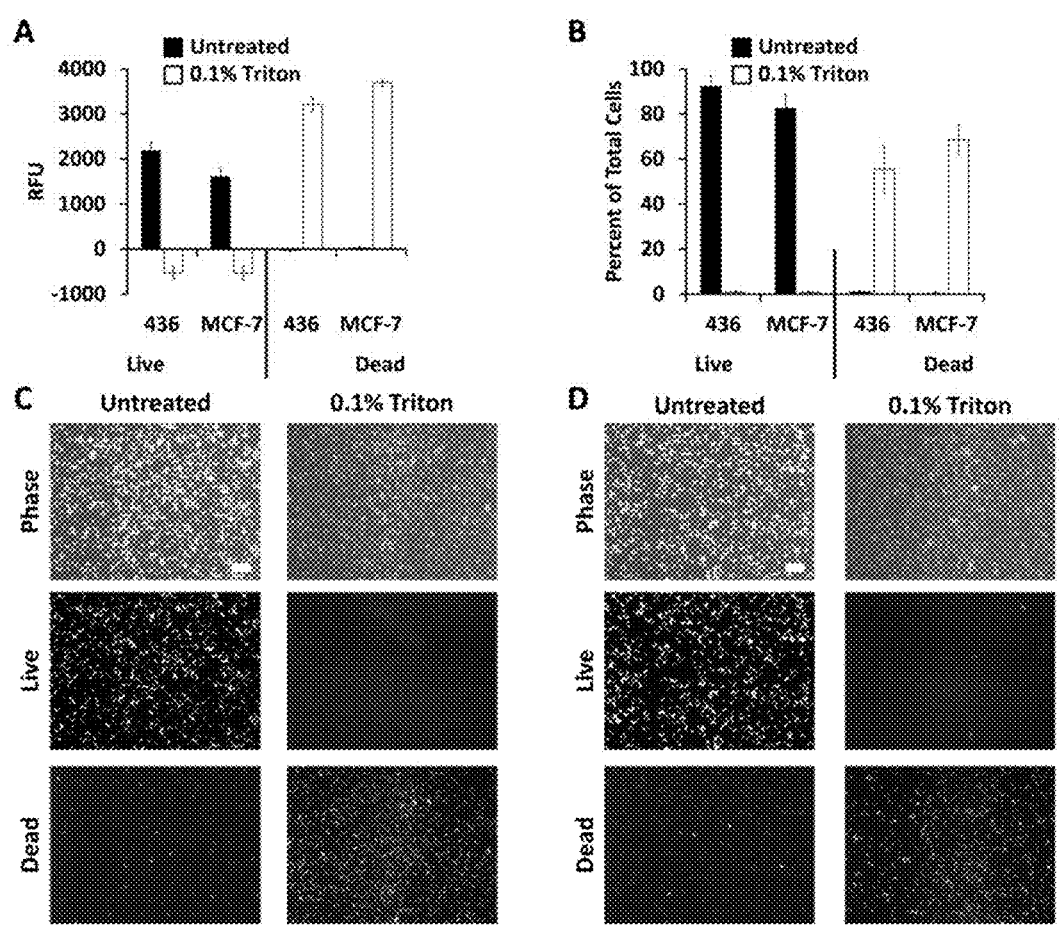
FIG. 33. Triton-X is a positive control for cell death. Cell viability of MDA-MB-436 and MCF-7 cells treated with 0.1% Triton-X plated on (A) 96-well plate and (B) micro-slides. Fluorescence of live and dead cells (green and red fluorescence) were quantified for each and divided by total cell number to quantify percent of live and dead cells, respectively using CellProfiler. Data represents mean viability from three independent experiments (mean+/−SEM). Representative images of (C) MDA-MB-436 and (D) MCF-7 cells treated with 0.1% Triton-X. Phase contrast images show total cell number, live, and dead at 4× magnification. Scale bar represents 200 µM.

We used multilayer deposition of two classical self-assembling polymers, Poly(methacrylic acid) (PMA) and polyacrylamide (PAAm) because these materials have previously been shown to limit cell adhesion of numerous cell types (Mendelsohn J D, *Biomacromolecules* 2003; 4(1):96-106; Yang S Y, *Biomacromolecules* 2003; 4(4):987-994). Substrates coated with PEMs offered precise control over film thickness and did not limit optical transmission, a feature important for pre-clinical and clinical imaging (FIG. 25B). Since human breast tumor cells lines have not yet been tested on these PEM substrates, we first confirmed that PMA/PAAm multilayers could control cell adhesion in two important NCI breast cancer cell lines, MDA-MB-436 and MCF-7. MDA-MB-436 cells seeded on the cytophobic surfaces created by the PEM maintained microtentacle display (FIG. 25C). This is the first time maintenance of the free-floating behavior of tumor cells has been reported, thus we leveraged the LbL deposition process to exploit this opportunity. Following coating on micro-slides or directly on tissue culture treated multi-well plates, cells were allowed to attach for 0, 6, and 24 hours and the number of cells remaining after a wash at each time point was quantified using image analysis and a cell proliferation assay (CellTiter). Image analysis revealed that PEM-coated surfaces on micro-slides prevented the attachment of both cell lines (FIGS. 25E and 25F and FIGS. 30A and 30B) for at least 24 hours using 1, 4, and 8 bilayers. CellTiter data indicated that deposition of 4 bilayers and 8 bilayers showed decreased cell attachment compared with 1 bilayer for both cell lines (FIGS. 31A and 31B). While all of these interactions maintained McTNs, coatings with 4 bilayers were prioritized for future experiments since they were able to form cytophobic surfaces that decreased cell attachment. Both cell lines also remained viable when seeded on PEM coated multi-well plates (FIGS. 31C and 31D) along with micro-slides (FIGS. 31E and 31F). Representative images of cells seeded on PEM coated micro-slides, which were used for quantification, revealed minimal cell death in both cell lines at 6 and 24 hours, compared to an uncoated control (FIG. 32) and the positive control for cell death (FIG. 33). Although PEM-coated surfaces were able to successfully prevent attachment of tumor cells to support free floating behavior, we sought to develop a strategy to maintain McTNs while also providing spatial localization during microfluidic flow for real-time imaging with drug treatment.

Figure 26:
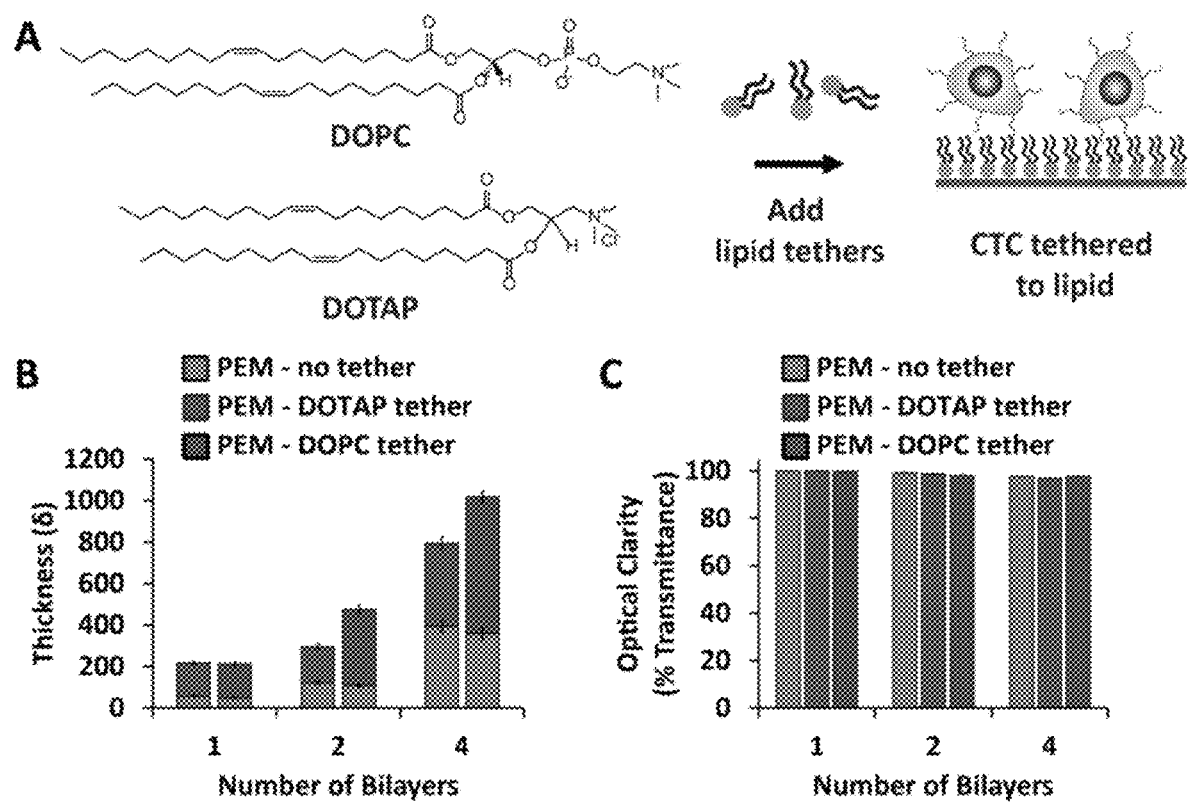
FIG. 26. Lipid-tethered PEMs, while optically clear, allow for tethering of cells to slides for visualization. (A) Schematic depicting how lipids deposited as the terminal layer of a PEM coated slide promotes interactions with cell membranes. (B) Film thickness and (C) optical clarity measurements with the addition of lipids DOPC or DOTAP (Stott S L, et al. (2010) Isolation of circulating tumor cells using a microvortex-generating herringbone-chip. *Proceedings of the National Academy of Sciences* 107(43):18392-18397). Lipids promote growth of film while maintaining an optically clear substrate for imaging. Data correspond to the mean of samples prepared in triplicate where three measurements were taken per slide with error bars representing SEM.
Figure 27:
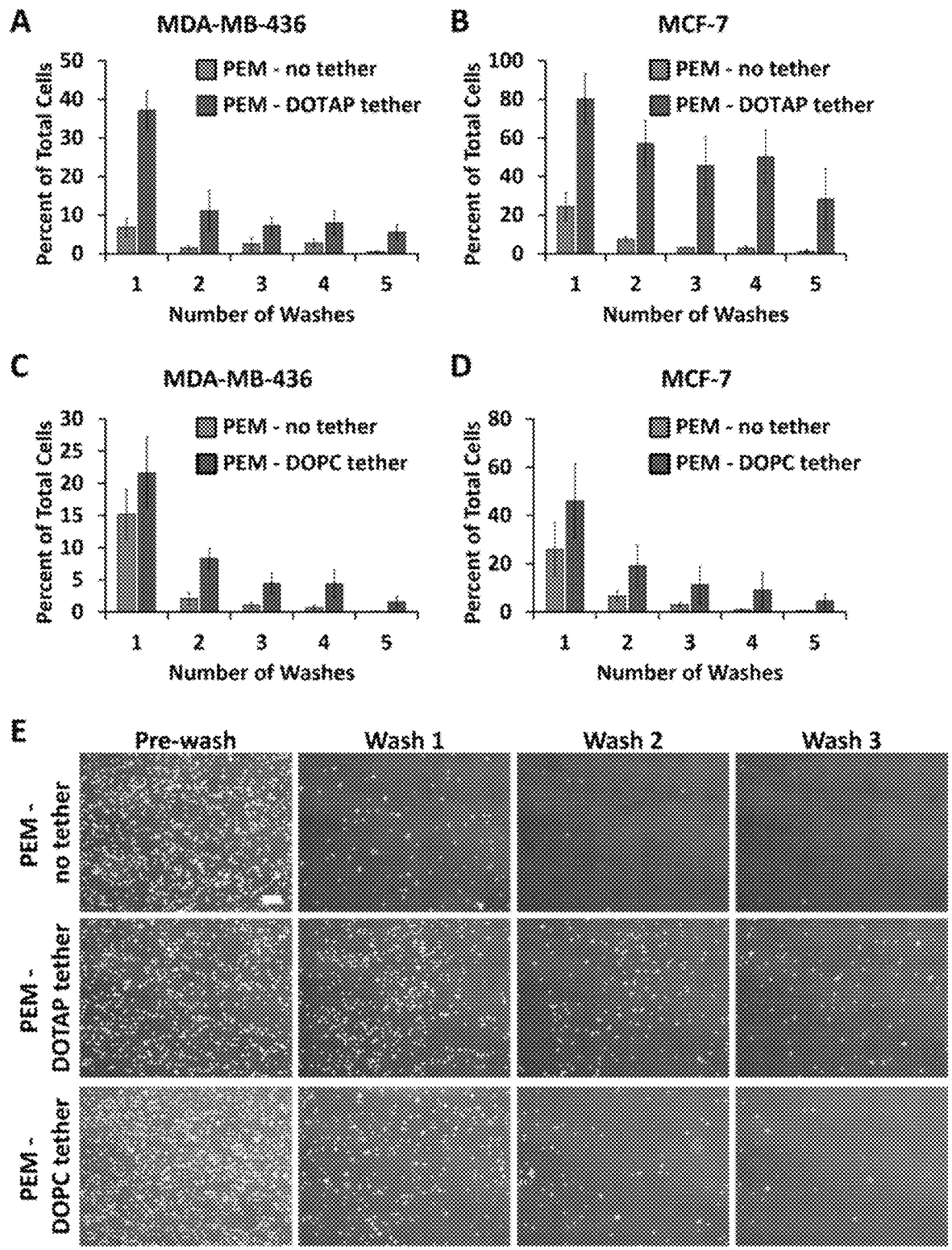
FIG. 27. DOTAP can tether breast cancer cell lines after washing. Percent cell retention of (A) MDA-MB-436 and (B) MCF-7 cells plated on micro-slides coated with 4 PMA/PAAm bilayers alone or with DOTAP and allowed to tether for 1 hour. The remaining cells after each wash were quantified with CellProfiler and expressed as a percent of the initial cell number. Percent cell retention of (C) MDA-MB-436 and (D) MCF-7 cells plated on micro-slides coated with 4 PMA/PAAM bilayers alone or with DOPC and allowed to tether for 1 hour. The remaining cells after each wash was quantified with CellProfiler and expressed as a percent of the initial cell number. Data represents mean of triplicate independent experiments (mean+/−SEM). (E) Representative images of MDA-MB-436 cells at time 0 and after 3 subsequent washes on 4 PEM bilayers with no tether and with PEM-DOTAP or PEM-DOPC tethers at 4× magnification. Scale bar represents 200 μM.
Figure 34:
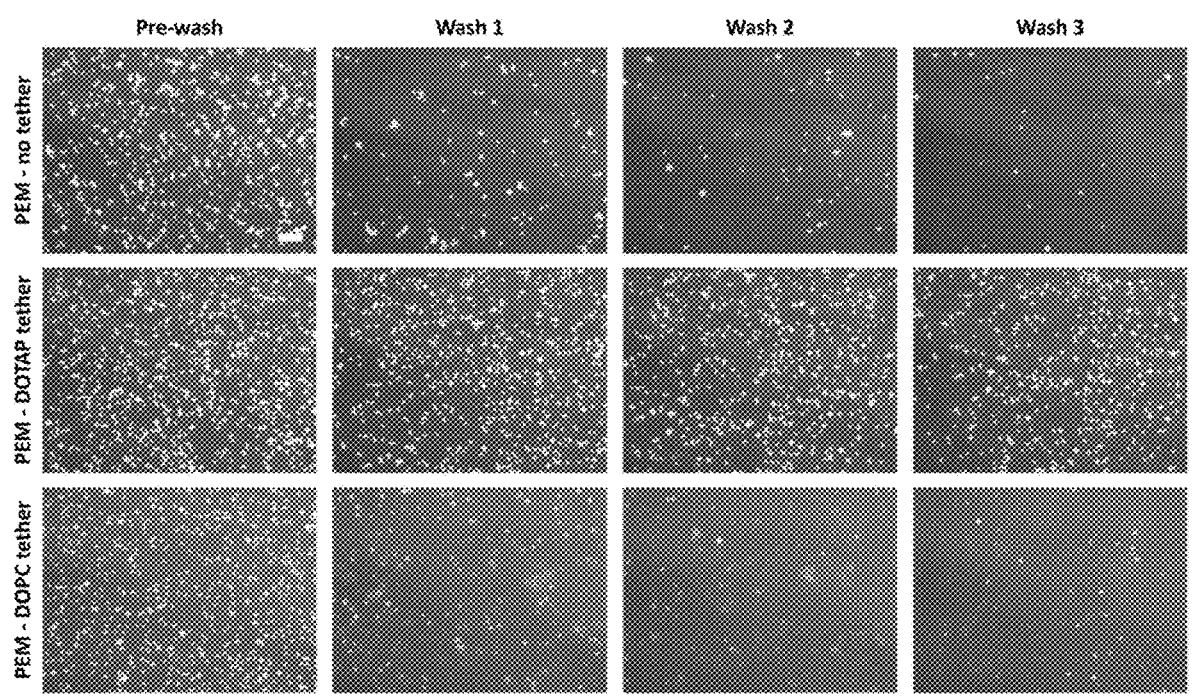
FIG. 34. DOTAP can tether MCF-7 breast tumor cells. Representative images of MCF-7 cells seeded on micro-slides with PEM-no tether, PEM-DOTAP tether, and PEM-DOPC tether prior to washing and after 3 subsequent washes at 4× magnification. Scale bar represents 200 µM.

After determining that PEMs could be used to keep breast cancer cells in a free-floating state during static conditions, we hypothesized that the addition of a terminal lipid layer which can interact with cell membranes would allow for cells to be loosely tethered to the surface during microfluidic flow. We used 1,2-dioleoyl-3-trimethylammonium-propane (DOTAP) and 1,2-dioleoyl-sn-glycero-3-phosphocholine (DOPC) as cationic lipids owing to the ability of these molecules to interact with the PEM electrostatically and cell membranes via hydrophobic interactions (FIG. 26A). During addition of DOTAP or DOPC as the terminal layer to PEM films of 1, 2, and 4 bilayers, total film thickness increased as a function of the polymer layers while maintaining the high optical clarity needed for imaging (FIGS. 26B and 26C). We next tested if these lipids supported tethering of breast tumor cells without strong adhesion that inhibits free-floating features such as McTN. MDA-MB-436 and MCF-7 cells were seeded on micro-slides coated with PEM without lipids (PEM-no tether) or PEMs terminated with either DOPC (PEM-DOPC tether) or DOTAP (PEM-DOTAP). During successive wash steps, DOTAP maintained tumor cells significantly more efficiently compared to non-tethered cells seeded on micro-slides coated with PEM only (FIGS. 27A and 27B). MCF-7 cells exhibited an overall higher cell retention rate over five washes compared to MDA-MB-436. The first wash was the most effective for both cell lines with retention of 38% and 80% of MDA-MB-436 and MCF-7 cells, respectively (FIGS. 27A and 27B). Even after five washes, DOTAP was able to tether 15% of MCF-7 cells, while DOPC in contrast, was unable to effectively tether either type of tumor cells. After one wash cell retention on PEM-DOPC was similar to cells seeded on PEM-coated slides, but with subsequent washes, DOPC tethered a slightly higher percentage of cells compared with PEM slides (FIGS. 27C and 27D). Representative images of MDA-MB-436 and MCF-7 tethered cells over the course of these washes on the indicated surfaces are shown in FIG. 27E and Supplemental FIG. 34. Since DOTAP demonstrated superior tethering compared to DOPC for both cancer cell types, this film architecture was prioritized for functional assays.

Figure 4:
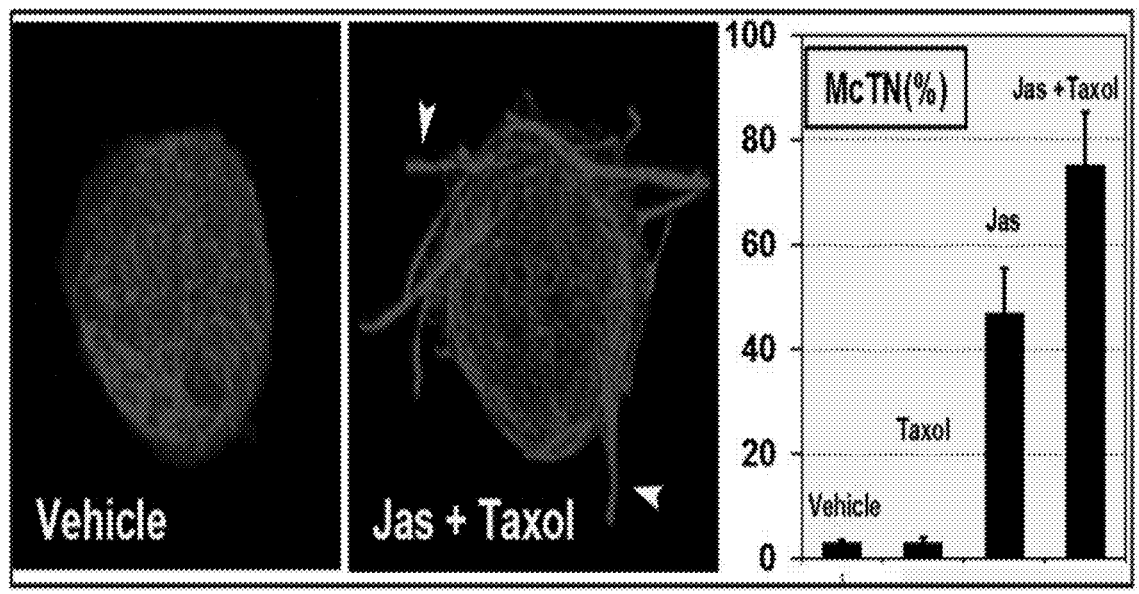
FIG. 4. Targeting cell division can increase McTNs. Treatment of nonmetastatic SkBr3 cells with drugs that prevent cell growth by reducing actin (Jas, 500 nM) and stabilizing microtubules (Paclitaxel-Taxol, 1.2 µM), increases levels of McTNs dramatically, when imaged with confocal microscopy for tubulin localization (white arrows). These data raise concern that some drugs which inhibit cell division could actually increase metastatic potential. (Bars=mean±S.D from 3 expts. with McTNs scored blindly).
Figure 5:
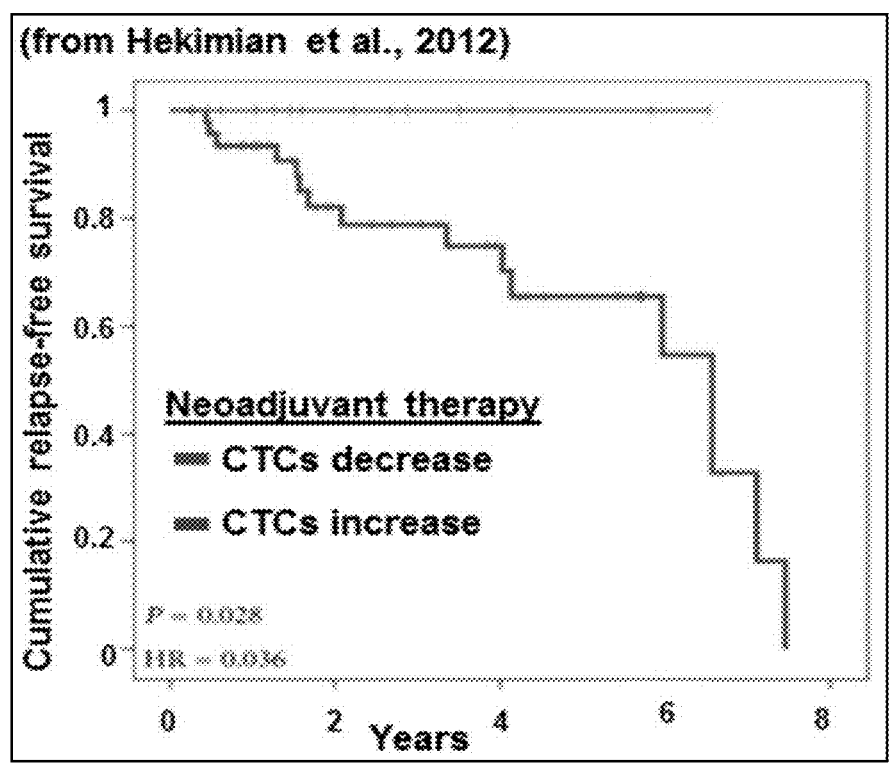
FIG. 5. Poor recurrence-free survival when CTCs increase during neoadjuvant chemotherapy. Patients whose CTC levels decrease during neoadjuvant chemotherapy have a 100% recurrence-free survival after 7 years (upper line). In stark contrast, patients whose CTC levels increase during neoadjuvant therapy have only a 4% recurrence-free survival after 7 years (lower line).
Figure 6:
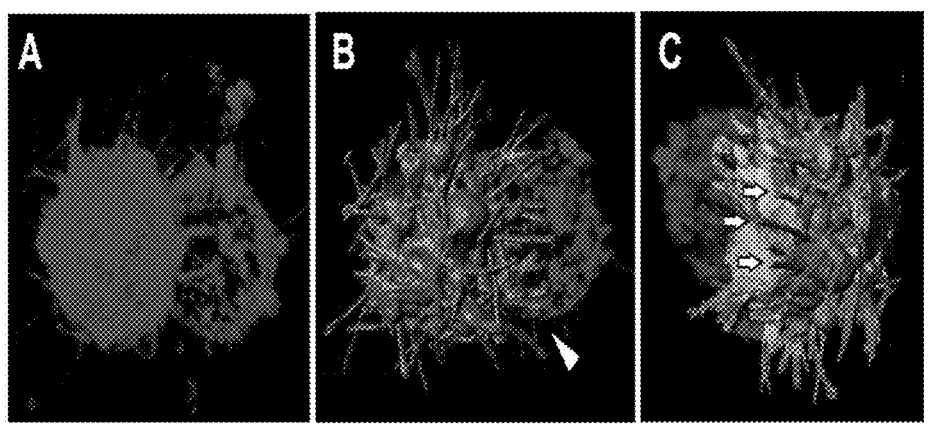
FIG. 6. McTNs promote tumor cell aggregation. A) Detached MDA-436 breast tumor cells were labeled with the lipophilic membrane dye CellMask. When mixed with a population of cells transiently transfected with GFP, this allows specific tracking of the McTNs that encircle neighboring cells during aggregation (B and C, arrowhead). Rotation of the confocal image indicates McTNs bind along surface of adjacent cells.
Figure 7:
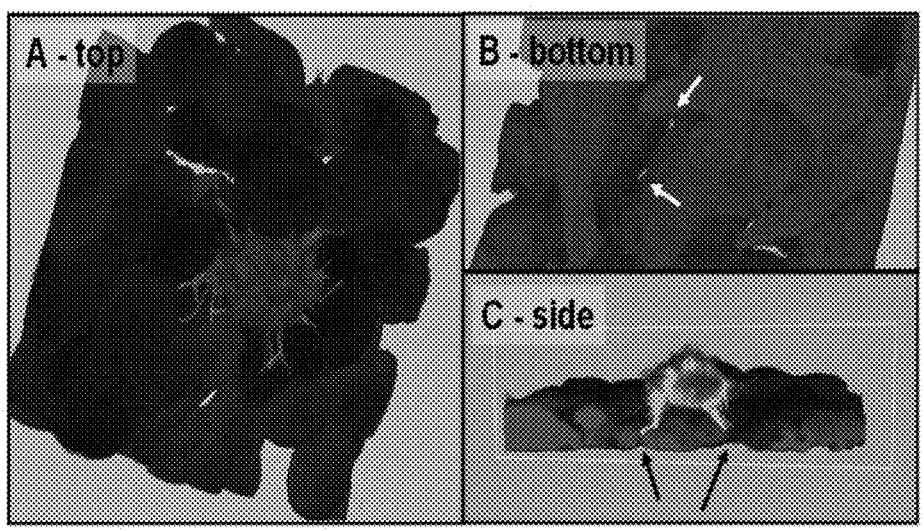
FIG. 7. McTNs promote penetration of endothelial monolayers. A) Live MDA-436 cells expressing membrane-localized GFP were suspended over endothelial monolayers expressing mCherry. Confocal imaging as the cell attaches discerns the penetration of the tumor cell through the layer when viewed from underneath (B, white arrows) or in cross-section (C, black arrows). We will use this high-resolution imaging technique to examine the how altering tubulin detyrosination and Tau affects McTN generation and endothelial binding in this live-cell in vitro model of tumor cell extravasation.
Figure 28:
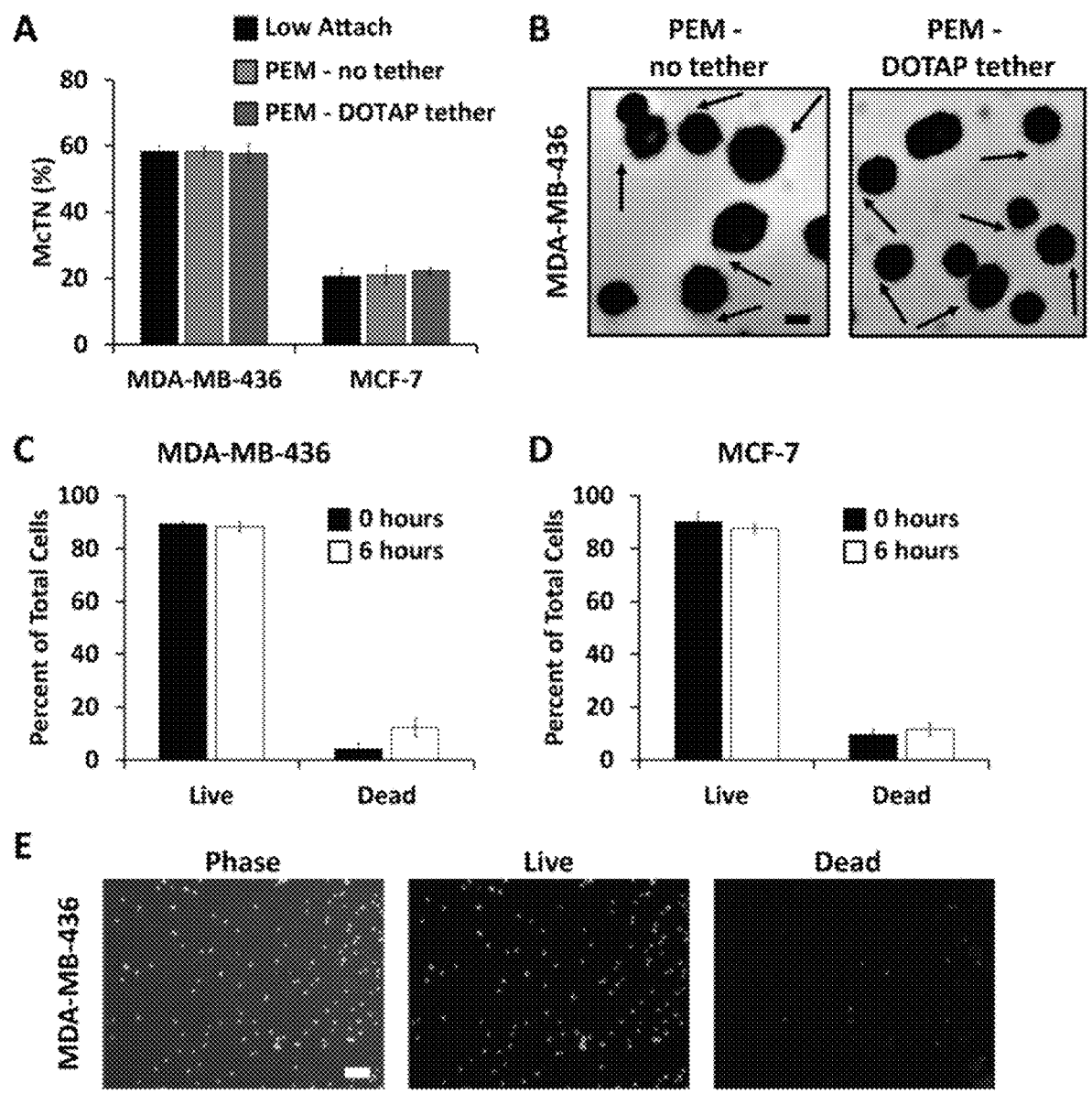
FIG. 28. Lipid tethering retains free-floating characteristics of breast tumor cells and does not affect cell viability. (A) McTN quantification of MDA-MB-436 and MCF-7 cells suspended on a low-attach plate, micro-slides with PEM-no tether, and micro-slides with PEM-DOTAP tether. Data represents blinded quantification of McTN frequency from three independent experiments with 100 cells counted for each (mean+/−SEM). (B) Representative images of McTNs (arrows) on MDA-MB-436 cells seeded PEM-no tether and PEM-DOTAP tether micro-slides at 40× magnification. Scale bar represents 10 μM. Viability of (C) MDA-MB-436 and (D) MCF-7 cells calculated at 0 and 6 hours after seeding on micro-slides with PEM-DOTAP tether. Fluorescence of live and dead cells were quantified for each (according to green or red fluorescence) and divided by total cell number to quantify percent of live and dead cells, respectively using CellProfiler. Data represents mean cell viability from three independent experiments (mean+/−SEM). (E) Representative images show viability of MDA-MB-436 cells tethered by DOTAP for 6 hours. Phase contrast images show total cell number, live, and dead at 4× magnification. Scale bar represents 200 μM.
Figure 35:
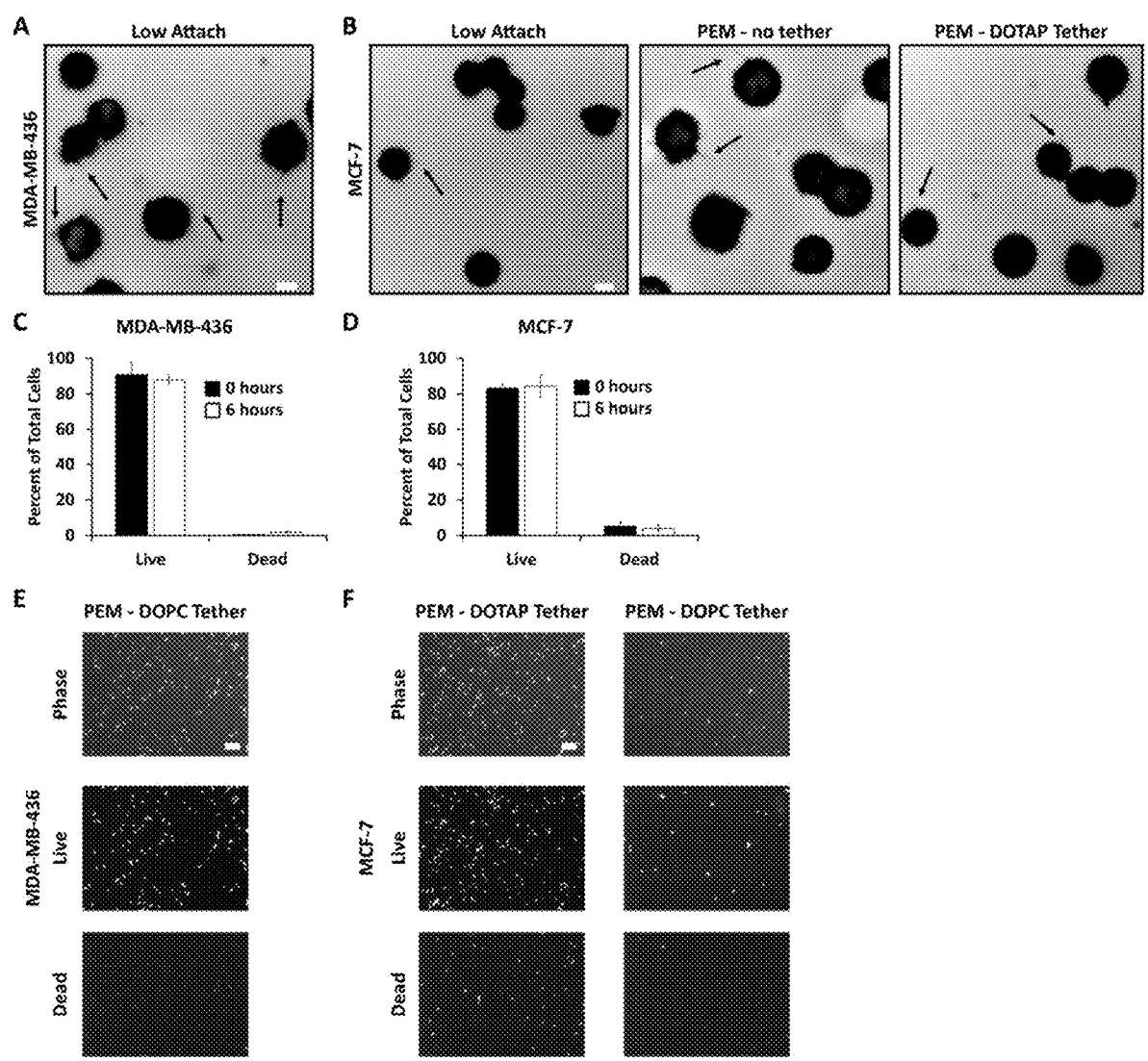
FIG. 35. Lipid tethering retains microtentacles and does not affect cell viability. (A) Representative image of McTNs (arrows) on MDA-MB-436 cells on a low-attach plate at 40× magnification. Scale bar represents 10 µM. (B) Representative images of McTNs (arrows) on MCF-7 cells on a low-attach plate, micro-slide with PEM-no tether, and micro-slide with PEM-DOTAP tether at 40× magnification. Scale bar represents 10 µM. (C) Representative images of MCF-7 cells seeded on micro-slides with PEM-DOTAP tether for 6 hours. Phase contrast images show total cell number, live and dead cells at 4× magnification. Scale bar represents 200 µM.

We next determined if lipid tethering with DOTAP maintained free-floating tumor cell characteristics. As a first indicator, McTN frequency of MDA-MB-436 and MCF-7 cells seeded on PEM and PEM-DOTAP coated slides was assessed. Blinded McTN counts on cells seeded on PEM-no tether and PEM-DOTAP tether were compared to counts corresponding to previously published methods on low-attach multi-well plates. There was no difference in McTN frequency on all three substrates (FIG. 28A), indicating that lipid tethering does not impact the ability of these cells to assemble McTNs. Representative epifluorescence images show McTNs on MDA-MB-436 cells seeded on low attach, PEM-no tether, and PEM-DOTAP tether surfaces (FIG. 28B and Supplemental FIG. 35A). MCF-7 cells had similar results with an overall lower frequency of McTNs, which is also seen in the epifluorescence images on all three substrates (FIG. 28A and Supplemental FIG. 35B). The overall McTN frequency of both cell lines also matched previously published data (Whipple R A, Cancer Res 2008; 68(14): 5678-5688). We next determined the viability of tumor cells tethered to DOTAP-PEM surfaces and observed minimal cell death after 6 hours of tethering (FIGS. 28C-4E and Supplemental FIG. 35C).

Figure 29:
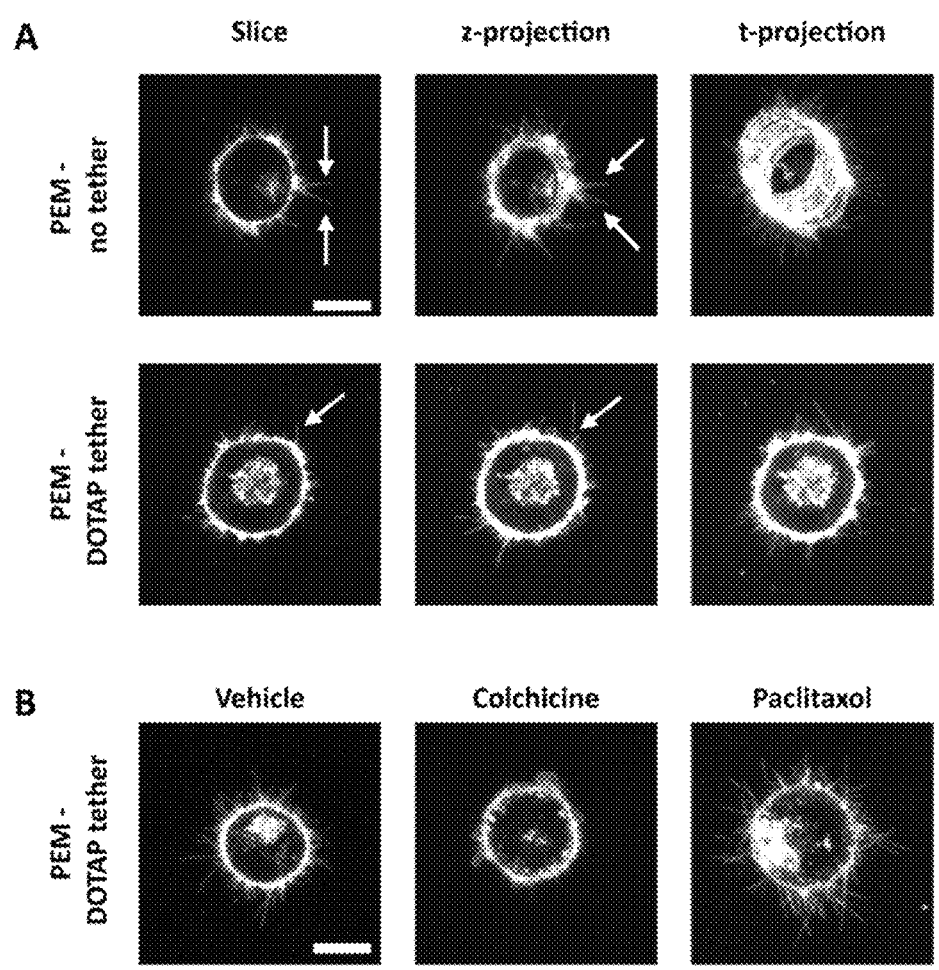
FIG. 29. Lipid tethering allows for real-time microtentacle imaging in response to drug treatment and minimizes effects of drift. (A) Microtentacle (arrows) imaging of MDA-MB-436 cells seeded on micro-slides with PEM-no tether (i-iii) and PEM-DOTAP tether (iv-vi). Representative 1 μM slice (i and iv), maximum z-projection of 5 slices at one time point (ii and v), and maximum t-projection after 20 frames (iii and vi) are shown at 60× magnification. (B) Microtentacle (arrow) imaging of MDA-MB-436 cells seeded on micro-slides with PEM-DOTAP tether after treatment with 5 uM colchicine for 15 minutes and 1 µg/ml Taxol for 120 minutes. Maximum intensity z-projections of five 1 µM slices at one time point are shown at 60× magnification. Scale bar represents 10 µM FIG. 30. PEM prevents attachment of MDA-MB-436 and MCF-7 breast cancer cells. Representative images of (A) MDA-MB-436 and (B) MCF-7 cells on micro-slides with 0 (uncoated), 1, 4, and 8 PMA/PAAm bilayers after one wash at 0, 6, and 24 hours at 4× magnification. Scale bar represents 200 µM.
Figure 30:
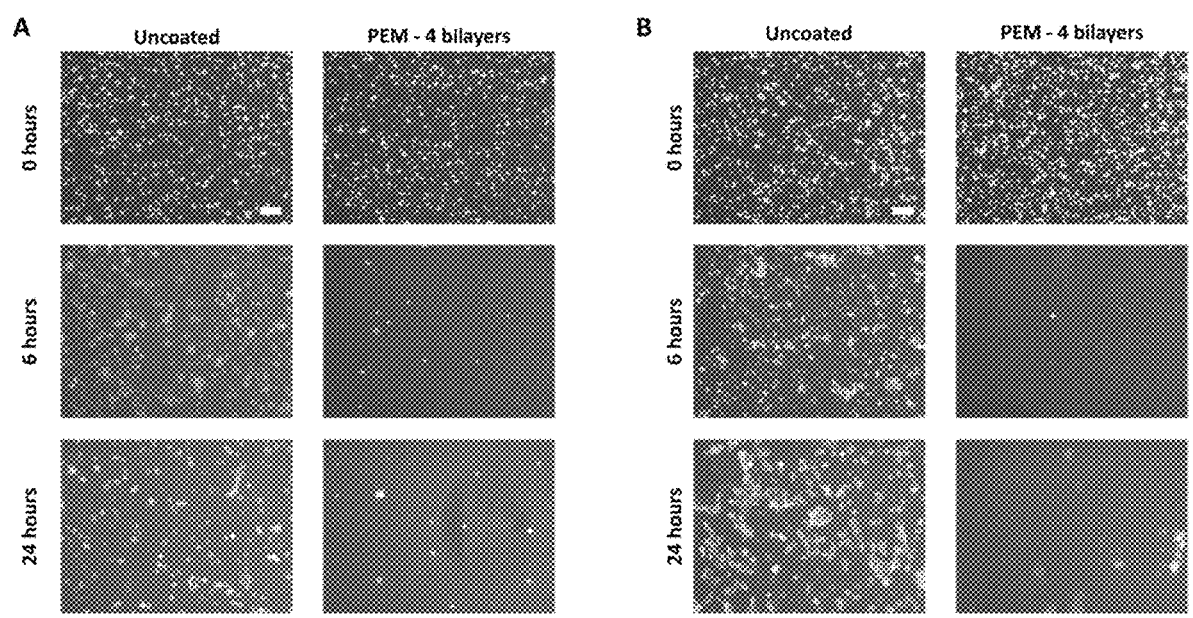

One of the greatest challenges in studying free-floating cell behavior is the difficulty measuring functional properties or behavior in real time. This is especially apparent when trying to image free-floating cells over time and in three dimensions. Epifluorescence is unable to capture McTNs in high resolution (FIG. 28B). Confocal microscopy of cells labeled with the fluorescent membrane dye, Cell-Mask, improves signal to noise and allows McTNs to be imaged with high contrast (FIG. 29Ai, arrows). However, since McTNs occur on free-floating cells, the time required to generate a 3-dimensional stack of z-slice images to completely trace microtentacle length yields significant blurring as free-floating cells drift over a surface to which they cannot attach, like PEM alone (FIG. 29Aii, arrows). The blurring effect of cell drift is even more apparent across a time projection (FIG. 29Aiii). We show here for the first time that tethering breast tumor cells not only retains McTNs (FIG. 29A iv, arrow), but can also eliminate blurring of McTNs in z-stacks allowing microtentacle length to be traced efficiently across z-stacks (FIG. 29A v, arrow) and prevents drift of the cell body during time-lapse imaging (FIG. 29A vi). Imaging over time shows how MDA-MB-436 cells seeded on PEM-coated slides drift whereas DOTAP tethering causes the cell to remain fixed in one location while still preserving McTN dynamics (not shown). It is interesting to note that debris is seen moving quickly through the field throughout the movie while the cell remains immobile and centered (not shown). The major advantage in imaging McTNs over time is being able to study their responses to drugs not only by McTN frequency, but also McTN dynamics. Here we show three dimensional z-stacks of MDA-MB-436 cells treated with the microtubule destabilizing agent, colchicine, and the microtubule stabilizing agent, taxol. Addition of colchicine decreases microtentacles and taxol enhances McTNs (FIG. 29B). Over time, colchicine shrinks McTNs and enhances cell blebbing whereas taxol hyperstabilizes McTNs dramatically decreasing their dynamics compared to vehicle control, which can be seen in high resolution movies (not shown) that would be otherwise impossible without lipid tethering, because drug addition would cause the cells to rapidly move out of the microscope field of view.

Therefore, this study shows that lipid tethering is an effective way to retain the free-floating characteristics of suspended tumor cells and enhances our ability to study their functional properties with high-resolution confocal microscopy. One application that is shown in this study is imaging McTN response to drugs in real-time where we can not only assess the effects of drugs on McTN frequency in a population as previously published, but also study other properties at a per-cell level such as McTN dynamics and time-dependent drug responses.

The majority of cancer-related deaths are due to the spread of tumor cells through the circulation from the primary site to a secondary organ (Chaffer C L and Weinberg R A, Science 2011; 331(6024):1559-1564). While in the circulation, tumor cells are in a non-adherent microenvironment that is unlike the conditions in a primary tumor or the metastatic site. In these non-adherent conditions tumor cells undergo many biochemical and structural changes that affect their sensitivity to therapies and their overall metastatic efficiency (Matrone M A, Cancer Res 2010; 70(20):7737-7741; Cristofanilli M and Mendelsohn J, Proc Natl Acad Sci USA 2006; 103(46):17073-17074). Classical drug studies and microscopy focus on analyzing tumor cells attached to a substrate due to the practical ease of analyzing cells under static conditions, but these methods do not properly recapitulate the free-floating environment of CTCs. Therefore, we have developed a microfluidic device that can hold tumor cells in place using a lipid moiety while preventing their attachment to a substrate. Tethering allows for spatial localization of detached tumor cells for real-time functional studies such as McTN analysis and imaging.

In this study, we show that incorporating a lipid moiety to substrates coated with PEM can passively immobilize tumor cells in a manner that preserves McTN formation and does not affect cell viability. Two lipids DOTAP and DOPC were added on slides coated with PMA/PAAm using LbL deposition. In this manner no cellular adhesive properties are necessary because the interaction of the cell membrane with the anchored lipid results in cell immobilization. The PEM-DOTAP tether was able successfully tether two breast cancer cell lines, MDA-MB-436 and MCF-7. MCF-7 cells had better tethering efficiency compared to the MDA-MB-436 cells, which may be due to differences in their membrane composition. The lipid moiety itself also altered cell retention as the DOPC lipid was unable to tether cells more effectively. While the cells are immobilized on the substrate, they still remain free-floating due because PEM prevent cell adhesion. Using this lipid tethering technology, we were able to perform high-resolution microscopy to image McTNs in real-time. While there was considerable loss of tethered cells with washing, this can be improved in the future through addition of a cross-linking step to strengthen the bond between the lipid and the PEM. We showed that McTN frequency of cells seeded on PEM-DOTAP did not change compared to cells seeded on PEM-no tether or previously published methods (low-attach plates) (Whipple R A, Cancer Res 2008; 68(14):5678-5688). PEM or DOTAP deposition also did not change cell viability. Without the spatial immobilization of the cell that the tethering offers tumor cells rapidly washed away from the substrate or move out of the field of view during microscopy, which makes real-time imaging of McTNs or other structures in a non-adherent cell practically impossible.

We were further able to leverage our microfluidic tethering technology to characterize the response of McTNs to microtubule-targeting drugs. We treated MDA-MB-436 cells with the microtubule depolymerizing agent, colchicine, and the microtubule stabilizing agent, paclitaxel. As previously reported by our group, colchicine inhibited McTN formation and taxol enhanced McTN formation of MDA-MB-436 cells (Whipple R A, Exp Cell Res 2007; 313(7): 1326-1336; Balzer E M, Breast Cancer Res Treat 2010; 121(1):65-78). But, for the first time, we were able expand upon these previous reports to visualize changes in McTN formation on a single cell level instead of in a population, as we have described previously. In addition, we were able to capture the motion of McTNs over time since the cells were fixed in place with the lipid tether revealing that taxol hyperstabilizes McTNs. Microtubule stability can enhance McTN formation and increase the re-attachment efficiency of tumor cells (Balzer E M, Breast Cancer Res Treat 2010; 121(1):65-78). Treatment of tumor cells with taxol causes enhanced microtubule stability and McTN formation, which results in greater lung trapping of tumor cells in experimental metastasis models in mice (Whipple R A, Exp Cell Res 2007; 313(7):1326-1336; Balzer E M, Oncogene 2010; 29(48):6402-6408; Balzer E M, Breast Cancer Res Treat 2010; 121(1):65-78). Therefore, analyzing McTN dynamics and their response to drugs has important implications on the metastatic ability of tumor cells. The improved image stability and time-dependent studies of McTNs that are enabled by tethering should allow many more quantitative McTN metrics to be measured more accurately (length, dynamics, etc.) and greatly improve on the qualitative observations that have only been possible until now.

CTCs play a critical role in disease prognosis and progression in patients with cancer. High numbers of CTCs correlate with increased metastasis and decreased survival of patients with metastatic cancer (Cristofanilli M, N Engl J Med 2004; 351(8):781-791; Krebs M G, J Clin Oncol 2011; 29(12):1556-1563; Plaks V, Science 2013; 341(6151):1186-1188; Yap T A, Clin Cancer Res 2014; 20(10):2553-2568). However, CTC enumeration alone may not be good marker for disease staging and prognosis (Plaks V, Science 2013; 341(6151):1186-1188). Therefore, improved biologic characterization of CTCs is necessary to better understand their clinical value. Numerous new approaches have been designed to improve CTC detection and enumeration, but the ability to study the functional properties of CTCs remains a major hurdle (Joosse SA, EMBO Mol Med 2015; 7(1):1-11). Ex vivo culture of CTCs in non-adherent conditions has provided one method to analyze CTCs from patients (Yu M, Science 2014; 345(6193): 216-220). The PEM-DOTAP tethering technology may be applied to these culturing methods to keep cells from adhering, but providing the additional benefits of single-cell analysis through staining and imaging. Studying the biology of CTCs has proven to have implications in their drug sensitivities and metastatic efficiency. Patterns of drug sensitivities have been linked to the genetic mutations present in individual CTC samples from breast cancer and lung cancer patients, indicating that a change in tumor genotypes during the course of treatment can lead to drug resistance (Yu M, Science 2014; 345(6193): 216-220; Cristofanilli M and Mendelsohn J, Proc Natl Acad Sci USA 2006; 103(46):17073-17074; Maheswaran S, N Engl J Med 2008; 359(4):366-377). As shown in this study, tethering tumor cells allows for rapid analysis of their response to specific drugs, which can be done in real-time. Markers of epithelial-to-mesenchymal transition (EMT) are also upregulated in CTCs with mesenchymal markers specifically enriched in CTC clusters, which have increased metastatic capabilities than single cells alone (Yu M, Science 2013; 339(6119):580-584; Aceto N, Cell 2014; 158(5):1110-1122). The microfluidic tethering device described in this study can be applied to these existing analysis techniques to do fundamental CTC studies at the single-cell level. Spatial localization of tethered tumor cells can be used to rapidly assess effects of drugs on cell viability, EMT markers, or McTNs which could all have implications on their metastatic phenotype. Tethering also allows these studies to be conducted in a manner that more closely recapitulates the free-floating environment found in the circulation. Ultimately, CTCs can play a role in informing therapeutic management and disease progression of cancer patients. Using PEM-DOTAP tethers to analyze the characteristics of CTC samples is a new tool to provide better, personalized treatment decisions for patients with cancer.

Methods

Cell Lines & Materials:

MDA-MB-436 and MCF-7 cell lines were purchased from ATCC and cultured with Dulbecco's Modified Eagle Medium supplemented with 10% fetal bovine serum and 1% penicillin-streptomycin solution. Poly(methacrylic acid) (PMA) (MW 100,000) and polyacrylamide (PAAm) (MW 5,000,000-6,000,000) were purchased from Polysciences. Poly(allylamine hydrochloride) (PAH) (MW ~200,000) was purchased from Alfa Aesar. 1,2-dioleoyl-3-trimethylammonium-propane (DOTAP) and 1,2-dioleoyl-sn-glycero-3-phosphocholine (DOPC) were purchased from Avanti Polar Lipids. Colchicine was purchased from Sigma and Taxol was purchased from Enzo Life Sciences.

PEM Film Deposition and Characterization on Planar Substrates

For multilayer film deposition, similar to methods previously reported (Yang S Y and Seo J-Y, *Colloids and Surfaces A: Physicochemical and Engineering Aspects* 2008; 313-314:526-529), PMA and PAAm were prepared as 0.01M solutions using ultrapure water and adjusted to pH 3. All polymer solutions were filtered with a 0.45 µm cellulose nitrate filter prior to use in multilayer film assembly. For planar substrates, quartz (Chemglass Life Sciences) or silicon (Silicon Inc.) were cut into 5 mm×25 mm substrates using a dicing saw (Model 1006, Micro Automation). Cut substrates were cleaned with sequential washing with acetone, ethanol, methanol, and deionized water then charged using an oxygen plasma Jupiter III system (March). These substrates were first immersed in the polycationic solution PAH (0.05M) for 15 minutes then rinsed twice using two separate baths of deionized water at pH 3 to remove any excess polymer. This primer layer was followed by immersion of the substrates into polyanionic PMA (0.01M) for 5 minutes followed by rinsing as above. The substrates were then immersed in a polycationic solution of PAAm (0.01M) for 5 minutes and rinsed. For additional bilayers, the process was repeated without the addition of the primer layer (PAH) until the desired number of bilayers was assembled. Lipid formulations comprised of 1,2-dioleoyl-sn-glycero-3-phosphocholine (DOPC) or 1,2-dioleoyl-3-trimethylammonium-propane (DOTAP) were obtained from Avanti Polar Lipids. These lipids were prepared as 0.01M solutions with pH 3 deionized water and sonicated for 60 minutes in a room temperature water bath. PEMs with a lipid tether were prepared by immersing PEM coated substrates in each lipid solution for 5 minutes followed by two rinsing steps. The final, coated substrates were removed from solution, blown dry with compressed, filtered air, and stored at room temperature prior to characterization. Film thickness and optical clarity after deposition onto silicon and quartz substrates were measured using a LSE stokes ellipsometer (Gaertner Scientific Corporation) and by measuring light transmittance at 600 nm using an Evolution 60 UV-visible spectrophotometer (Thermo Scientific), respectively.

PEM Film Deposition on Microscopy Slides and Multi-Well Plates:

Uncoated micro-slides (1µ-Slide VI 0.4) were obtained from Ibidi and tissue culture treated 96-well plates were obtained from Corning. To coat Ibidi slides, 120 µL of each polyelectrolyte solution was added to the microchannels and 75 µl of solution was added to each well of the multi-well plates. After incubation, solution was removed via aspiration and rinsed twice using 120 µL of pH 3 water. Bilayers of PMA and PAAm and terminated with either DOPC or DOTAP were assembled as above. Following deposition, slides were allowed to air dry for 1 hour at room temperature then stored at room temperature.

Attachment Image Analysis:

MDA-MB-436 and MCF-7 breast cancer cells were seeded on PEM coated micro-slides (50,000 cells/channel) ranging from 0 to 8 bilayers. An Olympus CKX4 microscope was used for all experiments to capture images at 4× magnification. Three pictures per channel were taken after cell seeding for each condition to quantify initial cell number (t0). At 6 hrs and 24 hrs media, was removed from the channel and the channel was washed once before addition of new media. Three images per channel were taken for each condition. The area of the image occupied with cells (as a percent) was quantified using CellProfiler (Broad institute) and the average from three images was calculated. The average percentage for each condition was then normalized to the area occupied at t0.

Attachment Cell Titer:

MDA-MB-436 and MCF-7 breast cancer cells were seeded on PEM coated 96-well plates (20,000 cells/well) ranging from 0 to 8 bilayers. At each time point (1, 3, 6, and 24 hours), media was removed from the well and the well was washed once before addition of fresh media. After the 24 hr time point an additional wash was done on all wells. Cell number was determined using CellTiter reagent according to manufacturer's instructions. Each time point was normalized to initial cell number from a reading done immediately after cell seeding.

PEM Viability:

MDA-MB-436 and MCF-7 breast cancer cells were seeded on PEM coated micro-slides with 4 bilayers (50,000 cells/channel). At 0, 6, and 24 hours Live/Dead (Life Technologies) reagent was added according to manufacturer's instructions. Corresponding phase contrast, live (calcein-AM) green fluorescence, and dead (ethidium homodimer-1) red fluorescence images were taken in triplicate at 4× magnification with an Olympus CKX41 fluorescence microscope. The number of cells in each image was quantified using CellProfiler and percent of live and dead cells were calculated by quantifying green fluorescence positive and red fluorescence positive cells, respectively, and dividing by total number of cells in the phase contrast image. GFP and Texas Red filters were used to for imaging. MDA-MB-436 and MCF-7 breast cancer cells were plated on 96-well black plates with 4 PEM bilayers (20,000 cells/well). At time 0, 1, 3, 6, and 24 hours Live/Dead reagent was added and read on a plate reader according to manufacturer's instructions. Relative fluorescence units (RFU) were normalized to time 0.

Tethering Washing:

MDA-MB-436 and MCF-7 cells were seeded on PEM coated micro-slides with 4 bilayers and addition of DOPC or DOTAP (50,000 cells/channel). Cells were incubated for 1 h to allow for tethering. To quantify initial cell number, three images per channel were taken for each condition at time 0. After 1 h, existing media was gently removed from the bottom port of each channel and fresh media was added to the top port. Following a wash, three images were taken per channel for each condition using an Olympus CKX41 microscope at 4× magnification. This process was repeated for each wash. The area of the image occupied with cells (as a percent) was quantified using CellProfiler and the average from three images was calculated. The average percentage for each condition was then normalized to the area occupied at time 0.

Tethering Viability:

MDA-MB-436 and MCF-7 cells were seeded on PEM coated micro-slides with 4 bilayers and addition of DOPC or DOTAP (50,000 cells/channel). Cells were incubated for 1 h to allow for tethering. After 1 h, one wash was done where the existing media was gently removed from the bottom port of each channel and fresh media was added to the top port. This wash was to ensure only tethered cells were analyzed. At 0 and 6 hours after washing, Live/Dead reagent was added according to manufacturer's instructions. Corresponding phase contrast, live (calcein-AM) green fluorescence, and dead (ethidium homodimer-1) red fluorescence images were taken in triplicate. The number of cells in each image was quantified using CellProfiler and percent of live and dead cells were calculated by quantifying green fluorescence positive and red fluorescence positive cells, respectively, and dividing by total number of cells in the phase contrast image. GFP and Texas Red filters were used to for imaging.

McTN Counting:

MDA-MB-436 cells were trypsinized, spun down, and resuspended in phenol red-free and serum-free DMEM. Cells were seeded on PEM coated micro-slides with 4 PEM bilayers, PEM coated micro-slides with 4 bilayers and the addition of DOTAP, or a low attach 24-well plate (50,000 cells/channel). Cells were incubated for 1 h to allow for tethering. After 1 h, one wash was done where the existing media was gently removed from the bottom port of each channel and fresh media was added to the top port. This wash was to ensure only tethered cells were analyzed. After this wash, CellMask orange (Life Technologies) cell membrane dye was added to each channel to a final concentration of 1:10,000. McTNs were scored blindly in a population of 100 cells/well as previously described. Representative images were taken at 40× magnification with an Olympus CKX41 fluorescence microscope.

Imaging Drift and Drug Treatments:

MDA-MB-436 cells were trypsinized, spun down, and resuspended in phenol red-free and serum-free DMEM. Cells were seeded on PEM coated micro-slides with 4 bilayers and PEM coated micro-slides with 4 bilayers and the addition of DOTAP (50,000 cells/channel). Cells were incubated for 1 h to allow for tethering. After 1 h, one wash was done where the existing media was gently removed from the bottom port of each channel and fresh media was added to top port. This wash was to ensure only tethered cells were analyzed. After this wash, CellMask orange cell membrane dye was added to each channel to a final concentration of 1:10,000. McTN imaging was done on an Olympus FV100 confocal laser scanning microscope at 60× magnification. Five 1 uM slices and 20 frames at a 10 sec frame rate were taken for at least five image sets for each condition. Colchicine was added to each channel at a final concentration of 5 uM and cells were imaged after 15 minutes. Taxol was added to each channel at final concentration of 1 μg/ml and imaged after 120 minutes. Cells were again imaged with five 1 μM slices and 20 frames at a 10 second frame rate.

Statistical Analysis:

Graphpad Prism (version 6.02) was used to determine all statistic comparisons. One-way ANOVA tests were performed with a Tukey post-test as indicated. A p-value of 0.05 or less was considered statistically significant.

Example 8

Quantitative Methods to Measure McTN Characteristics and Dynamics

Figure 36:
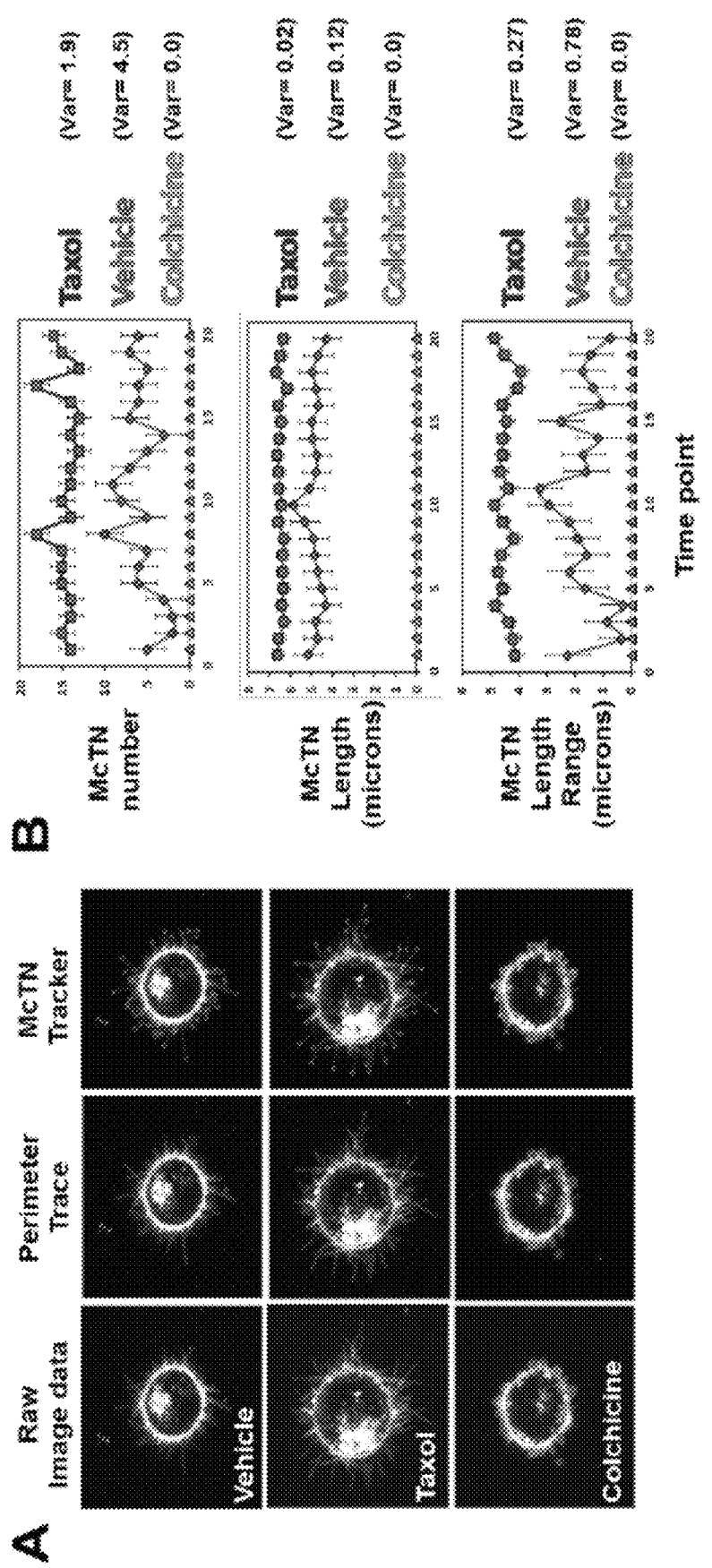
FIG. 36. Quantitative image analysis of time-dependent McTN metrics. A) MDA-436 breast tumor cells that were tethered with a PEM+DOTAP surface coating were imaged for McTNs with confocal microscopy (5 z-slices of 1 µm, max intensity projection shown). A custom MATLAB algorithm was applied to the image data to find the cell periphery (Perimeter trace) and then locate local points of maximum perimeter curvature (McTN Tracker). B) Analyzing cells at 10 s timepoints allows the dynamic movement of McTNs under vehicle-treated conditions to be appreciated (blue lines). Stabilization of McTNs with Taxol (1 µg/ml) increases the number of McTNs per cell>4 µm from cell periphery (McTN number) and McTN length, but also strongly reduces the range of McTN measurements and the variance of all metrics. Depolymerization of microtubules with Colchicine (50 µM) completely eliminates McTNs.

Using breast cancer cell lines, we developed a custom MATLAB algorithm to identify McTN ends (points of local surface curvature maxima on a perimeter trace). Combined with automated identification of the cell body (erosion mask), both the number and lengths of individual McTNs can be defined. Now that we have succeeded in tethering tumor cells to PEM-DOTAP surfaces, it dramatically improves our ability to collect time-lapse confocal imaging without the blurring that occurs with even minor cell drift. We now demonstrate that our image analysis algorithm can be applied to define quantitative changes in McTN behavior following drug treatment (FIG. 36). Stabilization of microtubules with Taxol increases the number of McTNs per cell and average McTN length. Disruption of microtubules with Colchicine completely inhibits McTN generation. The new dynamic measurements also show that average McTNs/cell, average McTN length and the range of McTN lengths/cell change rapidly in vehicle-treated control cells. By comparison, the variance of all three measures is reduced in Taxol-treated cells, reflecting the effect of stabilizing microtubules. Individual McTN tips can also be followed with MATLAB particle tracking to quantitate McTN dynamics (FIG. 37).

Example 9

Crosslinking of DOTAP Tether to PEMs

Figure 37:
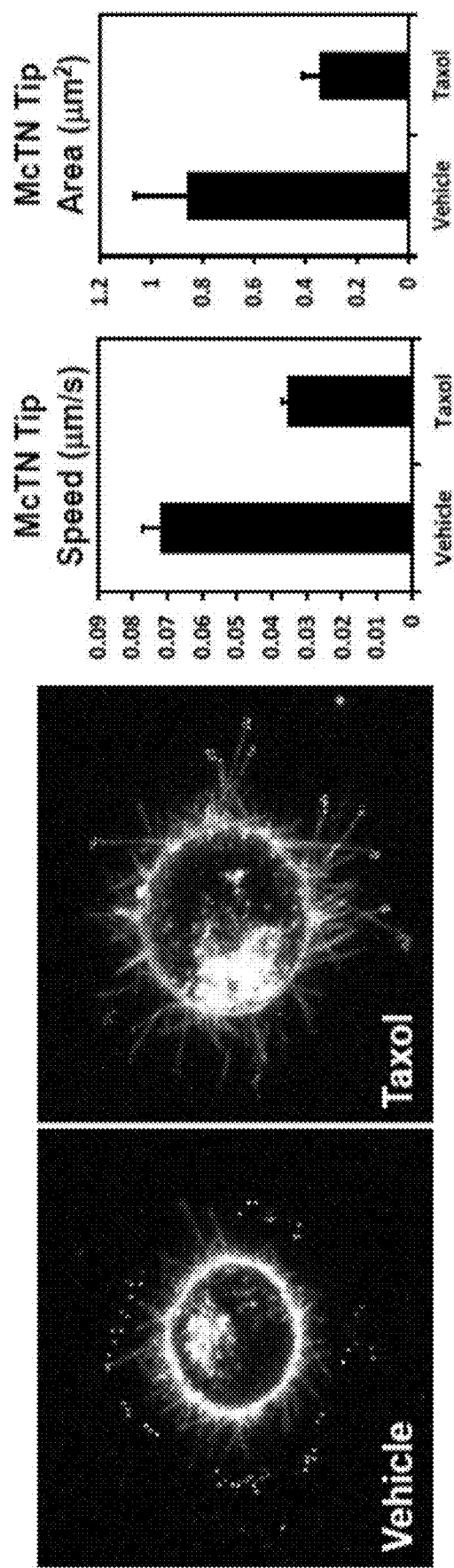
FIG. 37. Tracking individual McTN tip motion. Applying a particle-tracking algorithm to the McTN tips identified in FIG. 36 allows the movement of individual McTN tips (color-coded) to be followed over time. Taxol has clear effects to reduce average McTN speed and make McTNs more persistent (reduces the area over which a McTN moves).
Figure 38:
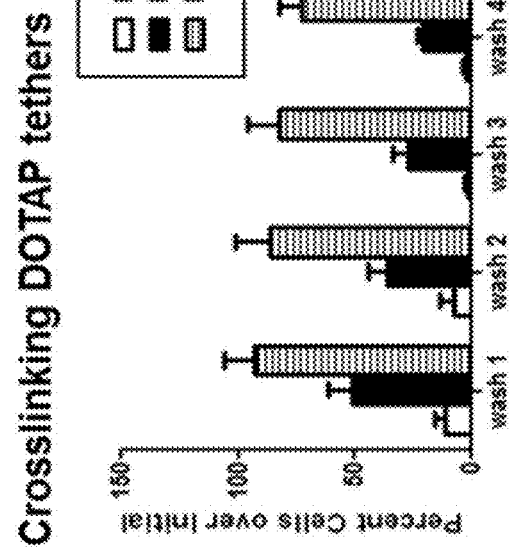
FIG. 38. PEM coating for McTN studies. A) Blinded McTN scoring demonstrates that McTN frequencies remain the same for cells regardless of whether they are suspended over low-attach plates (published method), PEMs, or PEMs with an integrated DOTAP cell tether. B) DOTAP tethers secured through charge interaction do not hold cells efficiently through multiple washes (black bars). Crosslinking the DOTAP to the PEM with formaldehyde significantly improves initial tethering efficiency and resistance to washing (hatched bars).
Figure 38:
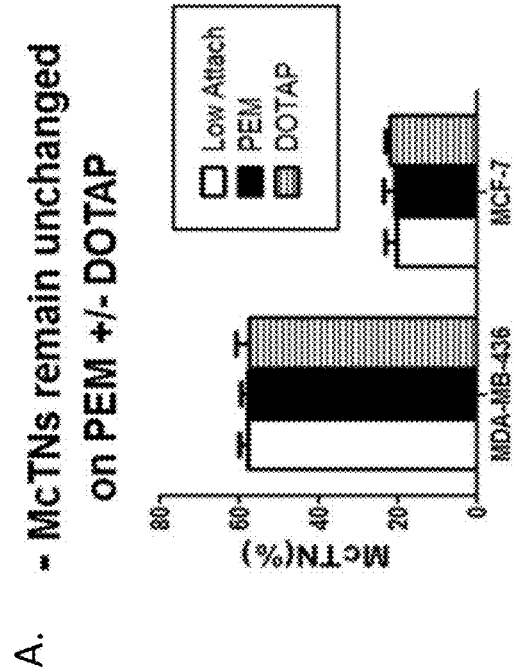

New quantitative data demonstrate that PEM coatings allow prolonged imaging of McTN on tumor cells (FIG. 36-37). We assembled PEMs from alternating layers of polymethacrylic acid (PMA) and polyacrylamide (PAAm) to coat microfluidic channels with very thin (100-1000 Angstroms) multilayers that retain high optical clarity. Even a single bilayer is capable of significantly inhibiting tumor cell attachment for up to 24 hours Importantly, McTN activity remains unchanged when cells are plated over either PEMs or held in place with DOTAP tethers coupled to the PEM (FIG. 38A). Reactive amine groups in the PAAm allow the DOTAP tether to be chemically cross-linked to the PEM with formaldehyde, which dramatically improves retention of tethered tumor cells during multiple washes (FIG. 38B). This crosslinking approach enables us to conduct improved imaging, time-dependent drug treatments without causing cell drift, but also illustrates that photo-crosslinking could be used to develop patterned arrays to facilitate tumor cell mechanical measurements and cell fate studies.

Example 10

Tethering Arrays by Photo-Crosslinking the Tether to the Substrate

In this Example, the lipid tether is photo-crosslinked directly into a PEM coating to enable a one-step tethering of non-adherent tumor cells on patterned surfaces that allow rapid preparation of microfluidic PEM capture devices for high-throughput clinical use.

Photo-crosslinking will allow patterns of lipid tethers to be generated on PEM coatings within intact microfluidic channels. An aryl azide group is used that can be activated with 380 nm light to form covalent crosslinks with the PEM. (FIG. 39). A photolithography mask is prepared in the Fablab and the Suss mask aligner is used—which is able to pattern features >1 μm—to directly illuminate PEM coated Ibidi microchannels with 7 μm islands and 40 μm center spacing. A photocrosslinkable lipid (FIG. 39) can be used in this experiment, which can be obtained by Avanti Polar Lipids, Inc. This approach will eliminate the need for microcontact printing.

The rationale for developing patterned arrays is so that cells can be held close together for rapid imaging of groups (FIG. 40A), but also stay far enough apart so that clustering is minimized (FIG. 40A). Patterned arrays will also enable us to more accurately compare McTN behavior and mechanical measurements with micropipette aspiration and AFM conducted at the same coordinates (FIG. 40B). Engineered arrays could also probe questions like the spacing that can promote cell-cell attachment in the presence and absence of drugs (FIG. 40C). Finally, the technique can be used to answer the question of whether increases in stem cell characteristics caused by drug treatments result from the selection of cancer stem cells (by killing non-stem cells), or if the mechanical changes imposed by cytoskeletal drugs can actually induce stem cell conversion. Evidence using the ROCK inhibitor of actin contraction (Y27632) suggest that conversion is occurring, which has important clinical implications (drugs directly causing increases in stem cells) (Liu, X., et al. (2012). "ROCK inhibitor and feeder cells induce the conditional reprogramming of epithelial cells." *Am J Pathol* 180(2): 599-607; Suprynowicz, F. A., et al. (2012). "Conditionally reprogrammed cells represent a stem-like state of adult epithelial cells." *Proc Natl Acad Sci USA* 109(49): 20035-20040). Since stem cell studies in solid cancers are conducted on non-adherent cells, the invention's tethered cell arrays will enable us to distinguish the effects of stem cell conversion and selection by allowing cell fate to be tracked efficiently as tumor cells grow into stem cell spheres (FIG. 40D).

While there have been shown and described what are presently believed to be the preferred embodiments of the present invention, those skilled in the art will realize that other and further embodiments can be made without departing from the spirit and scope of the invention described in this application, and this application includes all such modifications that are within the intended scope of the claims set forth herein. All patents and publications mentioned and/or cited herein are incorporated by reference to the same extent as if each individual publication was specifically and individually indicated as having been incorporated by reference in its entirety.

What is claimed is:

1. A device for assaying living cells comprising a substrate, wherein the substrate comprises a tethering molecule, wherein the tethering molecule adheres to the substrate and is capable of directly interacting with a cell membrane of a cell, wherein the cell maintains a free-floating, non-adherent character when bound to the tethering molecule, wherein the device exhibits an optical clarity of at least about 90%, wherein the substrate is coated with one or more layers of one or more materials that substantially inhibit the cells from adhering to the substrate, wherein a surface of the substrate is capable of being fixed to the cell by a chemical fixative.

2. The device of claim 1, wherein the substrate is coated with polyelectrolyte multilayer films (PEMs).

3. The device of claim 2, wherein the PEMs are formed from a combination of polymethacrylic acid (PMA) and polyacrylamide (PAAm).

4. The device of claim 2, wherein the PEMs have a thickness of from about 10 nm to about 100 nm.

5. The device of claim 2, wherein the PEMs incorporate tethering molecules in their top surface.

6. The device of claim 2, wherein PEMs are prepared by adsorption of alternating layers of polycationic and polyanionic aqueous solutions to the substrate that assemble through electrostatic or hydrogen bonding.

7. The device of claim 1, wherein the device is a microfluidic device and the substrate is a microfluidic slide or microfluidic channel.

8. The device of claim 1, wherein the tether is a charged lipid molecule.

9. The device of claim 1, wherein the tether is selected from the group consisting of glycerophospholipid, phosphatidylcholine, phosphatidylethanolamine, phosphatidylglycerol, phosphatidylserine, phosphatidylinositol, phosphatidylinositolphosphate, phosphatidic acid, 1,2-dioleoyl-3-trimethylammonium-propane (DOTAP), 1,2-dioleoyl-sn-glycero-3-phosphocholine (DOPC), 18:O-LysoPG and 15:O (3)-16:1-CA.

10. The device of claim 1, wherein the tethering molecules are crosslinked to the substrate using a crosslinking agent.

11. The device of claim 1, further comprising a cell directly bound to the tethering molecule.

12. The device of claim 11, wherein the cell is selected from the group consisting of a blood cell, a bone marrow cell, a lymph cell, a stem cell, an oocyte, a muscle cell, an epithelial cell and a tumor cell.

13. The device of claim 12, wherein the tumor cell is from a cancer selected from the group consisting of breast cancer, prostate cancer, lung cancer, bladder cancer, pancreatic cancer, brain cancer, liver cancer, testicular cancer, thyroid cancer, skin cancer, colon cancer, ovarian cancer, cervical cancer, and uterine cancer.

14. The device of claim 12, wherein the tumor cell is a primary tumor cell that has been isolated from a solid tumor from a subject.

15. The device of claim 13, wherein the tumor cell comprises one or more microtentacles.

16. The device of claim 14, wherein the tumor cell is isolated directly from a non-removed tumor, from a tumor cell biopsy, from circulating tumor cells, or from a tumor that is surgically removed.

17. The device of claim 1, wherein the device is a microfluidic device comprising one or more channels.

18. The device of claim 1, wherein the device comprises tethering molecules that are organized into an array pattern on the substrate.

19. The device of claim 18, wherein the tethering molecules are organized into an array pattern on the substrate by a process comprising photo-crosslinking of the tether to the substrate at defined sites.

20. The device of claim 1, wherein the substrate is coated with one or more cationic and/or anionic polymers.

21. The device of claim 1, wherein the tethering molecule holds the cell in a substantially fixed position.

22. The device of claim 1, wherein the substrate is substantially optically clear to enable visualization of the cells using microscopy.

23. The device of claim 1, wherein the device comprises tethering molecules that are organized into an array pattern on the substrate by a process comprising microcontact printing.

24. The device of claim 1, wherein the tether comprises an aryl azide group that can be photo-crosslinked to the substrate.

25. The device of claim 1, wherein the device comprises tethering molecules that are organized into an array pattern on the substrate, wherein the pattern array comprises islands of from about 4-15 µm in size with about 25-100 µm center spacing.

26. The device of claim 1, wherein the device comprises tethering molecules that are organized into an array pattern on the substrate, wherein the pattern array comprises islands of about 7 µm in size with about 40 µm center spacing.

27. The device of claim 1, wherein the substrate is made of plastic or glass.

28. A method for imaging microtentacles on isolated, living, primary tumor cells from a cancer subject, comprising:
   i) obtaining one or more living primary tumor cells that has been isolated from a solid tumor from the subject;
   ii) adding the one or more cells to the substrate of the device of claim 1; and
   iii) imaging the one or more living primary tumor cells and detecting the microtentacles, wherein the one or more tumor cells are non-adherently tethered to the substrate during imaging of the tumor cells.

29. A method of identifying a subject with an increased likelihood of having or developing metastatic cancer comprising:
  i) obtaining one or more living primary tumor cells that has been isolated from a solid tumor from the subject;
  ii) adding the one or more cells to the substrate of the device of claim 1;
  iii) imaging the one or more living primary tumor cells, wherein the one or more tumor cells are non-adherently tethered to the substrate during imaging of the tumor cells; and
  iv) scoring the one or more imaged cells for microtentacles to determine whether the subject has an increased likelihood of having or developing metastatic cancer.

30. A method for determining whether a candidate drug inhibits or promotes microtentacle formation and/or stability on isolated, living, primary tumor cells from a cancer subject comprising:
  i) obtaining one or more living primary tumor cells that has been isolated from a solid tumor from the subject;
  ii) adding the one or more cells to the substrate of the device of claim 1;
  iii) contacting the one or more living primary tumor cells with the candidate drug;
  iv) imaging the one or more living primary tumor cells treated with the candidate drug, wherein the one or more tumor cells are non-adherently tethered to the substrate during imaging of the tumor cells; and
  v) scoring the one or more imaged cells for microtentacles to determine whether a candidate drug inhibits or promotes microtentacle formation and/or stability.

31. A method for determining the stem cell potential of tumor cells from a cancer subject comprising:
  i) obtaining one or more living primary tumor cells that has been isolated from a solid tumor from the subject;
  ii) adding the one or more cells to the substrate of the device of claim 1;
  iii) optionally treating the cells with a candidate drug;
  iv) imaging the one or more living primary tumor cells, wherein the one or more tumor cells are non-adherently tethered to the substrate during imaging of the tumor cells; and
  v) performing one or more of the following steps to determine the stem cell potential of the tumor cell:
    a. scoring the tethered cells for microtentacles;
    b. scoring tethered cells for their ability to form stem cell spheres; and
    c. tracking the fates of individual tethered cells to determine their ability to form stem cell spheres.

* * * * *